(12) United States Patent
Kotani et al.

(10) Patent No.: US 10,174,304 B2
(45) Date of Patent: Jan. 8, 2019

(54) EXPRESSION VECTOR AND METHOD FOR PRODUCING PROTEIN

(71) Applicant: Asahi Glass Company, Limited, Tokyo (JP)

(72) Inventors: Tetsuya Kotani, Tokyo (JP); Alimujiang Yidirei, Tokyo (JP); Hideki Tohda, Tokyo (JP)

(73) Assignee: AGC INC., Tokyo (JP)

( * ) Notice: Subject to any disclaimer, the term of this patent is extended or adjusted under 35 U.S.C. 154(b) by 166 days.

(21) Appl. No.: 14/337,784

(22) Filed: Jul. 22, 2014

(65) Prior Publication Data

US 2014/0335622 A1 Nov. 13, 2014

Related U.S. Application Data

(63) Continuation of application No. PCT/JP2013/051209, filed on Jan. 22, 2013.

(30) Foreign Application Priority Data

Jan. 23, 2012 (JP) ................................. 2012-010569

(51) Int. Cl.
| | |
|---|---|
| C12N 9/90 | (2006.01) |
| C12P 21/02 | (2006.01) |
| C12N 15/62 | (2006.01) |
| C12N 15/81 | (2006.01) |

(52) U.S. Cl.
CPC ............. *C12N 9/90* (2013.01); *C12N 15/625* (2013.01); *C12N 15/815* (2013.01); *C12P 21/02* (2013.01); *C07K 2319/04* (2013.01)

(58) Field of Classification Search
None
See application file for complete search history.

(56) References Cited

U.S. PATENT DOCUMENTS

2007/0037254 A1* 2/2007 Chisholm ........ C07K 14/43595
435/69.1
2010/0311122 A1* 12/2010 Choi .................. C07K 14/4725
435/69.4

FOREIGN PATENT DOCUMENTS

| EP | 0 509 841 A2 | 10/1992 |
|---|---|---|
| EP | 0 509 841 A3 | 10/1992 |
| EP | 2 210 940 A1 | 7/2010 |
| JP | 11-75879 A | 3/1999 |
| WO | WO 92/13955 A1 | 8/1992 |
| WO | 96/23890 | 8/1996 |
| WO | WO 2005/061719 A1 | 7/2005 |

OTHER PUBLICATIONS

Kajino et al. (Applied and Environmental Microbiology, 66(2): 638-642, 2000).*
Kajino et al. (Journal of Bioscience and Bioengineering, 87(1):37-42, 1999).*
Perez et al. (J. Virol., 61(5): 1609-1614, 1987).*
Kajino et al. "A Protein Disulfide Isomerase Gene Fusion Expression System That Increases the Extracellular Productivity of *Bacillus brevis*". Applied and Environmental Microbiology, vol. 66, No. 2, Feb. 2000, pp. 638-642.
Mukaiyama et al. "Overexpression of protein disulfide isomerases enhances secretion of recombinant human transferrin in *Schizosaccharomyces pombe*", Applied Microbiology and Biotechnology, vol. 86, No. 4, Dec. 16, 2009, pp. 1135-1143.
Tian et al. "The Crystal Structure of Yeast Protein Disulfide Isomerase Suggests Cooperativity between Its Active Sites", Cell 124,Jan. 13, 2006, pp. 61-73.
International Search Report issued in PCT/JP2013/051209 dated Apr. 9, 2013.
Inan, Mehmet, et al., "Enhancement of Protein Secretion in *Pichia pastoris* by Overexpression of Protein Disulfide Isomerase," Biotechnology and Bioengineering, vol. 93, No. 4, Mar. 5, 2006 (8 pages).

* cited by examiner

*Primary Examiner* — Nelson B Moseley, II
(74) *Attorney, Agent, or Firm* — Oblon, McClelland, Maier & Neustadt, L.L.P.

(57) ABSTRACT

Provided are: an expression vector for secreting a protein (Z) to be recovered or a fusion protein having the protein (Z) moiety therein; a method for producing a transformant using the expression vector; the transformant; and a method for producing a protein using the transformant. An expression vector comprising an expression cassette containing a structural gene sequence (y) encoding a protein (Y), a structural gene sequence (z) located downstream from the structural gene sequence (y) and encoding a protein (Z) that is a protein to be recovered, and a promoter sequence and a terminator sequence for expressing a fusion protein containing the protein (Y) moiety and the protein (Z) moiety, characterized in that the protein (Y) is a full-length protein of protein disulfide isomerase 1 (PDI1), a partial protein of PDI1, or a mutant protein of the full-length protein or the partial protein.

16 Claims, 15 Drawing Sheets

Specification includes a Sequence Listing.

FIG. 2

EXPRESSION VECTOR AND METHOD FOR PRODUCING PROTEIN

This application is a continuation of PCT Application No. PCT/JP2013/051209, filed on Jan. 22, 2013, which is based upon and claims the benefit of priority from Japanese Patent Application No. 2012-010569 filed on Jan. 23, 2012. The contents of those applications are incorporated herein by reference in their entireties.

TECHNICAL FIELD

The present invention relates to an expression vector for secretory production of a protein, a transformant prepared by using the vector and a method for producing the transformant, and method for producing a protein by using the transformant.

BACKGROUND ART

Heretofore, production of foreign proteins by using gene recombination technology has been actively carried out by using microorganisms including *Escherichia coli*, budding yeast (*Saccharomyces cerevisiae*), a microorganism of the genus *Bacillus*, etc., animal cells, plant cells, or insect cells. Proteins derived from various organisms are considered as objects of the production, and many proteins have already been produced industrially by using such organisms and have been used for pharmaceuticals, etc. Particularly, the secretory production of a foreign protein is preferred from the view point of easiness in purification as compared with a case wherein produced foreign proteins are accumulated in inside of a cell, and is advantageous since proteins produced by secretion enter into a secretory pathway of a host cell and are subjected to an appropriate treatment such as disulfide bond formation or saccharide chain formation thereby to form a conformational structure quite similar or identical to that of natural proteins.

By producing a foreign protein in a state where a secretion signal peptide is added to its N-terminal, the foreign protein can be produced by secretion. For example, as a secretion signal recognized by fission yeast *Schizosaccharomyces pombe* (hereinafter referred to as *S. pombe*), a polypeptide derived from a secretion signal of a mating pheromone (P-factor) precursor involved in the mating of *S. pombe* may be mentioned (refer to Patent Document 1). When cultivating a *S. pombe* transformant introduced with a structural gene encoding a fusion protein having the polypeptide at the N-terminal of a foreign protein, the produced fusion protein is separated into a signal peptide and the foreign protein in the Golgi apparatus or the endoplasmic reticulum (ER), and accordingly, the foreign protein will be secreted from the host cell into a culture broth.

Further, with regard to the increase in the production amount of secretory proteins, it has been known that co-expression of a foreign secretory protein with PDI1 increases the secretory production amount (the amount of a secreted protein, among the proteins produced by the host) of the secretory protein (refer to Non-Patent Document 1). PDI1 (Protein disulfide isomerase 1) has a molecular chaperone function, and is a protein localized to the ER.

PRIOR ART DOCUMENTS

Patent Document(s)

Patent Document 1: WO 1996/23890

Non-Patent Document(s)

Non-Patent Document 1: Mukaiyama, et al., Applied Microbiology and Biotechnology, (2010) vol. 86, No. 4, pp. 1135-1143.

DISCLOSURE OF INVENTION

Technical Problem

The secretion signal protein disclosed in Patent Document 1 is excellent since it enables secretory production of a protein to be recovered in a protein expression system using *S. pombe* as a host, and mass production of the protein. However, depending upon the types of a protein to be recovered, the production amount may not be sufficient in some cases, and therefore development of an expression system enabling secretory production of a protein with higher efficiency has been desired. Further, also in the above-mentioned co-expression system, depending upon the types of a protein to be recovered, the production amount may not be sufficient in some cases, and there have been problems such that produced proteins do not pass through a secretory pathway efficiently and coagulation of the proteins occurs in the secretory pathway.

The object of the present invention is to provide an expression vector for high-efficient secretory production of a protein to be recovered or a fusion protein having a moiety of the protein to be recovered, and a method for producing the protein or the fusion protein from a transformant introduced with the expression vector.

Solution to Problem

The present inventors conducted extensive studies to resolve the above-mentioned problems, and as a result, found that, by expressing a protein (Z) that is a protein to be recovered after fusing it with PDI1 (Protein disulfide isomerase 1) that is known to have a molecular chaperone function, the protein (Z) or a fusion protein having the protein (Z) moiety can be produced by secretion efficiently. The present invention has been accomplished based on such findings.

The expression vector, the method for producing a transformant, the transformant, the method for producing a protein, and the cloning vector of the present invention are the following [1] to [15].

[1] An expression vector comprising an expression cassette containing a structural gene sequence (y) encoding a protein (Y), a structural gene sequence (z) located downstream from the structural gene sequence (y) and encoding a protein (Z) that is a protein to be recovered, and a promoter sequence and a terminator sequence for expressing a fusion protein containing the protein (Y) moiety and the protein (Z) moiety, characterized in that the protein (Y) is a full-length protein of protein disulfide isomerase 1 (PDI1), a partial protein of PDI1, or a mutant protein of the full-length protein or the partial protein.

[2] The expression vector according to the above [1], wherein the protein (Y) has an endoplasmic reticulum targeting signal of PDI1.

[3] The expression vector according to the above [1] or [2], wherein the protein (Y) is a partial protein comprised of an endoplasmic reticulum targeting signal, an a-domain, a b-domain and a x-domain, a partial protein comprised of an endoplasmic reticulum targeting signal, an a-domain, a b-domain, a b'-domain and a x-domain, or a mutant protein of either of these partial proteins.

[4] The expression vector according to any one of the above [1] to [3], wherein the PDI1 is PDI1 derived from yeast, PDI1 derived from filamentous fungus, or PDI1 derived from human.

[5] The expression vector according to any one of the above [1] to [4], further comprising a structural gene sequence (w), in between the structural gene sequence (y) and the structural gene sequence (z), encoding a cleavage site (W) that is comprised of an amino acid or a peptide and functions as a site to be cleaved at the N-terminal side of the protein (Z) moiety either in inside or outside of a cell.

[6] The expression vector according to the above [5], wherein the cleavage site (W) is a site to be cleaved at the N-terminal side of the protein (Z) moiety of the fusion protein in inside of a cell.

[7] The expression vector according to the above [6], wherein the cleavage site (W) is KR (K: lysine, R: arginine), or a peptide comprised of at least three amino acids and has KR at its C-terminal side that binds to the protein (Z) moiety.

[8] The expression vector according to the above [5], wherein the cleavage site (W) is a site recognized by a protease that can cleave the N-terminal side of the protein (Z) moiety of the fusion protein.

[9] The expression vector according to any one of the above [1] to [8], wherein the protein (Y) contains at least an endoplasmic reticulum targeting signal, an a-domain, and a b-domain.

[10] A method for producing a transformant, characterized in that the expression vector as defined in any one of the above [1] to [9] is introduced into a host cell.

Further, the method for producing a transformant is preferably the following production method of [10-2].

[10-2] A method for producing a transformant, characterized in that the expression vector as defined in any one of the above [1] to [9] is introduced into a host cell for integrating the expression cassette of the expression vector into at least one position of a chromosome of a host cell.

[11] A transformant comprising the expression vector as defined in any one of the above [1] to [9] as an extrachromosomal gene.

[12] A transformant comprising the expression cassette of the expression vector as defined in any one of the above [1] to [9] in a chromosome.

Further, the host cell for the transformant of the above [11] or [12] is preferably a yeast or a filamentous fungus, more preferably a yeast of the genus *Schizosaccharomyces*.

[13] A method for producing a protein, comprising cultivating the transformant as defined in the above [11] or [12] and recovering the fusion protein or the protein (Z) from a culture broth obtained by cultivation.

Further, the method for producing a protein is preferably the following method of [13-2] or [14].

[13-2] A method for producing a protein, comprising cultivating a transformant having the expression cassette of the expression vector as defined in the above [6] or [7] in a chromosome or having the expression vector as defined in the above [6] or [7] as an extrachromosomal gene, and recovering the protein (Z) from a culture broth obtained by cultivation.

[14] A method for producing a protein, comprising cultivating a transformant having the expression cassette of the expression vector as defined in the above [8] in a chromosome or having the expression vector as defined in the above [8] as an extrachromosomal gene, recovering the fusion protein from a culture broth obtained by cultivation, and cleaving the N-terminal side of the protein (Z) moiety of the fusion protein by means of a protease to produce the protein (Z).

[15] A cloning vector comprising a promoter sequence capable of functioning in a host cell, a structural gene sequence (y) encoding a protein (Y) located downstream from the promoter and regulated by the promoter, a cloning site located downstream from the structural gene sequence (y) for introducing a structural gene, and a terminator sequence capable of functioning in the host cell, characterized in that the protein (Y) is a full-length protein of protein disulfide isomerase 1 (PDI1), a partial protein of PDI1, or a mutant protein of the full-length protein or the partial protein.

Advantageous Effects of Invention

According to the expression vector of the present invention, it is possible to provide a transformant which can produce a protein by secretion from the host cell.

Further, according to the method for producing a protein of the present invention which uses the transformant, it is possible to secrete proteins efficiently.

In a case where the protein secreted from the transformant is a protein to be recovered (i.e. protein (Z)), it is possible to recover the protein (Z) from a culture broth. Further, in a case where the secreted protein is a fusion protein, the protein (Z) can be produced from the fusion protein.

BRIEF DESCRIPTION OF DRAWINGS

FIG. 2 shows alignment of the amino acid sequences of PDIs derived from yeast, filamentous fungi, and human.

DESCRIPTION OF EMBODIMENTS

Expression Vector

The expression vector of the present invention has an expression cassette containing a structural gene sequence (y) encoding a protein (Y), a structural gene sequence (z) located downstream from the structural gene sequence (y) and encoding a protein (Z) that is a protein to be recovered, and a promoter sequence and a terminator sequence for expressing a fusion protein containing the protein (Y) moiety and the protein (Z) moiety, characterized in that the protein (Y) is a full-length protein of PDI1, a partial protein of PDI1, or a mutant protein of the full-length protein or the partial protein.

By using a full-length protein of PDI1, a partial protein of PDI1, or a mutant protein thereof instead of a secretion signal protein, it is possible to produce a protein by secretion from a host cell efficiently. In a case where the secreted protein is a protein (Z), it is possible to recover the protein (Z) from a culture broth. In a case where the secreted protein is a fusion protein, the protein (Z) can be obtained by cleaving the fusion protein at the N-terminal side of the protein (Z) moiety of the fusion protein, in a culture broth, or after separating the fusion protein from a culture broth.

(Protein (Y))

Protein (Y) is the a full-length protein of PDI1, a partial protein of PDI1, or a mutant protein thereof.

PDI1 has a molecular chaperone function, is an enzyme localized to the ER, and plays a role in refolding of proteins in the ER. PDI1 has, in addition to a moiety functions as a molecular chaperone, a moiety functions as a signal for transporting PDI1 synthesized by ribosome (ER targeting signal) to the ER, a moiety functions as a signal for retaining PDI1 in the ER (ER retention signal), or the like.

As described above, it has been known that co-expression of a foreign secretory protein with PDI1 increases the secretory production amount of the secretory protein. This is presumably because an appropriate higher-order structure formation is promoted by the molecular chaperone function of PDI1 when the produced secretory protein passes through the ER. PDI1 is usually retained in the ER by an ER retention signal, but when it is overexpressed, PDI1 is secreted out of a cell.

Figure 1:
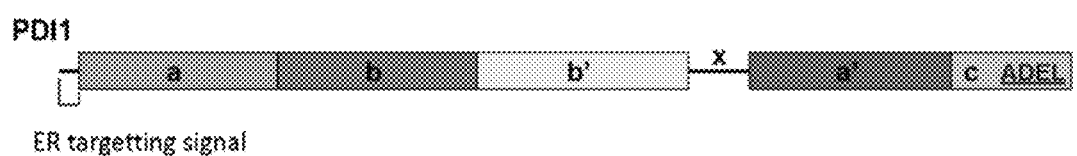
FIG. 1 is a schematic figure showing the structure of PDI1.

PDI1 is an enzyme responsible for in vivo refolding of proteins. FIG. 1 is a schematic figure showing the structure of PDI1. PDI1 is comprised of, from the N-terminal, an ER targeting signal, a-domain, b-domain, b'-domain, x-domain, a'-domain and c-domain containing an ER retention signal (ADEL), in this order. Each of the a-domain and the a'-domain has one active site (CGHC) for molecular chaperone activity. All the four domains a, b, b' and a' form a thioredoxin fold (Cell, vol. 124, pp. 61-73, 2006). Further, in *Saccharomyces cerevisiae*, C-terminal moiety contributes to the enzymatic activity.

Protein (Y) is a protein that contains a moiety (ER targeting signal) functions as a signal for transporting a protein synthesized by ribosome to the ER. In a case where the structural gene encoding a fusion protein prepared by fusing the C-terminal of protein (Y) and other protein is introduced in to a host cell, and then the obtained transformant is cultured, the fusion protein synthesized by ribosome is transported to the ER. Thereafter, as in the case of PDI1 overexpression, the fusion protein in the ER is secreted out of the transformant. In a case where the fusion protein is cleaved between a protein (Y) moiety and a protein (Z) moiety, in inside of the transformant such as the ER, the Golgi apparatus, etc., the protein (Z) moiety produced by the cleavage is secreted out of the transformant. Therefore, the protein (Y) is required to have an ER targeting signal or a moiety having the same function, and when the partial protein or mutant protein of PDI1 is used, such a protein has an ER targeting signal or a moiety having the same function.

On the other hand, since the ER retention signal has a tendency to retain a protein having the signal in the ER and inhibit secretion, secretion of the fusion protein may be inhibited. Therefore, for the secretion of a fusion protein having a protein (Y) moiety and a protein (Z) moiety, the protein (Y) is preferably a partial protein that does not contain any ER retention signal or a mutant protein that does not contain any moiety having the same function as the ER retention signal. Further, in a case where the fusion protein is cleaved into protein (Z) and other protein having a protein (Y) moiety in inside of a cell, since the protein (Z) does not contain any ER retention signal, its secretion is not inhibited. Therefore, in the case of secreting the protein (Z), the protein (Y) may contain an ER retention signal or a moiety having the same function as the ER retention signal.

Since it is presumed that a fusion protein transported to the inside of the ER is converted to an appropriate higher-order structure and that the secretion of the fusion protein or a protein (Z) produced by cleaving the fusion protein is thereby promoted, the protein (Y) preferably retains, at least partially, its molecular chaperone function. Therefore, the protein (Y) preferably contains a-domain, further preferably contains a-domain and b-domain. a'-domain may be contained instead of the a-domain, and b'-domain may be contained instead of the b-domain.

The partial protein of PDI1 is a protein in which at least some region of the full-length PDI1 is missing. For example, it may be a partial protein in which some of the domains of the full-length PDI1 are missing, or a partial protein in which some regions inside of the domains are missing.

As described above, the protein (Y) is required to have an ER targeting signal and preferably has a molecular chaperone function, the protein (Y) preferably contains a-domain. Further, it preferably contains b-domain. Since the ER retention signal is considered to inhibit secretion of a protein, the protein (Y) preferably does not have any ER retention signal, and preferably does not have any c-domain in which an ER retention signal exists.

When the partial protein is represented based on an unit of domain or signal, a partial protein comprised of, from the N-terminal, an ER targeting signal, a-domain and b-domain, in this order (hereinafter referred to as PDI1(ab)), a partial protein comprised of an ER targeting signal, a-domain, b-domain and b'-domain (hereinafter referred to as PDI1(abb')), a partial protein comprised of an ER targeting signal, a-domain, b-domain and x-domain (hereinafter referred to as PDI1(abx)), a partial protein comprised of an ER targeting signal, a-domain, b-domain, b'-domain and x-domain (hereinafter referred to as PDI1(abb'x)), a partial protein which is PDI1 lacking c-domain (hereinafter referred to as PDI1(- c)), and a partial protein of PDI1 lacking an ER retention signal (hereinafter referred to as PDI1(-ADEL)) may, for example, be mentioned.

Each domain or signal in the above-described partial protein may be shorter than the original domain or signal region at its N-terminal side and/or C-terminal side, so long as its function is retained. For example, in the above-described PDI1(ab), the C-terminal side of the b-domain may be shorter than the original b-domain. Further, each of the domains in the above-described partial protein may contain, if domains adjacent to the original of each domain do not exist, a part of such missing adjacent domain regions (provided that functions of such adjacent domains are lost, as described below). For example, in the above-described PDI1(ab), the C-terminal side of the b-domain may extend to the b'-domain side and contain a part of the N-terminal side of the b'-domain. Likewise, in PDI1(abx), a part of the b'-domain may exist between the b-domain and the x-domain.

A partial region of the domain or signal which does not exist in the above-described partial protein may be contained, so long as its function is lost, in the partial protein. For example, in PDI1(-c), a part of the N-terminal side of the c-domain may exist at the C-terminal side of the a'-domain.

The ER targeting signal has a function of transporting synthesized proteins to the ER. Further, the a-domain and the a'-domain are active sites for molecular chaperone function, and carry out a disulfide exchange reaction of substrate proteins (objects of the molecular chaperone function of PDI1). The b-domain and the b'-domain have a function of binding to substrate proteins. The c-domain contributes to the stabilization of the structure of the a'-domain, and indirectly contributes to the molecular chaperone function. Further, the c-domain contains an ER retention signal, and accordingly has a function of retaining synthesized proteins in the ER. For example, whether or not a certain partial protein has the function of a-domain or a'-domain can be determined after directly measuring the molecular chaperone function of the partial protein by carrying out ScRNase assay, Di-E-GSSG assays, etc.

In the present invention, the mutant protein of PDI1 is a mutant protein of the full-length protein of PDI1 or a mutant protein of a partial protein of PDI1. The mutant protein of PDI1 is a protein having substitution, deletion, insertion, and/or addition of one or at least two amino acids. The number of amino acids to be substituted, etc. from the full-length protein or the partial protein is preferably from 1 to 20, more preferably from 1 to 10, further preferably from 1 to 5.

In the present invention, the mutant protein of PDI1 to be used as protein (Y) may have a molecular chaperone function so long as it is one having a function of an ER targeting signal, and may be a mutant protein having lost a molecular chaperone function. The mutant protein having lost a molecular chaperone function may be a mutant protein of the full-length protein of PDI1 or a partial protein comprising at least one of the a-domain and a'-domain in which a cysteine residue (C) in the active site (CGHC) for molecular chaperone activity is substituted by another amino acid, e.g. a serine residue (S).

In the present invention, since the secretory production efficiencies of the protein (Z) and the fusion protein are very high, as the protein (Y), PDI1(abx), PDI1(abb'x), or the mutant protein is preferably used, PDI1(abx) or PDI1(abb'x) is more preferably used, and PDI1(abx) is further preferably used. Further, as described above, each domain in these partial proteins may be shorter or longer than the original domain.

PDI1 as a source of the protein (Y) may be derived from any species so long as the synthesized fusion protein is transported to the ER of the host cell and the fusion protein or its cleavage product i.e. the protein (Z) is secreted out of the cell, and is appropriately selected taking into consideration the species of a host cell introduced with an expression vector. In a case where the expression vector of the present invention is used for an expression system using yeast or filamentous fungus as a host, the source of the protein (Y) is preferably PDI1 derived from yeast, filamentous fungus or human, more preferably PDI1 derived from a yeast of the genus *Saccharomyces*, a yeast of the genus *Schizosaccharomyces*, a yeast of the genus *Kluyveromyces*, a yeast of the genus *Pichia*, a yeast of the genus *Candida*, a filamentous fungus of the genus *Aspergillus*, a filamentous fungus of the genus *Trichoderma*, a filamentous fungus of the genus *Fusarium*, a filamentous fungus of the genus *Penicillium*, or a filamentous fungus of the genus *Acremonium*. As the yeast of the genus *Schizosaccharomyces, S. pombe, Schizosaccharomyces japonicus*, and *Schizosaccharomyces octosporus* may, for example, be mentioned.

The PDI1 derived from yeast or filamentous fungus may, specifically, be PDI1 of *S. pombe* (UniProt (Universal Protein Resource) ID number: Q10057) (SEQ ID NO: 1), PDI1 of *Kluyveromyces marxianus* (UniProt ID number: Q9Y8F3) (SEQ ID NO: 2), PDI1 of *Saccharomyces cerevisiae* (UniProt ID number: P17967) (SEQ ID NO: 3), PDI of *Pichia pastoris* (UniProt ID number: B3VSN1) (SEQ ID NO: 4), PDI of *Candida albicans* (UniProt ID number: C4YSW3) (SEQ ID NO: 5), PDI1 of *Trichoderma reesei* (PRF (Protein Research Foundation) ID number: 2520344A) (SEQ ID NO: 6), and PDIA of *Aspergillus oryzae*, (UniProt ID number: Q00248) (SEQ ID NO: 7).

Figure 2:
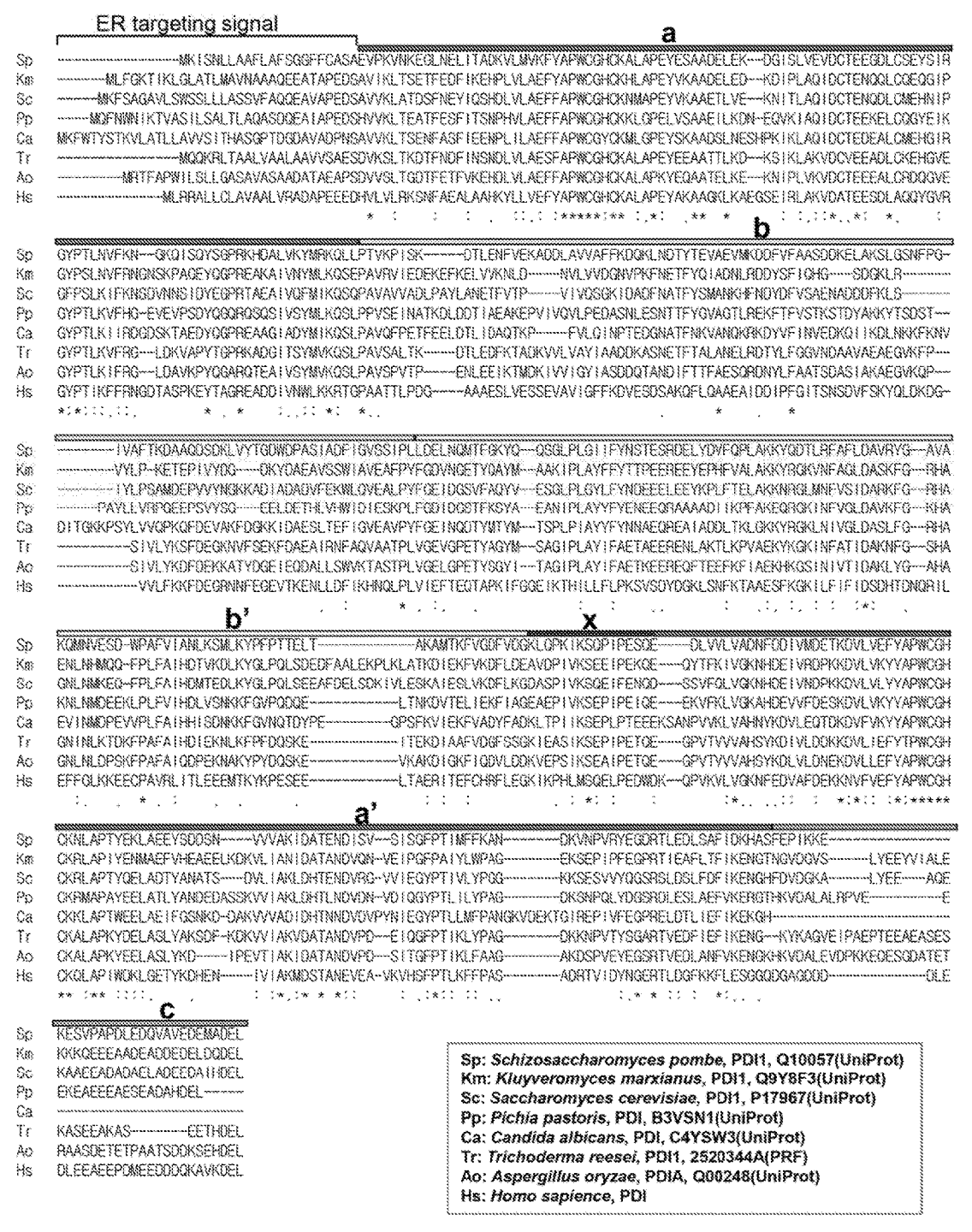

FIG. 2 shows alignment of the amino acid sequences of PDI derived from yeast and filamentous fungus. Further, FIG. 2 also shows the amino acid sequence of PDI derived from human aligned therewith in the same manner. The alignment shown in FIG. 2 was prepared by using a widely-used sequence alignment software ClustalW (employing BLOSUM score matrix as the score matrix). The domain structures of PDI1, as shown in FIG. 1, derived from other species can be determined by using various types of sequence-alignment software and aligning the amino acid sequences of such PDI1 with PDI1 of *S. pombe*.

The protein (Y) may be a protein comprising any one of the following amino acids (1) to (4) and having a function of transporting synthesized fusion proteins that contain a protein (Y) moiety to the ER. (1) Amino acid sequence of SEQ ID NO:1. (2) Amino acid sequence in which one or at least two amino acids are substituted, deleted, inserted, and/or added in the amino acid sequence of SEQ ID NO:1. (3) Amino acid sequence having an identity to the amino acid sequence of SEQ ID NO:1 of at least 30%. (4) Amino acid sequence having a similarity to the amino acid sequence of SEQ ID NO: 1 of at least 70%. (5) Amino acid sequence containing any one of the amino acid sequences (1) to (4).

The amino acid sequence (3) has an identity (homology) to the amino acid sequence of SEQ ID NO: 1 of preferably at least 30%, more preferably at least 35%, further preferably at least 40%, still further preferably at least 60%, even further preferably at least 80%, particularly preferably at least 90%.

The identity (homology) between amino acid sequences can be obtained after aligning two amino acid sequences in a manner to maximize the matching of corresponding amino acids while inserting gaps to positions of insertion and deletion, and then calculating the percentage of amino acids that match with each other based on the entire amino acid sequence while excluding the gaps in the obtained alignment.

The numerical value of the homology percentage is a value obtained by averaging the entire amino acid sequence, and a moiety showing higher or lower value than the numerical value may, partially, be present. For example, domains that are not necessarily required for the function of the protein (Y) may have low homology. The moiety responsible for an essential function (ER targeting signal function) and the moiety responsible for a favorable function (molecular chaperone function, etc.) preferably have high amino acid sequence homologies.

Further, the amino acid sequence (4) has a similarity to the amino acid sequence of SEQ ID NO: 1 of preferably at least 70%, more preferably at least 75%, further preferably at least 80%, still further preferably at least 90%. As in the case of the above (3), a moiety showing higher or lower similarity may be present depending upon its function.

The similarity (sequence similarity) between amino acid sequences can be obtained after aligning two amino acid sequences in a manner to maximize the matching of corresponding amino acids while inserting gaps to positions of insertion and deletion, and then calculating the percentage of chemically similar amino acids that match with each other based on the entire amino acid sequence while excluding the gaps in the obtained alignment.

The identity and similarity between amino acid sequences can be obtained by using various types of homology search software publicly known in the technical field. The homology values of the amino acid sequences of the present invention can be obtained by calculation based on the alignment obtained by a publicly known homology search software ClustalW (employing BLOSUM score matrix as the score matrix).

Here, the chemically similar amino acids are, specifically, the following combinations.
(1) Serine and threonine which are hydrophilic neutral amino acids having a hydroxy group.
(2) Methionine, valine, leucine and isoleucine which are hydrophobic amino acids having a bulky hydrophobic side chain.
(3) Aspartic acid and glutamic acid which are hydrophilic acidic amino acids.
(4) Asparagine and glutamine which are hydrophilic neutral amino acids having a functional group of an amidated carboxy group.
(5) Lysine, arginine and histidine which are hydrophilic basic amino acids.
(6) Phenylalanine, tyrosine and tryptophan which are hydrophobic amino acids having an aromatic ring.
(7) The combination of asparagine and aspartic acid, or glutamine and glutamic acid, which have similar side chain structures.

(Protein (Z))

The expression vector of the present invention contains a structural gene sequence (y) encoding a protein (Y) and a structural gene sequence (z) located downstream from the structural gene sequence (y) and encoding a protein (Z). The protein (Z) is a protein of interest to be produced by using a transformant prepared by introducing the expression vector of the present invention.

The protein (Z) may be a protein intrinsic to a host cell, or a foreign protein heterologous to the host cell such as a protein (heterologous protein) derived from a species other than the host cell. Further, it may be a natural type protein which is intrinsic to any organism, an artificially synthesized protein, or a chimeric protein prepared by fusing two or more types of protein. The protein (Z) is preferably a foreign protein, more preferably a protein produced by multicellular organisms such as animals or plants, further preferably a protein produced by mammals (including human). Further, the protein (Z) may contain various tags including His-tag, FLAG-tag, Myc-tag, GST-tag, etc. which are publicly known in the field of protein expression purification.

In a case where the protein (Z) has a disulfide bond, the protein (Y) preferably has a molecular chaperone function. As compared to the case where the molecular chaperone function of the protein (Y) is lost or reduced, when the molecular chaperone function is retained, the secretory production efficiency of a fusion protein of the proteins (Z) and (Y) or the protein (Z) can be increased further. In a case where the protein (Z) does not have a disulfide bond, presence or absence of a molecular chaperone function in the protein (Y) has little effect on the secretory production efficiency of the fusion protein or the protein (Z).

The structural gene sequence (z) encoding the protein (Z) is bound to the downstream of the structural gene sequence (y) encoding the protein (Y) in a manner such that the structural gene sequence (z) and the structural gene sequence (y) fall in the same reading frame. Thus, the fusion protein containing a protein (Y) moiety and a protein (Z) moiety is expressed by the expression vector of the present invention.

For the recovery of the protein (Z), it is preferred to dispose, in between the structural gene sequence (y) and the structural gene sequence (z), a structural gene sequence (w) encoding a cleavage site (W) that is comprised of an amino acid or a peptide and functions as a site to be cleaved at the N-terminal side of the protein (Z) moiety either in inside or outside of a cell. The structural gene sequence (z), the structural gene sequence (w), and the structural gene sequence (y) are bound in a manner such that they fall in the same reading frame. In this case, the fusion protein synthesized by ribosome is a fusion protein (hereinafter referred to as fusion protein (YWZ)) having a structure wherein the protein (Y), the cleavage site (W) and the protein (Z) are bound in this order. The fusion protein (YWZ) is secreted from the transformant as it is, or secreted after it is processed (cleaved) in the transformant cell for producing the protein (Z). In a case where the fusion protein (YWZ) is processed in the cell to secrete the protein (Z), the fusion protein (YWZ) is processed in the ER or, after it is moved from there, in the Golgi apparatus, and then the protein (Z) produced by such processing is considered to be secreted out of the cell via secretory vesicles.

To ensure that the fusion protein (YWZ) is correctly processed at the N-terminal side of the protein (Z) moiety, i.e. between the cleavage site (W) and the protein (Z) moiety, the C-terminal side of the cleavage site (W) is preferably comprised of specific amino acids or peptides. The cleavage site (W) preferably has a sequence of KR (K: lysine, R: arginine) or a sequence of at least three amino acids having KR as its C-terminal sequence. In the fusion protein (YWZ), R of KR is bound to the N-terminal amino acid of the protein (Z) moiety. The amino acid number for the sequence of at least three amino acids having KR as its C-terminal sequence is not particularly limited, but is preferably at most 20, more preferably at most 10. If the length of the cleavage site (W) is long, the fusion protein (YWZ) becomes large, whereby its intracellular production efficiency is likely to decrease.

In a case where the fusion protein (YWZ) is secreted out of the transformant, the protein (Z) is produced by cutting out the protein (Z) moiety from the secreted fusion protein (YWZ). In order to facilitate production of the protein (Z) from the fusion protein (YWZ), the cleavage site (W) is preferably a site recognized by a protease for the cleavage at the N-terminal side of the protein (Z) moiety of the fusion protein (YWZ). The protease recognizes the cleavage site (W) of the fusion protein (YWZ), and cleaves the C-terminal side (i.e. between the cleavage site (W) and the protein (Z)) of the cleavage site (W).

As specific examples of the above-mentioned protease, enterokinase, Factor Xa may, for example, be mentioned. The enterokinase is a protease that recognizes DDDDK sequence and cleaves the C-terminal side of the peptide moiety, and Factor Xa is a protease that recognizes IEGR sequence and cleaves the C-terminal side of the peptide moiety. The protein (Z) is obtained by applying enterokinase to a fusion protein (YWZ) having a sequence of DDDDK or a sequence comprised of at least six amino acids and has a C-terminal sequence of DDDDK as the cleavage site (W). Likewise, the protein (Z) is obtained by applying Factor Xa to a fusion protein (YWZ) having a sequence of IEGR or a sequence comprised of at least five amino acids and has a C-terminal sequence of IEGR as the cleavage site (W).

The amino acid number of the sequence comprised of at least six amino acids and has a C-terminal sequence of DDDDK or the sequence comprised of at least five amino acids and has a C-terminal sequence of IEGR is not particularly limited, but is preferably at most 20, more preferably at most 10. If the length of the cleavage site (W) is long, the fusion protein (YWZ) becomes large, whereby its intracellular production efficiency is likely to decrease.

(Promoter and Terminator)

The expression vector of the present invention contains a promoter located upstream from a structural gene sequence (y) and a terminator located downstream from a structural gene sequence (z). By the promoter and the terminator, a fusion protein containing a protein (Y) moiety and a protein (Z) moiety is synthesized.

The promoter and the terminator may be ones capable of functioning in a host to direct expression of the above-described fusion protein in the host, and are appropriately selected among publicly known promoters and terminators depending upon the species of the host. The promoter and the terminator to be used in the present invention may be ones intrinsic to the host or ones extrinsic to the host such as a promoter derived from a virus.

When a yeast of the genus *Schizosaccharomyces* is used as the host, as the promoter intrinsic to the yeast of the genus *Schizosaccharomyces*, a promoter of alcohol dehydrogenase gene, a promoter of nmt1 gene which relates to thiamine metabolism, a promoter of fructose 1,6-bisphosphatase gene which relates to glucose metabolism, a promoter of an invertase gene which relates to catabolite repression (WO99/23223) or a promoter of a heat shock protein gene (WO2007/26617) may, for example, be mentioned.

As the promoter capable of functioning in the yeast of the genus *Schizosaccharomyces* and extrinsic thereto, the promoter derived from an animal cell virus disclosed in JP-A-5-15380, JP-A-7-163373 or JP-A-10-234375 may, for example, be mentioned, and hCMV promoter or SV40 promoter is preferred.

As the terminator capable of functioning in the yeast of the genus *Schizosaccharomyces*, the terminator derived from human disclosed in JP-A-5-15380, JP-A-7-163373 or JP-A-10-234375 may, for example, be mentioned, and human lipocortin-I terminator is preferred.

(Vector)

The expression vector of the present invention is a vector comprising an expression cassette containing a structural gene sequence (y), a structural gene sequence (z), and a terminator sequence. Preferably, it is a vector further comprising the above-described structural gene sequence (w) in between the structural gene sequence (y) and the structural gene sequence (z). Further, the expression cassette is a combination of DNA essential for expressing the above-described fusion protein.

The expression cassette preferably contains a 5'-untranslated region located downstream from the promoter sequence and upstream from the structural gene sequence (y). Further, it preferably contains a 3'-untranslated region located downstream from the structural gene sequence (z) and upstream from the terminator sequence. Further, it may contain a stop codon located downstream from the structural gene sequence (z) and upstream from the terminator sequence (when it contains a 3'-untranslated region, upstream from the region).

Further, the expression vector of the present invention may contain only one copy, or two or more copies of the expression cassette.

The vector of the present invention is one prepared by integrating the expression cassette into a vector having a circular DNA structure or a linear DNA structure. The transformant prepared by using the expression vector of the present invention is a transformant in which the above-described expression cassette is maintained in the host cell as an extrachromosomal gene, or a transformant in which the above-described expression cassette is integrated into the chromosomes of the host cell.

In the case of producing the former transformant, the expression vector of the present invention is preferably an expression vector containing a sequence required for replication in the host cell, i.e. Autonomously Replicating Sequence (ARS).

In the case of producing the latter transformant, the expression vector of the present invention is preferably introduced into the host cell as one having a linear DNA structure and no ARS. For example, the expression vector of the present invention may be a vector comprised of linear DNA, or a vector having a circular DNA structure and a restriction enzyme recognition site for cutting it open to linear DNA at the time of its introduction into the host cell. In a case where the expression vector of the present invention has ARS, it can be introduced into the host cell after eliminating the ARS moiety to form a linear DNA structure, or after the ARS moiety is cut open to form a linear DNA structure in which the function of ARS is inactivated.

The expression vector of the present invention preferably has a marker for selecting a transformant. As the selection marker, ura4 gene (auxotrophic complementation marker) and isopropyl malate dehydrogenase gene (leu1 gene) may, for example, be mentioned.

For example, the expression vector of the present invention may be constructed by using a publicly known multiple cloning vector having a cloning site for introducing a foreign structural gene and inserting the structural gene of the above-described fusion protein into the cloning site. Further, it may also be constructed by integrating the above-described expression cassette into a publicly known vector.

The expression vector of the present invention can also be constructed by using a cloning vector comprising an expression cassette containing, instead of the structural gene sequence (z), a cloning site for inserting the structural gene sequence (z). For example, the expression vector of the present invention can be constructed by integrating the structural gene sequence (z) or its partial sequence into the cloning site of the below-described cloning vector. Further, it is also possible to integrate the structural gene sequence (z) into the cloning site along with the structural gene sequence (w).

[Cloning Vector]

The cloning vector of the present invention is characterized by comprising a promoter sequence capable of functioning in a host cell, a structural gene sequence (y) encoding a protein (Y) located downstream from the promoter and regulated by the promoter, a cloning site located downstream from the structural gene sequence (y) for introducing a structural gene, and a terminator sequence capable of functioning in the host cell. The cloning vector of the present invention preferably contains the origin of DNA replication (ori). When constructing an expression vector from a cloning vector, usually, amplification of the expression vector is required, and E. coli is used as a host for the amplification of the expression vector.

The cloning vector of the present invention may further contain a structural gene sequence (w) in between the structural gene sequence (y) and the cloning site. Particularly, it preferably contains a structural gene sequence (w) encoding KR or a peptide comprised of at least three amino acids and has KR at its C-terminal side.

The cloning site contained in the cloning vector of the present invention is a restriction enzyme recognition site exists only in the cloning site of the vector. The cloning site contained in the cloning vector of the present invention may have only one restriction enzyme recognition site, or may be a multiple cloning site having at least two restriction enzyme recognition sites. As the multiple cloning site, a multiple cloning site contained in publicly known multiple cloning vectors can be used as it is, and one prepared by appropriately modifying a publicly known multiple cloning site can also be used.

The cloning vector of the present invention preferably contains a marker for determining whether or not the structural gene sequence (z) of a protein (Z) is introduced into the cloning site. As the marker, lacZ gene and a drug resistance gene capable of functioning in E. coli such as an ampicillin resistance gene may, for example, be mentioned.

The cloning vector for a secretory protein of the present invention may contain a stop codon located downstream from the cloning site and upstream from the terminator sequence (when it contains a 3'-untranslated region, upstream from the region).

As specific methods for constructing the expression vector and the cloning vector of the present invention, publicly known methods can be used. For example, an operation method described in the article [J. Sambrook et al., "Molecular Cloning $2^{nd}$ ed.", Cold Spring Harbor Laboratory Press (1989)]. In addition, they may be constructed by an enzymatic amplification method using PCR, a chemical synthesis, or the like.

[Transformant and its Production Method]

The transformant of the present invention is characterized by having the above-described expression cassette in a chromosome or as an extrachromosomal gene. Having the expression cassette in a chromosome means that the expression cassette is integrated into at least one position on the chromosome of the host cell, and having as an extrachromosomal gene means that an expression vector having the expression cassette is contained in the cell. From the viewpoint of easiness in subculture passage of the transformant, it is preferred to have the expression cassette in a chromosome.

Specifically, the transformant of the present invention is produced by introducing the expression vector of the present invention into a host cell.

(Host)

The host of the transformant of the present may be a cell derived from any species which is usually used as a host for expressing foreign proteins, etc. For example, it may be a prokaryotic cell such as E. coli, an eukaryotic microorganism such as a yeast or filamentous fungus, an animal cell such as a mammalian cell or insect cell, or a plant cell.

The host may be a wild-type cell or a mutant-type cell having one or more mutated genes. The mutant-type is preferably a mutant-type in which one or more genes are deleted or inactivated. As the gene to be deleted or inactivated, at least one selected from the group of genes related to energy metabolism, the group of genes related to protease, the group of genes related to meiosis, the group of genes related to transcription, the group of genes related to growth, division or DNA synthesis of a cell, the group of genes related to protein synthesis, the group of genes related to membrane transport, the group of genes related to cellular structure maintenance, the group of genes related to signal transduction, or the group of genes related to ionic homeostasis may, for example, be mentioned. Preferred one is a wild-type in which at lease one gene selected from the group consisting of, among genes related to protease, genes encoding a serine proteases (serine protease gene family), genes encoding aminopeptidases (aminopeptidase gene family), gene encoding carboxypeptidases (carboxypeptidase gene family), and gene encoding dipeptidases (dipeptidase gene family) is deleted or inactivated. The protein (Z) and the above-described fusion protein exist in the ER, etc. of the host may be degraded by proteases of the host, and may be degraded by proteases, etc. secreted from the host after being secreted out of the cell. By using a host in which one or more genes related to protease are deleted or inactivated, the degradation of the protein (Z) or the above-described fusion protein is likely to be suppressed.

For deletion or inactivation of a specific gene, publicly known methods can be used. Specifically, the Latour system (Nucleic Acids Res. (2006) 34: ell, and WO2007/063919) can be used to delete the gene. Further, the gene can be inactivated by mutating the gene at a certain position by mutant screening using mutagens (Koubo Bunshi Idengaku Jikken-Hou, 1996, Japan Scientific Societies Press), random mutations using PCR (polymerase chain reaction) (PCR Methods Appl., 1992, vol. 2, p. 28-33) and the like.

The position of a specific gene to be deleted or inactivated may be an ORF (open reading frame) region or an expression regulatory sequence region. The particularly preferred method is a method of deleting or inactivating via the PCR-mediated homologous recombination (Yeast, vol. 14, pp. 943-951, 1998) in which an ORF region of a structural gene is substituted by a marker gene.

The deletion or inactivation of genes related to protease may be deletion of the entire genes or inactivation of the genes by partial deletion. The inactivation of genes related to protease means not only partial deletion of the genes but also modification of the genes without deletion. Further, it may be insertion of other genes or DNA into the sequences of the genes related to protease. In either case, the genes related to protease become inactivated by turning them to ones encoding inactive proteins or ones unable to be transcribed or translated. When two or more copies of one type of protease related gene are present in the cell, all of them may be deleted, or some of them may be remained provided that the intracellular activity of the protease encoded by the gene becomes sufficiently low.

As the host, one having a marker for selecting a transformant is preferably used. For example, it is preferred to use a host which essentially requires a specific nutrient factor for growth due to deletion of a gene. When preparing a transformant by using an expression vector for transformation, a transformant lacking the auxotrophy of the host can be obtained by using a vector carrying the deleted gene (auxotrophic complementation marker). It is possible to select the transformant by using the difference in auxotrophy between the host and the transformant.

For example, a yeast of the genus *Schizosaccharomyces* host which has been made auxotrophic for uracil by deletion or inactivation of orotidine 5'-phosphate decarboxylase gene (ura4 gene) is transformed with a vector containing ura4 gene (auxotrophic complementation marker), and transformants carrying the vector are obtained by selecting ones lacking uracil auxotrophy. The gene to be deleted to make an auxotrophic host is not limited to ura4 gene when it is used for selection of a transformant, and may, for example, be isopropyl malate dehydrogenase gene (leu1 gene).

The host to be used in the present invention is preferably an eukaryotic microorganism such as a yeast or a filamentous fungus, and is more preferably a yeast since there is an established culture method and it does not have any endotoxin. Among various yeasts, a yeast of the genus *Schizosaccharomyces* such as *S. pombe* is preferred. The yeast of the genus *Schizosaccharomyces* is known to be similar to higher animals, as compared with other yeasts such as a budding yeast *Saccharomyces cerevisiae*, in view of various properties including cell cycle, chromosome structure, RNA splicing, etc., and its post-translational modifications including acetylation or phosphorylation of proteins, addition of oligosaccharides, etc. are known to be quite similar to those of animal cells (Cell, vol. 45, pp. 781-782, 1986; Nature, vol. 318, pp. 78-80, 1985; The Journal of Cell Biology, vol. 109, pp. 2693-2702, 1989). Therefore, by using a yeast of the genus *Schizosaccharomyces* as a host for producing protein (Z), gene products that are more similar to natural products and equivalent to those of animal cells can be obtained. There are a lot of common points in culture method among various yeasts, and knowledge known in other yeasts can be applied easily. As the yeast of the genus *Schizosaccharomyces* to be used as a host, the above-described one may be mentioned. Among them, *S. pombe* is preferred in view of the availability of various useful mutant strains.

*S. pombe* as the host may be a wild-type strain or a mutant-type strain having one or more genes related to protease are deleted or inactivated. As the genes related to protease which are deleted or inactivated in the mutant-type strain, the following genes may, for example, be mentioned. Metalloproteinase gene family: cdb4 (SPAC23H4.09), mas2 (SPBC18E5.12c), pgp1 (SPCC1259.10), ppp20 (SPAC4F10.02), ppp22 (SPBC14C8.03), ppp51 (SPAC22G7.01c), ppp52 (SPBC18A7.01), ppp53 (SPAP14E8.04), and oma1 (SPAP14E8.04). Serine protease gene family: isp6 (SPAC4A8.04), ppp16 (SPBC1711.12), psp3 (SPAC1006.01), and sxa2 (SPAC1296.03c). Cysteine protease gene family: ppp80 (SPAC19B12.08), pca1 (SPCC1840.04), cut1 (SPCC5E4.04), gpi8 (SPCC11E10.02c), and atg4 (SPAC19B12.08). Aspartic protease gene family: sxa1 (SPAC26A3.01), yps1 (SPCC1795.09), and ppp81 (SPAC25B8.17). Methionine aminopeptidase gene: fma2 (APBC14C8.03).

As the yeast of the genus *Schizosaccharomyces* host in which a gene related to protease is deleted or inactivated, ones disclosed in WO2002/101038, WO2007/015470, etc. may, for example, be used.

(Transformation Method)

The yeast of the genus *Schizosaccharomyces* host is transformed by using the above-described expression vector. As the transformation method, any publicly known transformation method may be used. Such a transformation method may, for example, be a conventional method like a lithium acetate method, electroporation method, spheroplast method, glass-beads method, or the like., and a method disclosed in JP-A-2005-198612. Further, a commercially available yeast transformation kit may be used.

After carrying out transformation, the resulting transformants are usually subjected to selection. The selection may, for example, be carried out as follows. Several transformants are selected as viable colonies in a broth via the above-mentioned auxotrophic marker screening method, the transformants are grown separately in a liquid broth, followed by measuring the amount of protein (Z) or the above-described fusion protein in each culture broth so as to select transformants highly expressing the proteins. The number of vectors and copies of the expression cassette integrated into the chromosomes can be identified by analyzing the genomes of the selected transformants by pulse-field gel electrophoresis.

(Cultivation Method)

The transformant of the present invention may be cultivated in the same manner as a host which is not transformed.

As the culture broth for cultivating the transformant of the present invention, a publicly known culture broth for cultivating cells of the same species as the host may be used so long as it contains carbon sources, nitrogen sources, inorganic salts and the like which the host cell can use, and the host cell can grow in it efficiently. The culture broth may be natural or synthetic.

As the carbon sources, saccharides such as glucose, fructose and sucrose may, for example, be mentioned.

As the nitrogen sources, inorganic acids or inorganic ammonium salts such as ammonia, ammonium chloride, and ammonium acetate, peptone and casamino acid may, for example, be mentioned.

As inorganic salts, magnesium phosphate, magnesium sulfate and sodium chloride may, for example, be mentioned.

Cultivation may be carried out by using a known cultivation method for yeasts such as a shaking cultivation, a stirring cultivation or the like.

The cultivation temperature is preferably from 23 to 37° C. Further, the cultivation time may be set appropriately.

Cultivation may be carried out batch-wise or continuously.

[Method for Producing Protein]

The method for producing a protein of the present invention is comprised of cultivating a transformant (the transformant of the present invention) obtained by introducing the expression vector of the present invention into a host cell and recovering protein (Z) or the above-described fusion protein from a culture broth obtained by cultivation.

The cultivation conditions can be set appropriately taking into consideration the type, etc. of protein (Z) or the above-described fusion protein. For example, at a temperature of from 16 to 42° C., preferably from 25 to 37° C., and a cultivation time of from 8 to 168 hours, preferably from 48 to 96 hours. Either shaking culture or static culture can be employed, and stirring or aeration may be applied if necessary.

In a case where the fusion protein is secreted from the transformant, protein (Z) is produced by cleaving the N-terminal side of a protein (Z) moiety of the fusion protein by means of a protease, etc. The production of protein (Z) from the fusion protein may be carried out by using the fusion protein separated from a culture broth, or may be carried out before the separation from a culture broth. In either case, a cleavage product other than protein (Z) (such as protein (Y)) will be generated from the fusion protein, whereby it is preferred to separate the cleavage product and the protein (Z).

In a case where the transformant is cultivated to separate protein (Z) or the above-described fusion protein from a culture broth, a publicly known protein separation method may be used. For example, after cultivation, a culture supernatant can be recovered from a culture broth containing cells by means of centrifugation, etc. to isolate and purify the fusion protein from the culture supernatant. Further, by repeatedly cultivating the cells separated from the culture supernatant after refeeding them with a culture broth so as to continuously cultivate the transformant, the protein (Z) or the above-described fusion protein may be produced by secretion.

As the isolation and purification method for recovering the fusion protein or the protein (Z) from the culture supernatant, publicly known methods including a method utilizing difference in solubility such as salting out or solvent precipitation, a method utilizing difference in molecular weight such as dialysis, ultrafiltration or gel electrophoresis, a method utilizing difference in electric charge such as ion-exchange chromatography, a method utilizing specific affinity such as affinity chromatography, a method utilizing difference in hydrophobicity such as reverse phase high performance liquid chromatography, and a method utilizing difference in isoelectric point such as isoelectric focusing may be mentioned.

The isolated and purified protein can be identified by a conventional method such as western blotting or activity assay. The structure of the purified protein can be determined by amino acid analysis, amino-terminal analysis, primary structure analysis and the like.

EXAMPLES

Now, the present invention will be described in further detail with reference to Test Examples. However, the present invention is by no means restricted thereto.

Test Example 1

The full-length protein of PDI1 of *S. pombe* was used as protein (Y).
(Construction of Expression Vector)

At first, into the multiple cloning site of publicly known cloning vector pSL6, the structural gene encoding PDI1 of *S. pombe* was inserted to prepare expression vector pPDI1, and separately therefrom, a gene sequence prepared by deleting the stop codon of the structural gene encoding PDI1 of *S. pombe* and adding the restriction enzyme recognition site for AflIII thereto was inserted to prepare gene-fusion vector pPDI1-AflIII.

Specifically, PCR was carried out by using genomic DNA derived from a wild-type strain of *S. pombe* (ARC032 strain, corresponds to ATCC38366, 972h⁻) as a template, a forward primer (SEQ ID NO: 9) comprising the restriction enzyme recognition site for BspHI at the 5' end, and a reverse primer (SEQ ID NO: 10) comprising the restriction enzyme recognition site for SalI at the 5' end, thereby to obtain a PCR product (PDI1 fragment) having the restriction enzyme recognition site for BspHI at the 5' end and the restriction enzyme recognition site for SalI at the 3' end of the whole ORF of PDI1 gene.

The PDI1 fragment was subjected to double digestion with restriction enzymes BspHI and SalI, and pSL6 was subjected to double digestion with restriction enzymes AarI and SalI. Thereafter, both digested products were ligated to each other for transforming *E. coli* DH5α to obtain a plasmid. Thus obtained plasmid was named as pPDI1.

Further, PCR was carried out by using genomic DNA derived from a wild-type strain of *S. pombe* as a template, a forward primer of SEQ ID NO: 9, and a reverse primer (SEQ ID NO: 11) comprising the restriction enzyme recognition sites for KpnI and AflIII at the 5' end, thereby to obtain a PCR product (PDI1-AflIII fragment) having the restriction enzyme recognition site for BspHI at the 5' end and the restriction enzyme recognition sites for KpnI and AflIII at the 3' end of the whole ORF of PDI1 gene in which the stop codon is deleted.

The PDI1-AflIII fragment was subjected to double digestion with restriction enzymes BspHI and KpnI, and pSL6 was subjected to double digestion with restriction enzymes AarI and KpnI. Thereafter, both digested products were ligated to each other for transforming *E. coli* DH5α to obtain a plasmid. Thus obtained plasmid was named as pPDI1-AflIII.

Then, into the multiple cloning site of pPDI1-AflIII, a structural gene encoding human transferrin having a mutation at a N-linked glycosylation site (mutant hTF) was inserted to prepare expression vector pPDI1-hTF comprising a structural gene encoding a fusion protein of *S. pombe* PDI1 and mutant hTF, and in the same manner, expression vector pPDI1-KR-hTF comprising a structural gene encoding a fusion protein of *S. pombe* PDI1 and mutant hTF was prepared separately. Further, expression vector pP3hTF was prepared by inserting a structural gene encoding mutant hTF into the multiple cloning site of pSL6P3. pSL6 is an expression vector comprising a multiple cloning site between hCMV promoter and LPI terminator. Further, pSL6P3 is a secretory expression vector in which a gene encoding P3 secretion signal peptide (SEQ ID NO:8) is located downstream from hCMV promoter and a multiple cloning site is located between the gene and LPI terminator.

Specifically, PCR was carried out by using an artificial gene encoding mutant hTF (SEQ ID NO: 12) as a template, a forward primer (SEQ ID NO: 13) comprising the restriction enzyme recognition site for AflIII at the 5' end, and a reverse primer (SEQ ID NO: 14) comprising the restriction enzyme recognition site for XbaI at the 5' end, thereby to obtain a PCR product (mutant hTF fragment) having the restriction enzyme recognition site for AflIII at the 5' end and the restriction enzyme recognition site for XbaI at the 3' end of the whole ORF of mutant hTF gene.

Each of the mutant hTF fragment and pPDI1-AflIII was subjected to double digestion with restriction enzymes AflIII and XbaI, and then both digested products were ligated to each other for transforming *E. coli* DH5α to obtain a plasmid. Thus obtained plasmid was named as pPDI1-hTF.

Further, PCR was carried out by using an artificial gene encoding mutant hTF as a template, a forward primer (SEQ ID NO: 15) comprising the restriction enzyme recognition site for AflIII and codons encoding a KR peptide sequence at the 5' end, and a reverse primer of SEQ ID NO: 14, thereby to obtain a PCR product (KR-bound mutant hTF fragment) having the restriction enzyme recognition site for AflII and codons encoding a KR peptide sequence at the 5' end and the restriction enzyme recognition site for XbaI at the 3' end of the whole ORF of mutant hTF gene.

Each of the KR-bound mutant hTF fragment, pPDI1-AflII and pSL6P3 was subjected to double digestion with restriction enzymes AflII and XbaI, and then the KR-bound mutant hTF fragment was ligated to pPDI1-AflII or pSL6P3 for transforming E. coli DH5α to obtain plasmids. Thus obtained plasmids were named as pPDI1-KR-hTF and pP3hTF, respectively.

(Host)

In the Test Examples, as the host, A8 strain (genotype: h⁻, leu1-32, ura4-D18, Δpsp3, Δisp6, Δoma1, Δppp16, Δfma2, Δsxa2, Δatg4, Δppp20) prepared by deleting eight protease genes from the leucine-auxotrophic strain ARC001 of S. pombe (genotype: h⁻, leu1-32) (hereinafter referred to as A0 strain) was used. The A8 strain is a strain preliminarily constructed by gene replacement of the target ORF using a gene cassette (refer to WO2007/015470).

(Preparation of Transformant)

A8 strain was cultivated in YES medium (0.5% of yeast extract, 3% of glucose and 0.1 mg/ml of SP supplements) until 0.6×10⁷ cells/ml. The cells were collected and washed, and then suspended by 0.1M lithium acetate solution (pH 5.0) to 1.0×10⁸ cells/ml. Thereafter, to 100 μl of the suspension, 1 μg of each of the above-mentioned expression vectors digested by restriction enzyme NotI was added, and then 260 μl of a 50% (w/v) polyethylene glycol (PEG4000) aqueous solution was added thereto, followed by stirring to cultivate them for 30 minutes at 30° C. After adding 43 μl of DMSO, cultivated further for 5 minutes at 42° C. PEG4000 was removed by centrifugation and then the cells were washed to suspend them in 150 μl of sterile water. The suspension was applied on minimal-agarose medium. Three to five days after cultivation, a transformant was obtained.

The transformant prepared by using pP3hTF was named as P3hTF strain, the transformant prepared by using pP3hTF and pPDI1 was named as P3hTF+PDI1 strain, the transformant prepared by using pPDI1 was named as PDI1 strain, the transformant prepared by using pPDI1-hTF was named as PDI1-hTF, and the transformant prepared by using pPDI1-KR-hTF was named as PDI1-KR-hTF strain.

(Secretory Production of Protein)

Each of the transformants and A8 strain was inoculated on 5 ml of YPD+MES (1% of yeast extract, 1% of peptone, 2% of glucose and 0.3 M of 2-morpholino ethanesulfonic acid-hydrate) medium (pH 6.0), and cultivated for three days at 32° C. The culture broth was centrifuged to collect a culture supernatant, and a TCA (trichloro-acetic acid) solution was added to 4 ml of the collected culture supernatant to a final concentration of 10% (w/w), followed by cooling to collect a precipitate. To the precipitate, 40 μl of a SDS-PAGE sample buffer was added, and incubated for 5 minutes at 95° C. to prepare a sample. 15 μl of the sample (corresponds to 1.5 ml of the culture supernatant) was applied on an acrylamide gel. After carrying out SDS-PAGE, the gel was subjected to CBB staining so as to detect the stained image by using LAS4000 imaging system (manufactured by Fujifilm Corporation). Further, 2.5 μl of the sample (corresponds to 0.25 ml of the culture broth) was applied on an acrylamide gel. After carrying out SDS-PAGE, the gel was transferred to a PVDF membrane and then subjected to western blotting. As a primary antibody for the western blotting, goat polyclonal anti-hTF antibody (CALBIOCHEM, USA) diluted 1:500 was used, and as a secondary antibody, phosphatase-conjugated rabbit anti-goat IgG antiserum (Kirkegaard and Perry Laboratories, Inc. Co., USA) diluted 1:1000 was used. Further, a hTF band (signal specific to hTF) was visualized by an enhanced chemiluminescence (BCIP/NBT Phosphatase Substrate, Kirkegaard and Perry Laboratories, Inc., Ltd., USA) for its detection.

Figure 3:
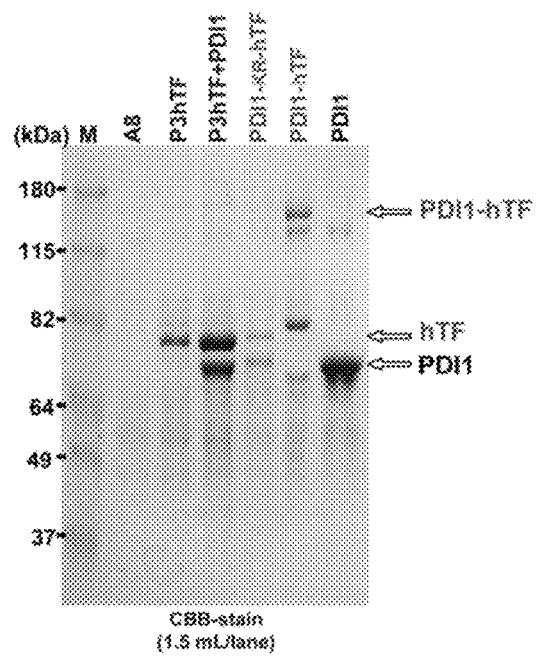
FIG. 3 is a CBB staining image of Test Example 1.
Figure 4:
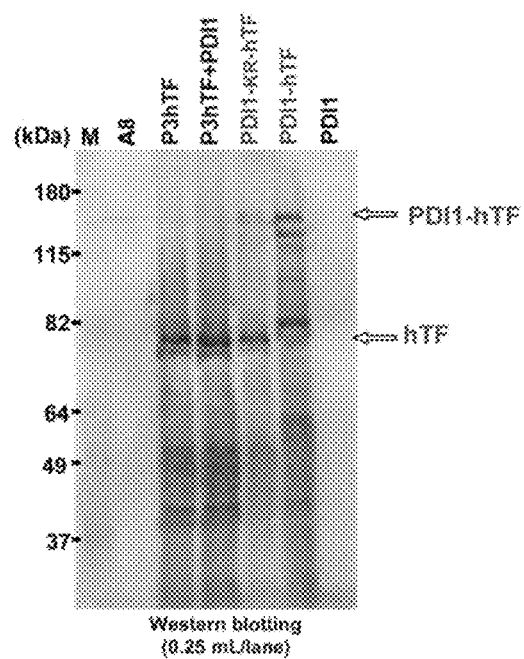
FIG. 4 is a western blotting image of Test Example 1 using an anti-hTF antibody.

The images of CBB staining and western blotting are shown in FIG. 3 and FIG. 4, respectively. Each of "M" in FIGS. 3 and 4 is a molecular weight marker lane. As a result, as shown in FIG. 3, it was confirmed that a large amount of PDI1 was secreted from the PDI1 strain subjected to overexpression. Further, in the case of expressing hTF (P3hTF) in which a publicly known secretion signal peptide P3 is added to the N-terminal, it was confirmed that hTF cleaved from the P3 secretion signal peptide was secreted into a culture broth, and that the secretory production amount of hTF from P3hTF+PDI1 strain subjected to PDI1 co-expression was larger than that of P3hTF strain. Further, it was confirmed from FIG. 3 and FIG. 4 that, also in PDI1-hTF strain, hTF (PDI1-hTF) having PDI1 at its N-terminal was secreted into a culture broth. Further, in the case of PDI1-KR-hTF strain, FIG. 3 shows that bands at a position indicating substantially the same size as P3hTF strain and a position indicating substantially the same size as PDI1 strain were detected, and FIG. 4 shows that a band at a position indicating substantially the same size as P3hTF strain was detected. These results indicate that, in PDI1-KR-hTF strain, hTF is secreted after it is cleaved out from PDI1.

Test Example 2

The secretability of a partial protein of S. pombe PDI1 was examined.

(Construction of Expression Vector)

Into the multiple cloning site of pSL6, the structural gene encoding PDI1(ab) of S. pombe was inserted to prepare expression vector pPDI1(ab), the structural gene encoding PDI1(abx) was inserted to prepare expression vector pPDI1(abx), the structural gene encoding PDI1(abb') was introduced to prepare expression vector pPDI1(abb'), the structural gene encoding PDI1(abb'x) was inserted to prepare expression vector pPDI1(abb'x), the structural gene encoding PDI1(−c) was inserted to prepare expression vector pPDI1(−c), the structural gene encoding PDI1(−x) was inserted to prepare expression vector pPDI1(−x), and the structural gene encoding PDI1(−ADEL) was inserted to prepare expression vector pPDI1(−ADEL), separately. PDI1 (−x) is a partial protein in which x-domain is deleted from the full-length protein of PDI1.

Specifically, PCR was carried out by using pPDI1 as a template, a forward primer of SEQ ID NO: 9, and each of reverse primers of SEQ ID NO: 16 to SEQ ID NO: 20 comprising the restriction enzyme recognition site for KpnI at the 5' end, thereby to obtain each of PCR products (PDI1(ab) fragment, PDI1(abb') fragment, PDI1(abb'x) fragment, PDI1(−c) fragment and PDI1(−ADEL) fragment) having the restriction enzyme recognition site for BspHI at the 5' end and the restriction enzyme recognition site for KpnI at the 3' end of the genes encoding from the $1^{st}$ to the $232^{nd}$ amino acids, to the $339^{th}$ amino acids, to the $354^{th}$ amino acids, to the $462^{nd}$ amino acids, and to the $488^{th}$ amino acids of PDI1, respectively.

Further, PCR was carried out by using pPDI1 as a template, a forward primer of SEQ ID NO: 9, and a reverse primer (SEQ ID NO: 21) comprising the restriction enzyme recognition site for KpnI and a gene encoding the x-domain of PDI1 at the 5' end, thereby to obtain a PCR product (PDI1(abx) fragment) having the restriction enzyme recognition site for BspHI at the 5' end and the restriction enzyme recognition site for KpnI at the 3' end of a structural gene encoding a protein having the x-domain at the C-terminal of from the $1^{st}$ to $232^{nd}$ amino acids of PDI1.

Further, PCR was carried out by using pPDI1 as a template, a forward primer of SEQ ID NO: 9, and a reverse primer (SEQ ID NO: 22) in which the 21 bases of the 3' end of a gene region encoding the b'-domain and the 22 bases of the 5' end of a gene region encoding the a'-domain are overlapped, thereby to obtain a PCR product having the 22 bases of the 5' end of the gene region encoding the a'-domain at the 3' end of a gene encoding from the $1^{st}$ to $339^{th}$ amino acids of PDI1. On the other hand, PCR was carried out by using a forward primer (SEQ ID NO: 23) in which the 21 bases of the 3' end of a gene region encoding the b'-domain and the 22 bases of the 5' end of a gene region encoding the a'-domain are overlapped, and a reverse primer of SEQ ID NO: 20, thereby to obtain a PCR product having the 21 bases of the 3' end of the gene region encoding the b'-domain at the 5' end of a gene encoding from the $354^{th}$ to $488^{th}$ amino acids of PDI1. By using the both PCR products as a template, PCR was carried out with a forward primer of SEQ ID NO: 9 and a reverse primer of SEQ ID NO: 20, thereby to obtain a PCR product (PDI1(-x) fragment) having the restriction enzyme recognition site for BspHI at the 5' end and the restriction enzyme recognition site for KpnI at the 3' end of a structural gene encoding a protein in which amino acid sequences of from the $1^{st}$ to $339^{th}$ amino acids and from the $354^{th}$ to $488^{th}$ amino acids are linked to each other.

Each of the above-described fragments (PDI1(ab) fragment, PDI1(abx) fragment, PDI1(abb') fragment, PDI1(abb'x) fragment, PDI1(-c) fragment, PDI1(-x) fragment, and PDI1(-ADEL) fragment) was subjected to double digestion with restriction enzymes BspHI and KpnI, and pSL6 was subjected to double digestion with restriction enzymes AarI and KpnI. Thereafter, each of the digested fragments was ligated to pSL6 for transforming *E. coli* DH5α to obtain plasmids. Thus obtained plasmids were named as pPDI1(ab), pPDI1(abx), pPDI1(abb'), pPDI1(abb'x), pPDI1(-c), pPDI1(-x) and pPDI1(-ADEL), respectively.

(Preparation of Transformant)

By using the prepared expression vectors and employing A8 strain as a host, transformants were prepared in the same manner as in Test Example 1. The transformant prepared by using pPDI1(ab) was named as PDI1(ab) strain, the transformant prepared by using pPDI1(abx) was named as PDI1(abx) strain, the transformant prepared by using pPDI1(abb') was named as PDI1(abb') strain, the transformant prepared by using pPDI1(abb'x) was named as PDI1(abb'x) strain, the transformant prepared by using pPDI1(-c) was named as PDI1(-c) strain, the transformant prepared by using pPDI1(-x) was named as PDI1(-x) strain, and the transformant prepared by using pPDI1(-ADEL) was named as PDI1(-ADEL) strain.

(Secretory Production of Protein)

In the same manner as in Test Example 1, each of the prepared transformants and PDI1 strain prepared in Test Example 1 was cultivated, and a precipitate was collected by TCA precipitation. To the precipitate, 40 μl of a SDS-PAGE sample buffer was added, and incubated for 5 minutes at 95° C. to prepare a sample. 8 μl of the sample of PDI1 strain (corresponds to 0.8 ml of the culture supernatant) was applied on an acrylamide gel, and for the other transformants, an amount inversely proportional to the molecular weight of PDI expressed in each of the transformants, by using the applied amount of PDI1 strain as a reference, was applied on an acrylamide gel. After carrying out SDS-PAGE, the gel was subjected to CBB staining so as to detect the stained image by using LAS4000 imaging system (manufactured by Fujifilm Corporation). The detected bands of PDI1 were quantified by using a multi gauge image analyzer (manufactured by Fujifilm Corporation), thereby to calculate the relative amount of PDI1 secreted from each transformant, where the amount of PDI1 secreted from PDI1 strain was set as 1.

Figure 5:
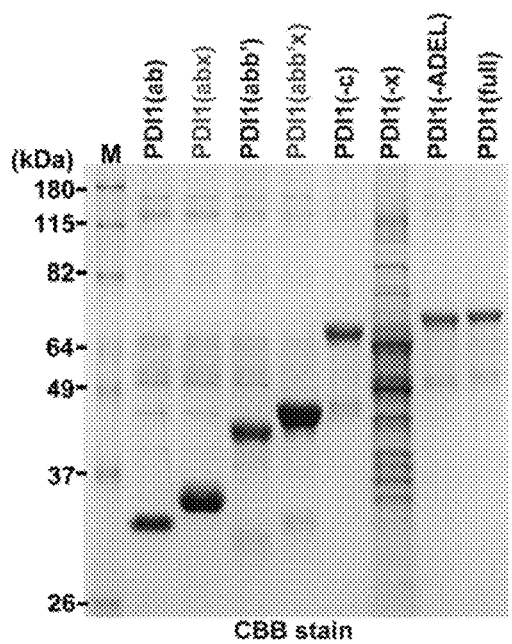
FIG. 5 is a CBB staining image of Test Example 2.
Figure 6:
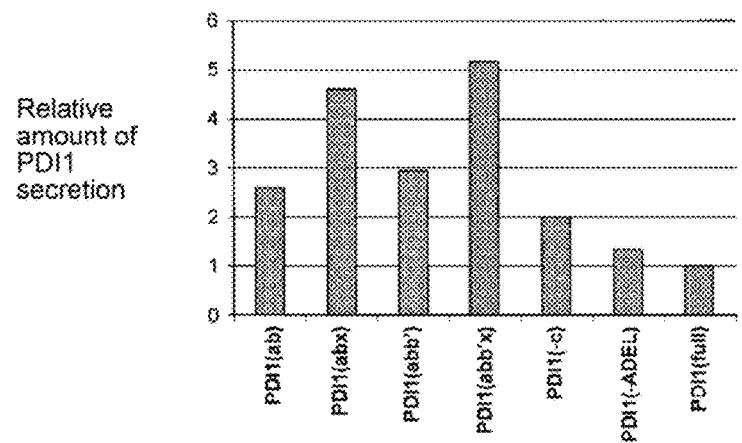
FIG. 6 is a graph showing the relative amount of a full-length or a partial protein of PDI1 secreted from each strain.

FIG. 5 shows the CBB staining image, and FIG. 6 shows the calculation results of the relative amount of the full-length or a partial protein of PDI1 secreted from each of the strains. Each "PDI1(full)" in FIG. 5 and FIG. 6 is a lane to which a sample obtained from PDI1 strain was applied. Further, "M" in FIG. 5 is the same as that of FIG. 3. As a result, the secretion amounts of the partial proteins were found to be larger than that of the full-length PDI1, and it was observed that the secretion amount tends to increase as the molecular weight decreases, except for PDI1(abx) and PDI1(abb'x). The secretion amounts of PDI1(abx) and PDI1(abb'x) were clearly larger than those of the other partial proteins, and the secretion amount of PDI1(abb'x) was the most largest one. In the case of PDI1(-x), though the synthesized proteins were secreted, ladder-shaped bands were detected and the synthesized proteins were found to be severely degraded. These results suggest that the secretion amount increases as the molecular weight of PDI1 decreases, and the x-domain is important for the secretory expression.

Test Example 3

With respect to the secretory production amount of hTF, the case of using PDI1(abb'x) which showed the largest secretory production amount in Test Example 2 as protein (Y) and the case of using P3 secretion signal peptide were compared.

(Construction of Expression Vector)

At first, into the multiple cloning site of pSL6, a gene sequence prepared by deleting the stop codon of the structural gene encoding PDI1(abb'x) of *S. pombe* and adding the restriction enzyme recognition site for AflIII thereto was inserted to prepare gene-fusion vector pPDI1(abb'x)-AflIII.

Specifically, PCR was carried out by using pPDI1(abb'x) as a template, a forward primer of SEQ ID NO: 9, and a reverse primer (SEQ ID NO: 24) comprising the restriction enzyme recognition sites for KpnI and AflIII at the 5' end, thereby to obtain a PCR product (PDI1(abb'x)-AflIII fragment) having the restriction enzyme recognition site for BspHI at the 5' end and the restriction enzyme recognition sites for KpnI and AflIII at the 3' end of a gene fragment encoding PDI1(abb'x) in which the stop codon is deleted.

The PDI1(abb'x)-AflIII fragment was subjected to double digestion with restriction enzymes BspHI and KpnI, and pSL6 was subjected to double digestion with restriction enzymes AarI and KpnI. Thereafter, both digested products were ligated to each other for transforming *E. coli* DH5α to obtain a plasmid. Thus obtained plasmid was named as pPDI1(abb'x)-AflIII.

Then, into the multiple cloning site of pPDI1(abb'x)-AflIII, a structural gene encoding mutant-hTF was inserted to prepare expression vector pPDI1(abb'x)-hTF comprising a structural gene encoding a fusion protein of *S. pombe* PDI1(abb'x) and mutant hTF, and in the same manner, expression vector pPDI1(abb'x)-KR-hTF comprising a structural gene encoding a fusion protein in which *S. pombe* PDI1(abb'x) is bound to mutant hTF via a KR peptide was prepared separately.

Specifically, each of pPDI1-hTF and pPDI1-KR-hTF was subjected to double digestion with restriction enzymes AflII and SalI to collect mutant hTF fragment and KR-bound mutant hTF fragment. On the other hand, pPDI1(abb'x)-AflII was subjected to double digestion with restriction enzymes AflII and SalI, followed by ligating the mutant hTF fragment or KR-bound mutant hTF fragment to pPDI1 (abb'x)-AflII for transforming *E. coli* DH5α to obtain plasmids. Thus obtained plasmids were named as pPDI1(abb'x)-hTF and pPDI1(abb'x)-KR-hTF, respectively.

(Preparation of Transformant)

By using the prepared expression vectors and employing A8 strain as a host, transformants were prepared in the same manner as in Test Example 1. The transformant prepared by using pPDI1(abb'x)-hTF was named as abb'x-hTF strain, and the transformant prepared by using pPDI1(abb'x)-KR-hTF was named as abb'x-KR-hTF strain.

(Secretory Production of Protein)

In the same manner as in Test Example 1, each of the prepared transformants, P3hTF strain and P3hTF+PDI1 strain prepared in Test Example 1, PDI1(abb'x) strain prepared in Test Example 2, and A8 strain was cultivated, and a precipitate was collected by TCA precipitation. To the precipitate, 40 µl of a SDS-PAGE sample buffer was added, and incubated for 5 minutes at 95° C. to prepare a sample. 10 µl of the sample (corresponds to 1 ml of the culture supernatant) was applied on an acrylamide gel. After carrying out SDS-PAGE, in the same manner as in Test Example 2, a CBB staining image was obtained. Thereafter, each band was quantified to calculate a relative amount of hTF secreted from each transformant, where the amount of hTF secreted from P3hTF strain was set as 1. For the case of abb'x-hTF strain, since the secretion amount of the full-length fusion protein was small, hTF obtained by degradation of the fusion protein was used for calculating the relative amount of secretion.

Figure 7:
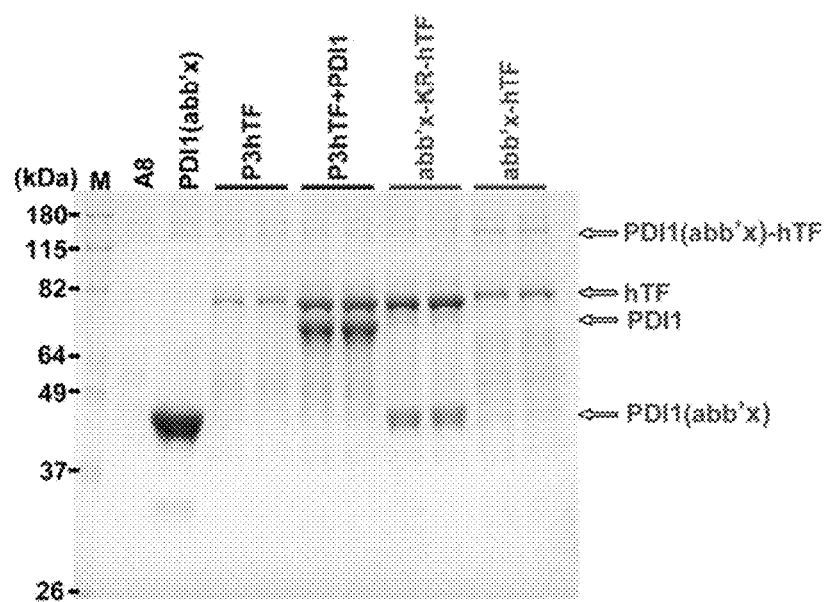
FIG. 7 is a CBB staining image of Test Example 3.
Figure 8:
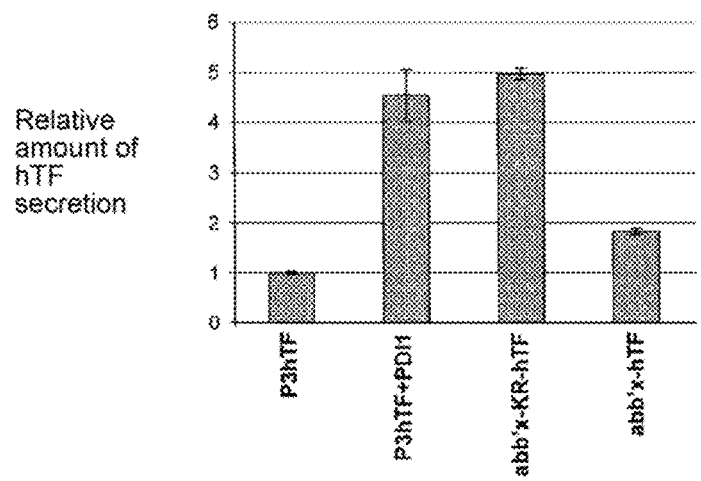
FIG. 8 is a graph showing the relative amount of hTF secreted from each strain in Test Example 3.

FIG. 7 shows the CBB staining image, and FIG. 8 shows the calculation results of the relative amount of hTF secreted from each of the strains. "M" in FIG. 7 is the same as that of FIG. 3. As a result, either abb'x-hTF strain or abb'x-KR-hTF strain showed an amount of hTF secretion larger than P3hTF strain, and was found to have higher secretory production efficiency by having PDI1(abb'x) at the N-terminal, comparing to the case of using P3 secretion signal peptide. In particular, the amount of hTF secretion in abb'x-KR-hTF strain was larger than that of P3hTF-PDI1 strain. However, in abb'x-hTF strain, the amount of the full-length protein of the fusion protein PDI1(abb'x)-hTF was found to be small.

Test Example 4

With respect to the secretory production amount of EGFP, the case of using PDI(abb'x) which showed the largest secretory production amount in Test Example 2 as protein (Y) and the case of using P3 secretion signal peptide were compared.

(Construction of Expression Vector)

Into the multiple cloning site of pPDI1(abb'x)-AflII, a structural gene encoding EGFP was inserted to prepare expression vector pPDI1(abb'x)-EGFP comprising a structural gene encoding a fusion protein of *S. pombe* PDI1 (abb'x) and EGFP, and in the same manner, expression vector pPDI1(abb'x)-KR-EGFP comprising a structural gene encoding a fusion protein in which *S. pombe* PDI1(abb'x) is bound to EGFP via a KR peptide was prepared separately.

Specifically, PCR was carried out by using an artificial gene encoding EGFP (SEQ ID NO: 25) as a template, a forward primer (SEQ ID NO: 26) comprising the restriction enzyme recognition site for AflII at the 5' end, and a reverse primer (SEQ ID NO: 27) comprising the restriction enzyme recognition site for KpnI at the 5' end, thereby to obtain a PCR product (EGFP fragment) having the restriction enzyme recognition site for AflII at the 5' end and the restriction enzyme recognition site for KpnI at the 3' end of the whole ORF of EGFP gene.

Each of the EGFP fragment and pPDI1(abb'x)-AflII was subjected to double digestion with restriction enzymes AflII and KpnI, and then both digested products were ligated to each other for transforming *E. coli* DH5α to obtain a plasmid. Thus obtained plasmid was named as pPDI1-EGFP.

Further, PCR was carried out by using an artificial gene encoding EGFP as a template, a forward primer (SEQ ID NO: 28) comprising the restriction enzyme recognition site for AflII and codons encoding a KR peptide sequence at the 5' end, and a reverse primer of SEQ ID NO: 27, thereby to obtain a PCR product (KR-bound EGFP fragment) having the restriction enzyme recognition site for AflII and codons encoding a KR peptide sequence at the 5' end and the restriction enzyme recognition site for KpnI at the 3' end of the whole ORF of EGFP gene.

Each of the KR-bound EGFP fragment, pPDI1(abb'x)-AflII and pSL6P3 was subjected to double digestion with restriction enzymes AflII and KpnI, and then the KR-bound EGFP fragment was ligated to pPDI1-AflII or pSL6P3 for transforming *E. coli* DH5α to obtain plasmids. Thus obtained plasmids were named as pPDI1(abb'x)-KR-hTF and pP3EGFP, respectively.

(Preparation of Transformant)

By using the prepared expression vectors and employing A8 strain as a host, transformants were prepared in the same manner as in Test Example 1. The transformant prepared by using pP3EGFP was named as P3EGFP strain, the transformant prepared by using pP3EGFP and pPDI1 was named as P3EGFP+PDI1 strain, the transformant prepared by using pPDI1(abb'x)-EGFP was named as abb'x-EGFP strain, and the transformant prepared by using pPDI1(abb'x)-KR-EGFP was named as abb'x-KR-EGFP strain.

(Secretory Production of Protein)

In the same manner as in Test Example 1, each of the prepared transformants, PDI1(abb'x) strain prepared in Test Example 2, and A8 strain was cultivated, and a precipitate was collected by TCA precipitation. To the precipitate, 40 µl of a SDS-PAGE sample buffer was added, and incubated for 5 minutes at 95° C. to prepare a sample. 10 µl of the sample (corresponds to 1 ml of the culture supernatant) was applied on an acrylamide gel. After carrying out SDS-PAGE, in the same manner as in Test Example 2, a CBB staining image was obtained. Thereafter, each band was quantified to calculate a relative amount of EGFP secreted from each transformant, where the amount of EGFP (including a fusion protein) secreted from P3EGFP strain was set as 1.

Figure 9:
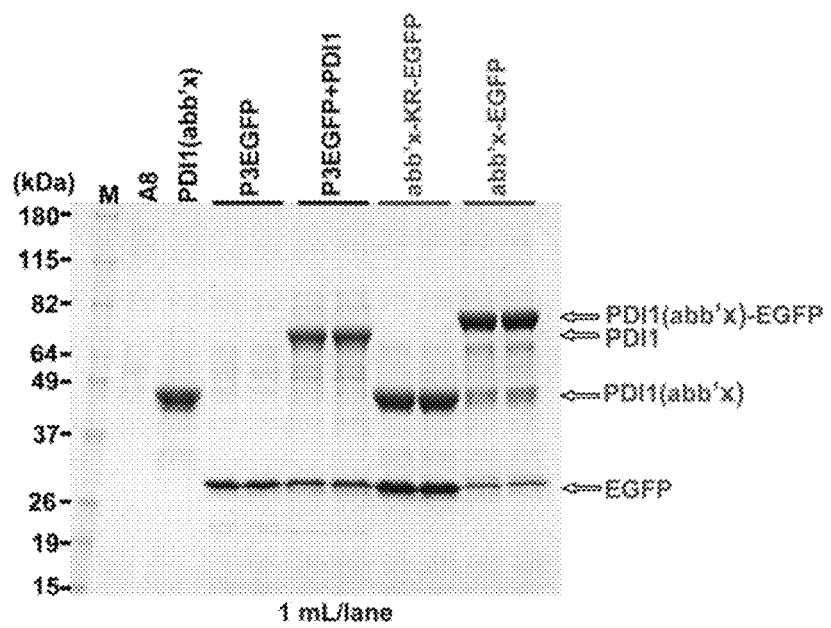
FIG. 9 is a CBB staining image of Test Example 4.
Figure 10:
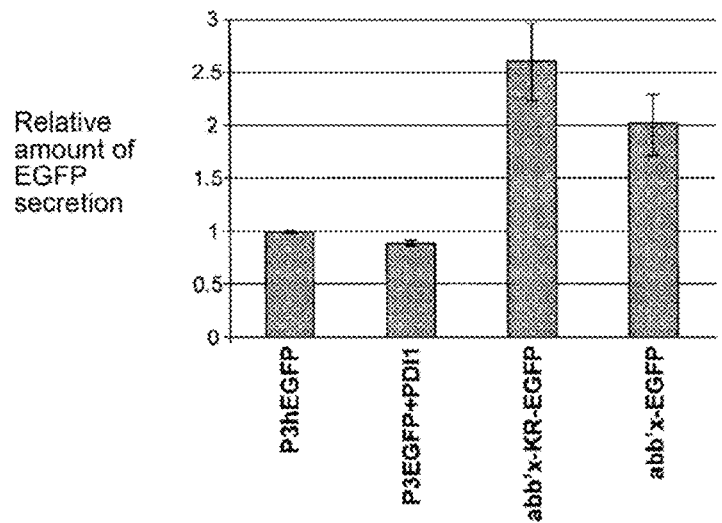
FIG. 10 is a graph showing the relative amount of EGFP (including a fusion protein) secreted from each strain in Test Example 4.

FIG. 9 shows the CBB staining image, and FIG. 10 shows the calculation results of the relative amount of EGFP secreted from each of the strains. "M" in FIG. 9 is the same as that of FIG. 3. As a result, either abb'x-EGFP strain or abb'x-KR-EGFP strain showed an amount of EGFP secretion larger than P3EGFP strain, and was found to have higher secretory production efficiency by having PDI1(abb'x) at the N-terminal, comparing to the case of using P3 secretion signal peptide. Further, since EGFP does not contain a disulfide bond, co-expression with PDI1 did not increase the secretion amount.

Test Example 5

By using *S. pombe* A0 strain as a host, with respect to the secretory production amounts of hTF and EGFP, the case of using PDI(abb'x) which showed the largest secretory production amount in Test Example 2 as protein (Y) and the case of using P3 secretion signal peptide were compared.
(Preparation of Transformant)

By employing A0 strain as a host, transformants were prepared in the same manner as in Test Example 1, by using expression vectors pP3hTF, pPDI1(abb'x)-KR-hTF, pP3EGFP, pPDI1(abb'x)-KR-EGFP, pPDI1(abb'x) and pPDI1 prepared in Test Examples 1 to 4.
(Secretory Production of Protein)

In the same manner as in Test Example 1, each of the prepared transformants, and A0 strain was cultivated, and a precipitate was collected by TCA precipitation. To the precipitate, 40 μl of a SDS-PAGE sample buffer was added, and incubated for 5 minutes at 95° C. to prepare a sample. 10 μl of the sample (corresponds to 1 ml of the culture supernatant) was applied on an acrylamide gel. After carrying out SDS-PAGE, in the same manner as in Test Example 1, a CBB staining image was obtained.

Figure 11:
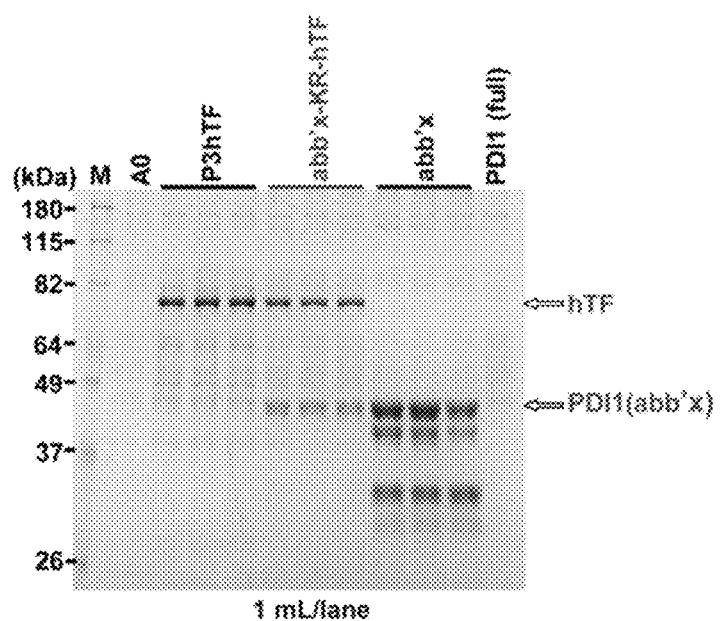
FIG. 11 is a CBB staining image of Test Example 5.
Figure 12:
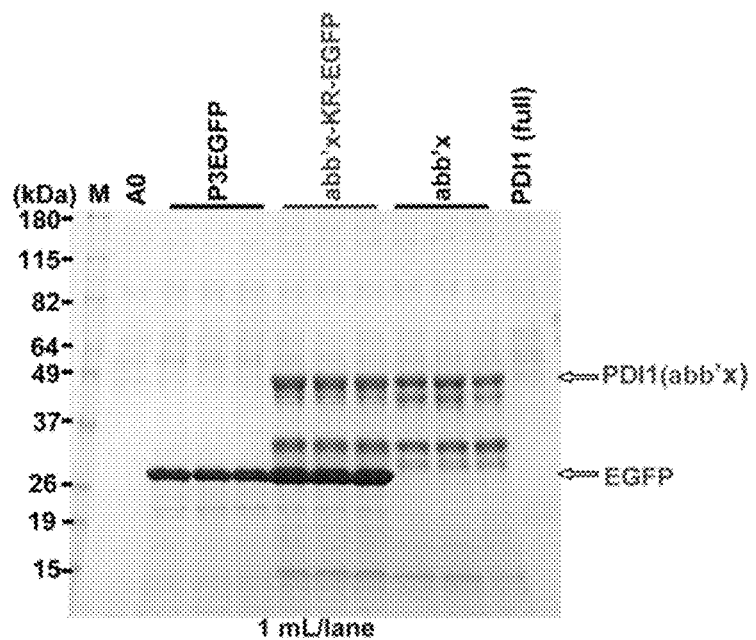
FIG. 12 is a CBB staining image of Test Example 5.

The CBB staining images of A0 strain, P3hTF strain, abb'x-KR-hTF strain, and PDI1(abb'x) strain are shown in FIG. 11, and the CBB staining images of A0 strain, P3EGFP strain, abb'x-KR-EGFP strain, PDI1(abb'x) strain and PDI1 strain are shown in FIG. 12. Each "PDI1 (full)" in FIG. 11 and FIG. 12 is a lane to which a sample obtained from PDI1 strain was applied. Further, "M" is the same as that of FIG. 3. As a result, while secretion of PDI1 from A0 strain was not observed, secretion of PDI1(abb'x) was observed. This is presumably because the full-length protein of PDI1 secreted from A0 was degraded by various protease contained in A0 strain. Further, regarding hTF, unlike A8 strain, the case of using PDI1(abb'x) did not show an increase, as compared with the case of using P3 signal peptide, in the amount of hTF secretion. On the other hand, regarding EGFP, in the same manner as in A8 strain, the case of using PDI1(abb'x) showed an increase, as compared with the case of using P3 signal peptide, in the amount of EGFP secretion, and PDI1 (abb'x) was confirmed to be advantageous in terms of secretory production efficiency.

Test Example 6

With respect to the secretory production amount of hTF, the case of using PDI1(abb'x) as protein (Y) and the case of using PDI1(abx) were compared.
(Construction of Expression Vector)

At first, into the multiple cloning site of pSL6, a gene sequence prepared by deleting the stop codon of the structural gene encoding PDI1(abx) of *S. pombe* and adding the restriction enzyme recognition site for AR thereto was inserted to prepare gene-fusion vector pPDI1(abx)-AflIII.

Specifically, PCR was carried out by using pPDI1(abx) as a template, a forward primer of SEQ ID NO: 9, and a reverse primer (SEQ ID NO: 24), thereby to obtain a PCR product (PDI1(abx)-AflIII fragment) having the restriction enzyme recognition site for BspHI at the 5' end and the restriction enzyme recognition sites for KpnI and AflIII at the 3' end of a gene fragment encoding PDI1(abb'x) in which the stop codon is deleted.

The PDI1(abx)-AflIII fragment was subjected to double digestion with restriction enzymes BspHI and KpnI, and pSL6 was subjected to double digestion with restriction enzymes AarI and KpnI. Thereafter, both digested products were ligated to each other for transforming *E. coli* DH5α to obtain a plasmid. Thus obtained plasmid was named as pPDI1(abx)-AflIII.

Then, into the multiple cloning site of pPDI1(abx)-AflIII, a structural gene encoding mutant-hTF was inserted to prepare expression vector pPDI1(abx)-hTF comprising a structural gene encoding a fusion protein of *S. pombe* PDI1(abx) and mutant hTF, and in the same manner, expression vector pPDI1(abx)-KR-hTF comprising a structural gene encoding a fusion protein in which *S. pombe* PDI1(abx) is bound to mutant hTF via a KR peptide was prepared separately.

Specifically, each of pPDI1-hTF and pPDI1-KR-hTF was subjected to double digestion with restriction enzymes AflIII and SalI to collect mutant hTF fragment and KR-bound mutant hTF fragment. On the other hand, pPDI1(abx)-AflIII was subjected to double digestion with restriction enzymes AflIII and SalI, followed by ligating the mutant hTF fragment or KR-bound mutant hTF fragment to pPDI1(abx)-AflIII for transforming *E. coli* DH5α to obtain plasmids. Thus obtained plasmids were named as pPDI1(abx)-hTF and pPDI1(abx)-KR-hTF, respectively.
(Preparation of Transformant)

By using the prepared expression vectors and employing A8 strain as a host, transformants were prepared in the same manner as in Test Example 1. The transformant prepared by using pPDI1(abx)-hTF was named as abx-hTF strain, and the transformant prepared by using pPDI1(abx)-KR-hTF was named as abx-KR-hTF strain.
(Secretory Production of Protein)

In the same manner as in Test Example 1, each of the prepared transformants, PDI1(abb'x) strain and PDI1(abx) strain prepared in Test Example 2, and abb'x-hTF strain and abb'x-KR-hTF strain prepared in Test Example 3 was cultivated, and a precipitate was collected by TCA precipitation. To the precipitate, 40 μl of a SDS-PAGE sample buffer was added, and incubated for 5 minutes at 95° C. to prepare a sample. 10 μl of the sample (corresponds to 1 ml of the culture supernatant) was applied on an acrylamide gel. After carrying out SDS-PAGE, in the same manner as in Test Example 3, a CBB staining image was obtained. Thereafter, each band was quantified to calculate a relative amount of hTF secreted from each transformant, where the amount of hTF secreted from P3hTF strain was set as 1.

Figure 13:
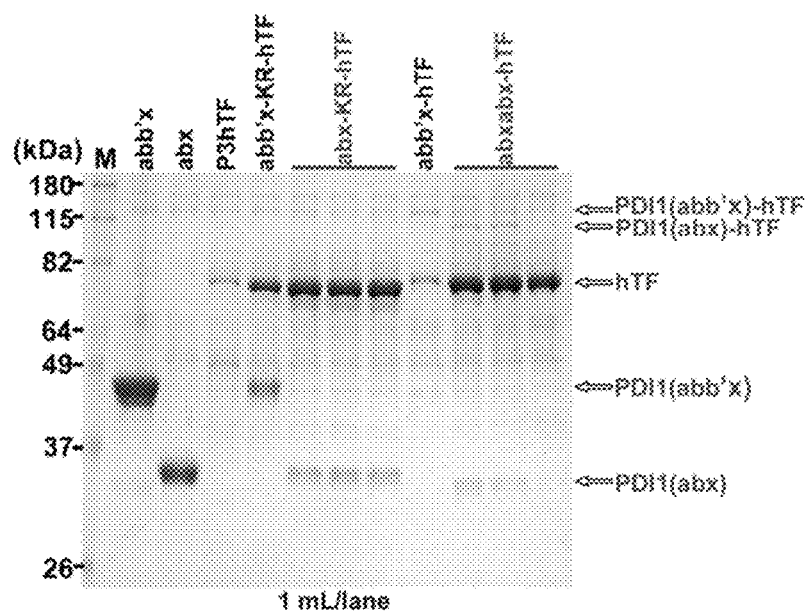
FIG. 13 is a CBB staining image of Test Example 6.
Figure 14:
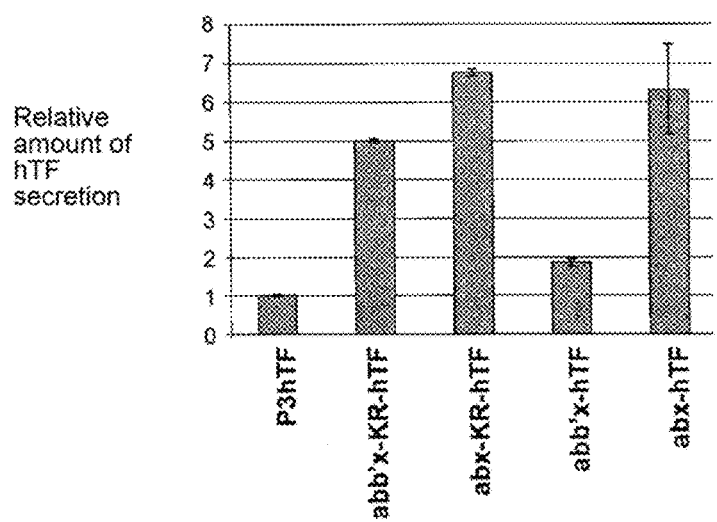
FIG. 14 is a graph showing the relative amount of hTF secreted from each strain in Test Example 6.

FIG. 13 shows the CBB staining image, and FIG. 14 shows the calculation results of the relative amount of hTF secreted from each of the strains. "M" in FIG. 13 is the same as that of FIG. 3. As a result, unlike the cases of PDI1(abb'x) strain and PDI1(abx) strain, abx-KR-hTF strain and abx-hTF strain, both which use PDI1(abx) as protein (Y), showed secretion amounts of hTF larger than abb'x-KR-hTF strain and abb'x-hTF strain, both which use PDI1(abb'x) as protein (Y), respectively. This was presumably attributable to the decrease in the proportion of protein (Y) in the whole the fusion protein.

Test Example 7

With respect to the secretory production amount of hTF, the case of using PDI(abb'x) as protein (Y) and the case of using a protein having a mutation in the active site for molecular chaperone function of PDI1(abb'x) were compared.

(Construction of Expression Vector)

At first, into the multiple cloning site of pSL6, a structural gene encoding mutant protein PDI1(abb'x)(C→S) in which the two cysteine residues (C) of the active site (CGHC) for molecular chaperone activity in the a-domain of *S. pombe* PDI1(abb'x) were substituted by serine residues (S) was inserted to prepare pPDI1(abb'x)(C→S), and separately therefrom, a gene sequence prepared by deleting the stop codon of the structural gene encoding PDI1(abb'x)(C→S) and adding the restriction enzyme recognition site for AflIII thereto was inserted to prepare gene fusion vector pPDI1 (abb'x)(C→S)-AflIII.

Specifically, PCR was carried out by using pPDI1(abb'x) as a template, a forward primer of SEQ ID NO: 9, and a reverse primer of SEQ ID NO: 29 comprising a portion in which codons were mutated for substituting the two cysteine residues (C) of the active site (CGHC) for molecular chaperone activity in the a-domain of *S. pombe* PDI1(abb'x) by serine residues (S), thereby to obtain a PCR product of a partial gene encoding from the $1^{st}$ to $55^{th}$ amino acids of PDI1 while the $51^{st}$ and $54^{th}$ cysteine residues were substituted by serine residues. On the other hand, PCR was carried out by using pPDI1(abb'x) as a template, a forward primer (SEQ ID NO: 30) being complementary to the primer of SEQ ID NO: 29, and a reverse primer of SEQ ID NO: 18, thereby to obtain a PCR product of a partial gene encoding from the $49^{th}$ to $354^{th}$ amino acids of PDI1 while the $51^{st}$ and $54^{th}$ cysteine residues were substituted by serine residues. By using the both PCR products as templates, PCR was carried out with a forward primer of SEQ ID NO: 9 and a reverse primer of SEQ ID NO: 18, thereby to obtain a PCR product (PDI1(abb'x)(C→S) fragment) having the restriction enzyme recognition site for BspHI at the 5' end and the restriction enzyme recognition site for KpnI at the 3' end of a structural gene encoding from the $1^{st}$ to $354^{th}$ amino acids of PDI1 while the $51^{st}$ and $54^{th}$ cysteine residues were substituted by serine residues.

The PDI1(abb'x)(C→S) fragment was subjected to double digestion with restriction enzymes BspHI and KpnI, and pSL6 was subjected to double digestion with restriction enzymes AarI and KpnI. Thereafter, both digested products were ligated to each other for transforming *E. coli* DH5α to obtain a plasmid. Thus obtained plasmid was named as pPDI1(abb'x)(C→S).

Further, PCR was carried out by using pPDI1(abb'x) (C→S) as a template, a forward primer of SEQ ID NO: 9, and a reverse primer of SEQ ID NO: 24, thereby to obtain a PCR product (PDI1(abb'x)(C→S)-AflIII fragment) having the restriction enzyme recognition site for BspHI at the 5' end and the restriction enzyme recognition sites for KpnI and AflIII at the 3' end of a gene fragment encoding PDI1 (abb'x)(C→S) in which the stop codon is deleted.

The PDI1(abb'x)(C→S)-AflIII fragment was subjected to double digestion with restriction enzymes BspHI and KpnI, and pSL6 was subjected to double digestion with restriction enzymes AarI and KpnI. Thereafter, both digested products were ligated to each other for transforming *E. coli* DH5α to obtain a plasmid. Thus obtained plasmid was named as pPDI1(abb'x)(C→S)-AflIII.

Then, into the multiple cloning site of pPDI1(abb'x) (C→S)-AflIII, a structural gene encoding mutant-hTF was inserted to prepare expression vector pPDI1(abb'x)(C→S)-hTF comprising a structural gene encoding a fusion protein of *S. pombe* PDI1(abb'x)(C→S) and mutant hTF, and in the same manner, expression vector pPDI1(abb'x)(C→S)-KR-hTF comprising a structural gene encoding a fusion protein in which *S. pombe* PDI1(abb'x)(C→S) is bound to mutant hTF via a KR peptide was prepared separately.

Specifically, each of pPDI1-hTF and pPDI1-KR-hTF was subjected to double digestion with restriction enzymes AflIII and SalI to collect mutant hTF fragment and KR-bound mutant hTF fragment. On the other hand, pPDI1(abb'x) (C→S)-AflIII was subjected to double digestion with restriction enzymes AflIII and SalI, followed by ligating the mutant hTF fragment or KR-bound mutant hTF fragment to pPDI1 (abb'x)(C→S)-AflIII for transforming *E. coli* DH5α to obtain plasmids. Thus obtained plasmids were named as pPDI1 (abb'x)(C→S)-hTF and pPDI1(abb'x)(C→S)-KR-hTF, respectively.

(Preparation of Transformant)

By using the prepared expression vectors and employing A8 strain as a host, transformants were prepared in the same manner as in Test Example 1. The transformant prepared by using pPDI1(abb'x)(C→S) was named as abb'x(C→S) strain, the transformant prepared by using pPDI1(abb'x) (C→S)-hTF was named as abb'x(C→S)-hTF strain, and the transformant prepared by using pPDI1(abb'x)(C→S)-KR-hTF was named as abb'x(C→S)-KR-hTF strain.

(Secretory Production of Protein)

In the same manner as in Test Example 1, each of the prepared transformants, PDI1(abb'x) strain prepared in Test Example 2, and abb'x-hTF strain and abb'x-KR-hTF strain prepared in Test Example 3 was cultivated, and a precipitate was collected by TCA precipitation. To the precipitate, 40 μl of a SDS-PAGE sample buffer was added, and incubated for 5 minutes at 95° C. to prepare a sample. 10 μl of the sample (corresponds to 1 ml of the culture supernatant) was applied on an acrylamide gel. After carrying out SDS-PAGE, in the same manner as in Test Example 3, a CBB staining image was obtained. Thereafter, each band was quantified to calculate a relative amount of hTF secreted from each transformant, where the amount of hTF secreted from P3hTF strain was set as 1.

Figure 15:
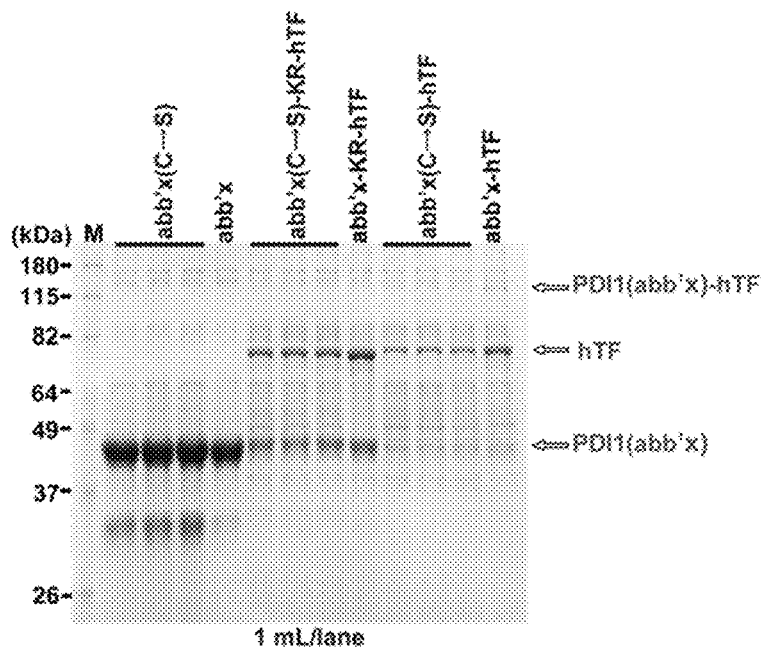
FIG. 15 is a CBB staining image of Test Example 7.
Figure 16:
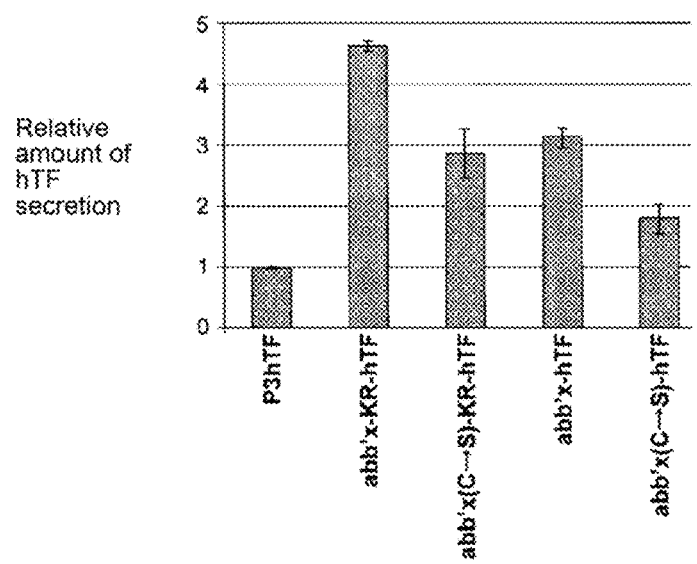
FIG. 16 is a graph showing the relative amount of hTF secreted from each strain in Test Example 7.

FIG. 15 shows the CBB staining image, and FIG. 16 shows the calculation results of the relative amount of hTF secreted from each of the strains. "M" in FIG. 15 is the same as that of FIG. 3. As a result, in PDI1(abb'x)(C→S) strain, PDI1(abb'x) (C→S) was secreted like PDI1(abb'x). abb'x (C→S)-hTF strain and abb'x(C→S)-KR-hTF strain, both which use PDI1(abx)(C→S) as protein (Y), showed secretion amounts of hTF 30 to 40% lower than abb'x-hTF strain and abb'x-KR-hTF strain, both which use PDI1(abb'x) as protein (Y), respectively.

Test Example 8

With respect to the secretory production amount of EGFP, the case of using PDI(abb'x) as protein (Y) and the case of using a protein having a mutation in the active site for molecular chaperone function of PDI1(abb'x) were compared.

(Construction of Expression Vector)

Into the multiple cloning site of pPDI1(abb'x)(C→S)-AflIII, a structural gene encoding EGFP was inserted to prepare expression vector pPDI1(abb'x)(C→S)-EGFP comprising a structural gene encoding a fusion protein of *S. pombe* PDI1(abb'x)(C→S) and EGFP, and in the same manner, expression vector pPDI1(abb'x)(C→S)-KR-EGFP comprising a structural gene encoding a fusion protein in which *S. pombe* PDI1(abb'x)(C→S) is bound to EGFP via a KR peptide was prepared separately.

Specifically, each of pPDI1(abb'x)-EGFP and pPDI1 (abb'x)-KR-EGFP was subjected to double digestion with restriction enzymes AflIII and SalI to collect EGFP fragment and KR-bound EGFP fragment. On the other hand, pPDI1 (abb'x)(C→S)-AflIII was subjected to double digestion with restriction enzymes AflIII and SalI, followed by ligating the mutant hTF fragment or KR-bound mutant hTF fragment to pPDI1(abb'x)(C→S)-AflIII for transforming E. coli DH5α to obtain plasmids. Thus obtained plasmids were named as pPDI1(abb'x)(C→S)-EGFP and pPDI1(abb'x)(C→S)-KR-EGFP, respectively.

(Preparation of Transformant)

By using the prepared expression vectors and employing A8 strain as a host, transformants were prepared in the same manner as in Test Example 1. The transformant prepared by using pPDI1(abb'x)(C→S)-EGFP was named as abb'x (C→S)-EGFP strain, and the transformant prepared by using pPDI1(abb'x)(C→S)-KR-EGFP was named as abb'x(C→S)-KR-EGFP strain.

(Secretory Production of Protein)

In the same manner as in Test Example 1, each of the prepared transformants, PDI1(abb'x) strain prepared in Test Example 2, and abb'x-EGFP strain and abb'x-KR-EGFP strain prepared in Test Example 4 was cultivated, and a precipitate was collected by TCA precipitation. To the precipitate, 40 μl of a SDS-PAGE sample buffer was added, and incubated for 5 minutes at 95° C. to prepare a sample. 10 μl of the sample (corresponds to 1 ml of the culture supernatant) was applied on an acrylamide gel. After carrying out SDS-PAGE, in the same manner as in Test Example 4, a CBB staining image was obtained.

Figure 17:
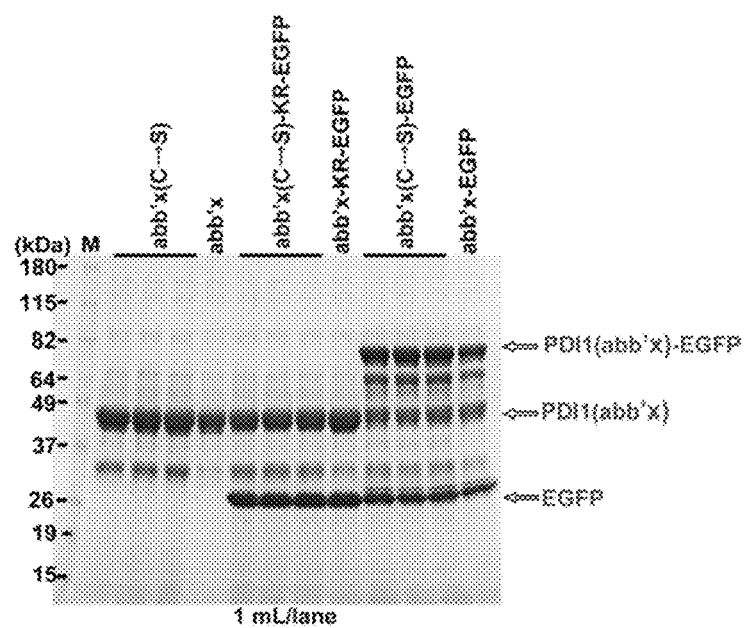
FIG. 17 is a CBB staining image of Test Example 8.

FIG. 17 shows the CBB staining image. "M" in FIG. 17 is the same as that of FIG. 3. As a result, unlike the case of hTF, almost no difference in the amount of EGFP secretion was observed between a strain of using PDI1(abb'x)(C→S) as protein (Y) and a strain of using PDI1(abb'x). This is presumably because EGPF itself does not benefit from the molecular chaperone function of PDI1, unlike hTF.

Test Example 9

Whether or not PDI1(abb'x) has, like the full-length protein, a molecular chaperone activity was examined.

(Preparation of Transformant)

In the same manner as in Test Example 1, by employing A8 strain as a host, P3hTF+PDI1(abb'x) strain was prepared by using pP3hTF and pPDI1(abb'x), and P3hTF+PDI1 (abb'x)(C→S) strain was prepared by using pP3hTF and pPDI1(abb'x)(C→S).

(Secretory Production of Protein)

In the same manner as in Test Example 1, each of the prepared transformants, P3hTF strain prepared in Test Example 1, PDI1(abb'x) strain prepared in Test Example 2, PDI1(abb'x)-hTF strain and PDI1(abb'x)-KR-hTF strain prepared in Test Example 3, and A8 strain was cultivated, and a precipitate was collected by TCA precipitation. To the precipitate, 40 μl of a SDS-PAGE sample buffer was added, and incubated for 5 minutes at 95° C. to prepare a sample. 10 μl of the sample (corresponds to 1 ml of the culture supernatant) was applied on an acrylamide gel. After carrying out SDS-PAGE, in the same manner as in Test Example 3, a CBB staining image was obtained. Thereafter, each band was quantified to calculate a relative amount of hTF secreted from each transformant, where the amount of hTF secreted from P3hTF strain was set as 1.

Figure 18:
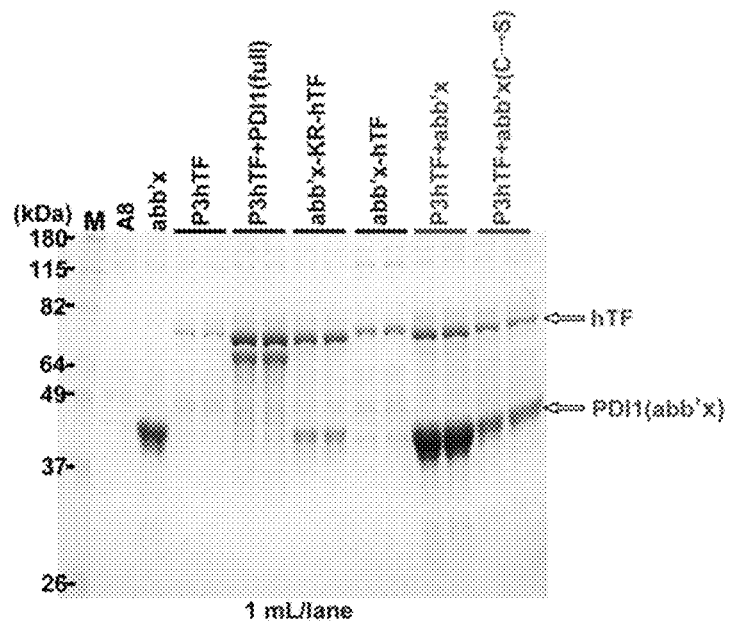
FIG. 18 is a CBB staining image of Test Example 9.
Figure 19:
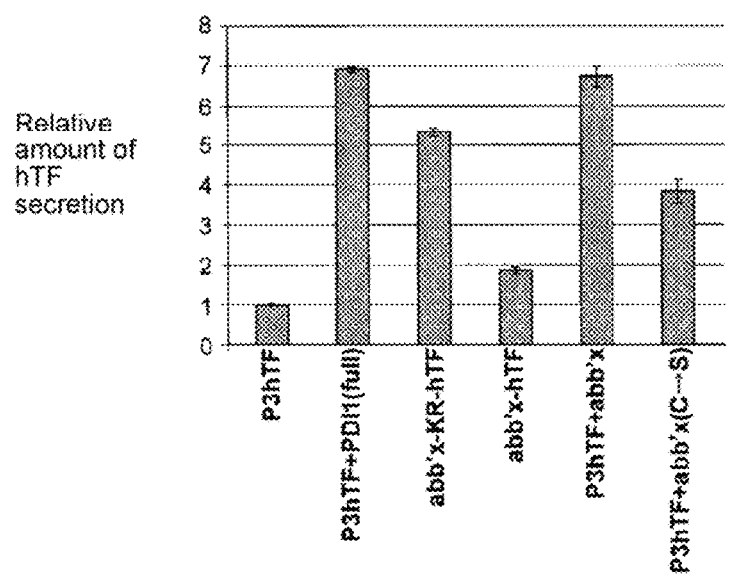
FIG. 19 is a graph showing the relative amount of hTF secreted from each strain in Test Example 9.

FIG. 18 shows the CBB staining image, and FIG. 19 shows the calculation results of the relative amount of hTF secreted from each of the strains. "M" in FIG. 18 is the same as that of FIG. 3. As a result, the amount of hTF secreted from P3hTF+PDI1(abb'x) strain was found to be increased, like P3hTF+PDI1 strain, and in the case of P3hTF+PDI1 (abb'x)(C→S) strain, the secretion amount was found to be smaller than that of P3hTF+PDI1 strain or P3hTF+PDI1 (abb'x) strain, and the molecular chaperone effect was found to be low. According to these results, PDI1(abb'x) was confirmed to have a chaperone activity, and in a case where protein (Z) itself is a protein benefits from the PDI1 co-expression, it was suggested that PDI1(abb'x) fused to the N-terminal side of the protein may also function as a molecular chaperone.

Test Example 10

With respect to the secretory production amounts of human growth hormone (hGH) and human granulocyte colony stimulating factor (GCSF), the case of using PDI (abb'x) which showed the largest secretory production amount in Test Example 2 as protein (Y) and the case of using P3 secretion signal peptide were compared.

(Construction of Expression Vector)

Into the multiple cloning site of pPDI1(abb'x)-AflIII, a structural gene encoding hGH or GCSF was inserted to prepare expression vectors pPDI1(abb'x)-KR-hGH and pPDI1(abb'x)-KR-GCSF comprising a structural gene encoding a fusion protein in which S. pombe PDI1(abb'x) is bound to hGH or GCSF via a KR peptide. Further, into the multiple cloning site of pSL6P3, a structural gene encoding hGH or GCSF was inserted to prepare expression vectors pP3hGH and pP3GCSF.

Specifically, PCR was carried out by using a gene encoding hGH (SEQ ID NO: 31) as a template, a forward primer (SEQ ID NO: 32) comprising the restriction enzyme recognition site for AflIII and codons encoding a KR peptide sequence at the 5' end, and a reverse primer (SEQ ID NO: 33) comprising the restriction enzyme recognition site for KpnI at the 5' end, thereby to obtain a PCR product (KR-bound hGH fragment) having the restriction enzyme recognition site for AflIII at the 5' end and the restriction enzyme recognition site for KpnI at the 3' end of the whole ORF of hGH gene.

Further, PCR was carried out by using a gene encoding GCSF (SEQ ID NO: 34) as a template, a forward primer (SEQ ID NO: 35) comprising the restriction enzyme recognition site for AflIII and codons encoding a KR peptide sequence at the 5' end, and a reverse primer (SEQ ID NO: 36) comprising the restriction enzyme recognition site for KpnI at the 5' end, thereby to obtain a PCR product (KR-bound GCSF fragment) having the restriction enzyme recognition site for AflIII at the 5' end and the restriction enzyme recognition site for KpnI at the 3' end of the whole ORF of GCSF gene.

Each of KR-bound hGH fragment, KR-bound GCSF fragment, pPDI1(abb'x)-AflIII and pSL6P3 was subjected to double digestion with restriction enzymes AflIII and KpnI, and then KR-bound hGF fragment or KR-bound GCSF fragment was ligated to pPDI1-AflIII or pSL6P3 for transforming E. coli DH5α to obtain plasmids. Thus obtained plasmids were named as pPDI1(abb'x)-KR-hGH, pP3hGF, pPDI1(abb'x)-KR-GCSF, and pP3GCSF, respectively.

(Preparation of Transformant)

By using the prepared expression vectors and employing A8 strain as a host, transformants were prepared in the same manner as in Test Example 1. The transformant prepared by using pPDI1(abb'x)-KR-hGH was named as abb'x-KR-hGH strain, the transformant prepared by using pP3hGH was named as P3hGH strain, the transformant prepared by using pPDI1(abb'x)-KR-GCSF was named as abb'x-KR-GCSF strain, and the transformant prepared by using pP3GCSF was named as P3GCSF strain.

(Secretory Production of Protein)

In the same manner as in Test Example 1, each of the prepared transformants was cultivated, and a precipitate was collected by TCA precipitation. To the precipitate, 40 µl of a SDS-PAGE sample buffer was added, and incubated for 5 minutes at 95° C. to prepare a sample. 10 µl of the sample (corresponds to 1 ml of the culture supernatant) was applied on an acrylamide gel. After carrying out SDS-PAGE, in the same manner as in Test Example 2, a CBB staining image was obtained. Thereafter, each band was quantified to calculate a relative amount target protein (Z) secreted from the each transformant, where the amount of each target protein (Z) secreted from P3 signal secretion strains (P3hGH strain and P3GCSF strain) was set as 1.

Figure 20:
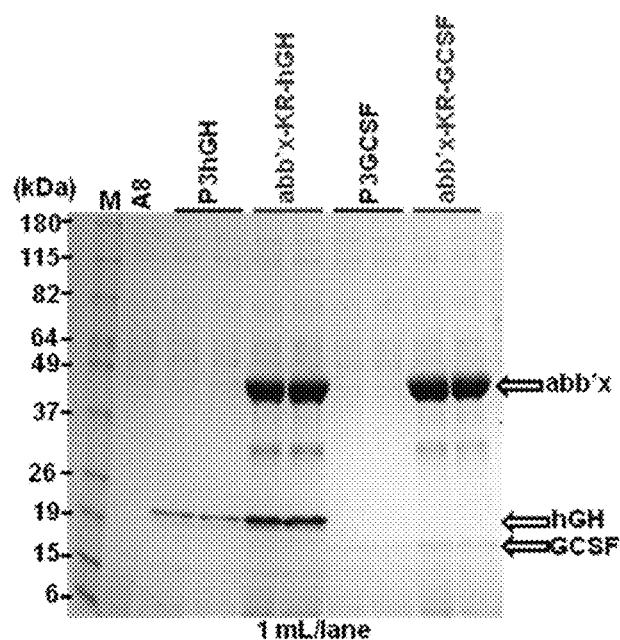
FIG. 20 is a CBB staining image of Test Example 10.
Figure 21:
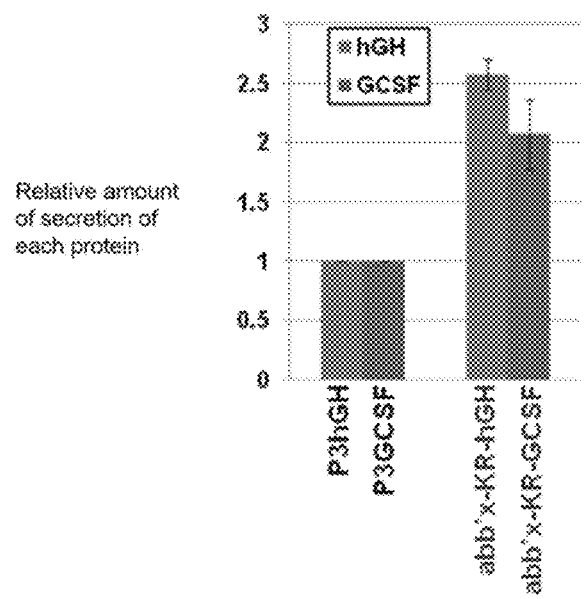
FIG. 21 is a graph showing the relative amount of each protein secreted from each strain in Test Example 10.

FIG. 20 shows the CBB staining image, and FIG. 21 shows the calculation results of the relative amount of each protein secreted from each of the strains. "M" in FIG. 20 is the same as that of FIG. 3. As a result, abb'x-KR-hGH strain and abb'x-KR-GCSF strain showed about two-times increase in the amount of the target protein (Z) secretion comparing to their corresponding P3 signal secretion strains, and their secretory production efficiencies were found to be higher than the cases of using P3 secretion signal peptide by having PDI1(abb'x) at the N-terminal.

Test Example 11

By using S. pombe as a host, the secretability of a partial protein of human-derived PDI1(hPDI) was examined, and the secretion amount was compared with S. pombe-derived PDI1.

(Construction of Expression Vector)

At first, into the multiple cloning site of pSL6, a gene sequence prepared by adding the restriction enzyme recognition site for PvuII to a gene encoding a signal peptide moiety of S. pombe-derived PDI1 was inserted to prepare PDI1 signal peptide addition vector pPDI1(SP)-PvuII.

Specifically, PCR was carried out by using pPDI1 as a template, a forward primer of SEQ ID NO: 9, and a reverse primer (SEQ ID NO: 37) comprising the restriction enzyme recognition sites for KpnI and PvuII at the 5' end, thereby to obtain a PCR product (PDI1(SP)-PvuII fragment) having the restriction enzyme recognition site for BspHI at the 5' end and the restriction enzyme recognition sites for KpnI and PvuII at the 3' end of a gene fragment encoding a signal peptide moiety of PDI1.

The PDI1(SP)-PvuII fragment was subjected to double digestion with restriction enzymes BspHI and KpnI, and pSL6 was subjected to double digestion with restriction enzymes AarI and KpnI. Thereafter, both digested products were ligated to each other for transforming E. coli DH5α to obtain a plasmid. Thus obtained plasmid was named as pPDI1(SP)-PvuII.

Then, into the multiple cloning site of pPDI1(SP)-PvuII, a structural gene encoding hPDI(ab) was inserted to prepare expression vector pPDI1(SP)-hPDI(ab), a structural gene encoding hPDI(abx) was inserted to prepare expression vector pPDI1(SP)-hPDI(abx), a structural gene encoding hPDI(abb') was inserted to prepare expression vector pPDI1(SP)-hPDI(abb'), a structural gene encoding hPDI(abb'x) was inserted to prepare expression vector pPDI1(SP)-hPDI(abb'x), or a structural gene encoding hPDI(abb'xa'c) was inserted to prepare expression vector pPDI1(SP)-hPDI(abb'xa'c), separately.

Specifically, PCR was carried out by using a gene encoding hPDI (SEQ ID NO: 38) as a template, a forward primer (SEQ ID NO: 39) in which cytosine and thymine are added to the 5' end, and each of reverse primers of SEQ ID NO: 40 to SEQ ID NO: 43 comprising the restriction enzyme recognition site for KpnI at the 5' end, thereby to obtain each of PCR products (hPDI(ab) fragment, hPDI(abb') fragment, hPDI(abb'x) fragment, and hPDI(abb'xa'c) fragment) having cytosine and thymine at the 5' end and the restriction enzyme recognition site for KpnI at the 3' end of the genes encoding from the $18^{th}$ to the $236^{th}$ amino acids, to the $349^{th}$ amino acids, to the $364^{th}$ amino acids, and to the $508^{th}$ amino acids of PDI1, respectively.

Further, PCR was carried out by using a gene encoding hPDI as a template, a forward primer of SEQ ID NO: 39, and a reverse primer (SEQ ID NO: 44) comprising the restriction enzyme recognition site for KpnI and a gene encoding the x-domain of hPDI at the 5' end, thereby to obtain a PCR product (hPDI(abx) fragment) having cytosine and thymine at the 5' end and the restriction enzyme recognition site for KpnI at the 3' end of a structural gene encoding a protein having the x-domain at the C-terminal of from the $18^{th}$ to the $236^{th}$ amino acids of hPDI.

Each of the above-described fragments (hPDI(ab) fragment, hPDI1(abx) fragment, hPDI(abb') fragment, hPDI(abb'x) fragment, and hPDI(abb'xa'c) fragment) was subjected to digestion with restriction enzyme KpnI, and pPDI1(SP)-PvuII was subjected to double digestion with restriction enzymes PvuII and KpnI. Thereafter, each of the digested fragments was ligated to pPDI1(SP)-PvuII for transforming E. coli DH5α to obtain plasmids. Thus obtained plasmids were named as pPDI1(SP)-hPDI(ab), pPDI1(SP)-hPDI(abx), pPDI1(SP)-hPDI(abb), pPDI1(SP)-hPDI(abb'x), and pPDI1(SP)-hPDI(abb'xa'c), respectively. These plasmids are comprised of a structural gene encoding a fusion protein of a signal peptide of S. pombe-derived PDI1 and each of the partial proteins of hPDI. The fusion protein is designed so that the signal peptide of S. pombe-derived PDI1 is removed during the secretion process and only the partial protein of hPDI is secreted into a culture broth, when it is expressed in a fission yeast.

(Preparation of Transformant)

By using the prepared expression vectors and employing A8 strain as a host, transformants were prepared in the same manner as in Test Example 1. The transformant prepared by using pPDI1(SP)-hPDI(ab) was named as hPDI(ab) strain, the transformant prepared by using pPDI1(SP)-hPDI(abx) was named as hPDI(abx) strain, the transformant prepared by using pPDI1(SP)-hPDI(abb) was named as hPDI(abb') strain, the transformant prepared by using pPDI1(SP)-hPDI(abb'x) was named as hPDI(abb'x) strain, and the transformant prepared by using pPDI1(SP)-hPDI(abb'xa'c) was named as hPDI(abb'xa'c) strain.

(Secretory Production of Protein)

In the same manner as in Test Example 1, each of the above-prepared transformants, PDI1(ab) strain, PDI1(abx) strain, PDI1(abb') strain and PDI1(abb'x) strain prepared in Test Example 2, and PDI1 strain was cultivated, and a precipitate was collected by TCA precipitation. To the precipitate, 40 µl of a SDS-PAGE sample buffer was added, and incubated for 5 minutes at 95° C. to prepare a sample. 10 µl of the sample of PDI1 strain (corresponds to 1 ml of the culture supernatant) was applied on an acrylamide gel. After carrying out SDS-PAGE, protein bands were visualized by CBB staining.

Figure 22:
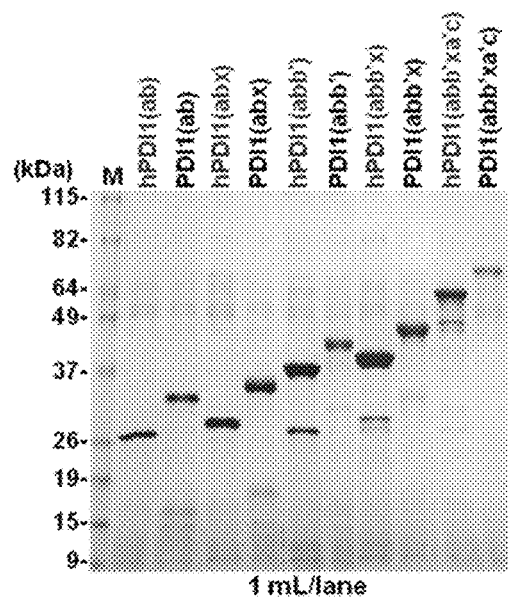
FIG. 22 is a CBB staining image of Test Example 11.

FIG. 22 shows the CBB staining image. "PDI1(abb'xa'c)" in FIG. 22 is a lane to which a sample obtained from PDI1 strain was applied. Further, "M" in FIG. 22 is the same as that of FIG. 3. As a result, within ones having the same partial protein of ab or abx, the secretion amounts of S. pombe-derived PDI1 and hPDI were found to be comparable to each other. Whereas, within ones having the same partial protein of abb', abb'x or abb'xa'c, the secretion amount of hPDI was found to be clearly larger than that of S. pombe-derived PDI1. Further, like S. pombe-derived PDI1, with respect to hPDI, the secretion amounts of partial proteins were found to be large, and among them, the secretion amounts of hPDI(abx) and hPDI(abb'x) were found to be larger than the other partial proteins.

Test Example 12

With respect to the secretory production amount of hTF, the case of using PDI1(abx) or PDI1(abb'x) as protein (Y) and the case of using a fusion protein (PDI1(SP)-hPDI(abx)) of a signal peptide of S. pombe-derived PDI1 and hPDI(abx) or a fusion (PDI1(SP)-hPDI(abb'x)) of a signal peptide of S. pombe-derived PDI1 and hPDI(abb'x) were compared.

(Construction of Expression Vector)

At first, into the multiple cloning site of pSL6, a gene sequence prepared by deleting the stop codon of the structural gene encoding PDI1(SP)-hPDI(abx) or PDI1(SP)-hPDI(abb'x) and adding the restriction enzyme recognition site for AflIII thereto was inserted to prepare gene-fusion vectors pPDI1(SP)-hPDI(abx)-AflIII and pPDI1(SP)-hPDI(abb'x)-AflIII.

Specifically, PCR was carried out by using pPDI1(SP)-hPDI(abx) or pPDI1(SP)-hPDI(abb'x) as a template, a forward primer of SEQ ID NO: 9, and a reverse primer (SEQ ID NO: 45) comprising the restriction enzyme recognition sites for KpnI and AflIII at the 5' end, thereby to obtain each of PCR products (PDI1(SP)-hPDI(abx)-AflIII fragment and PDI1(SP)-hPDI(abb'x)-AflIII fragment) having the restriction enzyme recognition site for BspHI at the 5' end and the restriction enzyme recognition sites for KpnI and AflIII at the 3' end of a gene fragment encoding PDI1 (SP)-hPDI(abx) or PDI1(SP)-hPDI(abb'x) in which the stop codon is deleted.

Each of PDI1(SP)-hPDI(abx)-AflIII fragment and PDI1(SP)-hPDI(abb'x)-AflIII fragment was subjected to double digestion with restriction enzymes BspHI and KpnI, and pSL6 was subjected to double digestion with restriction enzymes AarI and KpnI. Thereafter, both digested products were ligated to each other for transforming E. coli DH5α to obtain plasmids. Thus obtained plasmids were named as pPDI1(SP)-hPDI(abx)-AflIII and pPDI1(SP)-hPDI(abb'x)-AflIII, respectively.

Then, into the multiple cloning sites of pPDI1(SP)-hPDI(abx)-AflIII and pPDI1(SP)-hPDI(abb'x)-AflIII, a structural gene encoding mutant hTF was inserted to prepare expression vectors pPDI1(SP)-hPDI(abx)-hTF and pPDI1(SP)-hPDI(abb'x)-hTF comprising a structural gene encoding a fusion protein of PDI1(SP)-hPDI(abx) or PDI1(SP)-hPDI(abb'x) and mutant hTF, and in the same manner, expression vectors pPDI1(SP)-hPDI(abx)-KR-hTF and pPDI1(SP)-hPDI(abb'x)-KR-hTF comprising a structural gene encoding a fusion protein in which PDI1(SP)-hPDI(abx) or PDI1(SP)-hPDI(abb'x) is bound to mutant hTF via a KR peptide were prepared separately.

Specifically, each of pPDI1-hTF and pPDI1-KR-hTF was subjected to double digestion with restriction enzymes AflIII and SalI to collect mutant hTF fragment and KR-bound mutant hTF fragment. On the other hand, each of pPDI1(SP)-hPDI(abx)-AflIII and pPDI1(SP)-hPDI(abb'x)-AflIII was subjected to double digestion with restriction enzymes AflIII and SalI, followed by ligating the mutant hTF fragment or KR-bound mutant hTF fragment to pPDI1(SP)-hPDI(abx)-AflIII or pPDI1(SP)-hPDI(abb'x)-AflIII for transforming E. coli DH5α to obtain plasmids. Thus obtained plasmids were named as pPDI1(SP)-hPDI(abx)-hTF, pPDI1(SP)-hPDI(abb'x)-hTF, pPDI1(SP)-hPDI(abx)-KR-hTF, and pPDI1(SP)-hPDI(abb'x)-KR-hTF, respectively.

(Preparation of Transformant)

By using the prepared expression vectors and employing A8 strain as a host, transformants were prepared in the same manner as in Test Example 1. The transformant prepared by using pPDI1(SP)-hPDI(abx)-hTF was named as hPDI(abx)-hTF strain, the transformant prepared by using pPDI1(SP)-hPDI(abb'x)-hTF was named as hPDI(abb'x)-hTF strain, the transformant prepared by using pPDI1(SP)-hPDI(abx)-KR-hTF was named as hPDI(abx)-KR-hTF strain, and the transformant prepared by using pPDI1(SP)-hPDI(abb'x)-KR-hTF was named as hPDI(abb'x)-KR-hTF strain.

(Secretory Production of Protein)

In the same manner as in Test Example 1, each of the above-prepared transformants, abb'x-hTF strain and abb'x-KR-hTF strain prepared in Test Example 3, and abx-hTF strain and abx-KR-hTF strain prepared in Test Example 6 was cultivated, and a precipitate was collected by TCA precipitation. To the precipitate, 40 μl of a SDS-PAGE sample buffer was added, and incubated for 5 minutes at 95° C. to prepare a sample. 10 μl of the sample (corresponds to 1 ml of the culture supernatant) was applied on an acrylamide gel. After carrying out SDS-PAGE, in the same manner as in Test Example 3, a CBB staining image was obtained, and then each band was quantified to calculate a relative amount of hTF secreted from each transformant, where the amount of hTF secreted from abx-KR-hTF strain was set as 1.

Figure 23:
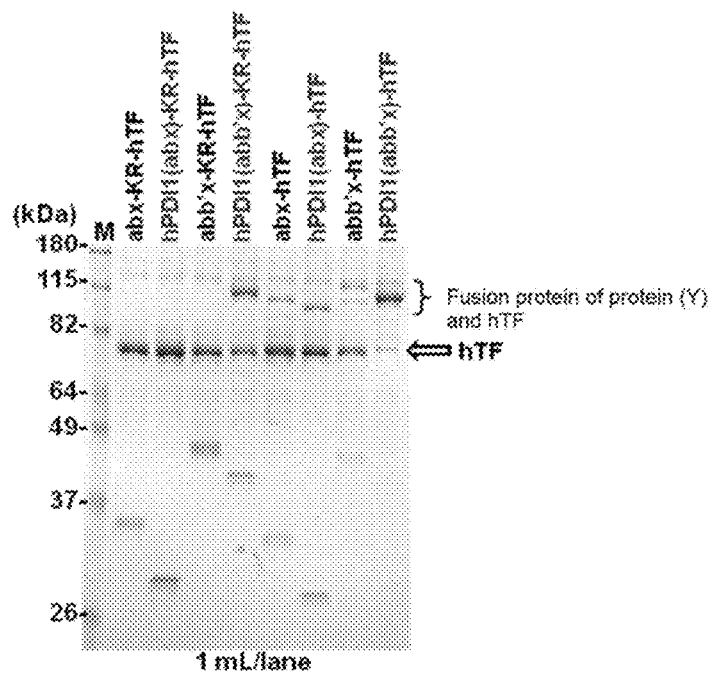
FIG. 23 is a CBB staining image of Test Example 12.
Figure 24:
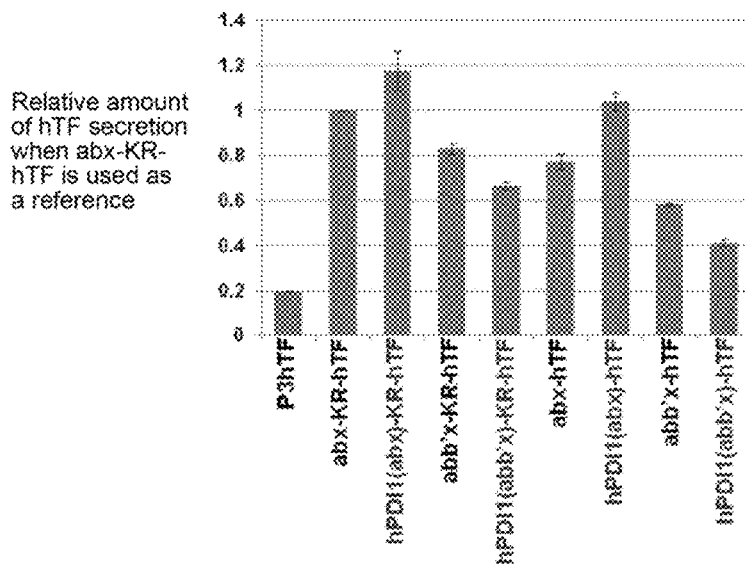
FIG. 24 is a graph showing the relative amount of hTF secreted from each strain in Test Example 12.

FIG. 23 shows the CBB staining image, and FIG. 24 shows the calculation results of the relative amount of hTF secreted from each of the strains. "M" in FIG. 23 is the same as that of FIG. 3. As a result, hPDI(abx)-KR-hTF strain and hPDI(abx)-hTF strain, both which use PDI1(SP)-hPDI(abx) as protein (Y), showed secretion amounts of hTF larger than abx-KR-hTF strain and abx-hTF strain, both which use PDI1(abx) as protein (Y), respectively, and it was found that the secretory production efficiency can be increased further by replacing the S. pombe-derived abx moiety with one derived from human.

In the case of hPDI(abb'x)-hTF strain and hPDI(abb'x)-KR-hTF strain, both which use PDI1(SP)-hPDI(abb'x) as protein (Y), their secretion amounts of hTF were decreased as compared with abb'x-KR-hTF strain and abb'x-hTF strain, both which use PDI1(abb'x) as protein (Y), respectively. Particularly, in hPDI(abb'x)-KR-hTF strain, the separation of protein (Y) and target protein (Z) was insufficient. On the other hand, in hPDI(abb'x)-hTF strain, the secretory production efficiency of the fusion protein of protein (Y) and target protein (Z) was found to be high.

In either case of using PDI1(SP)-hPDI(abx) or PDI1(SP)-hPDI(abb'x) as protein (Y), the secretory production efficiency was found to be higher than the case of using P3 secretion signal peptide.

Test Example 13

With respect to the secretory production amount of EGFP, the case of using PDI1(abx) or PDI1(abb'x) as protein (Y) and the case of using PDI1(SP)-hPDI(abx) or PDI1(SP)-hPDI(abb'x) were compared.

(Construction of Expression Vector)

Into the multiple cloning sites of pPDI1(abx)-AflIII, pPDI1(SP)-hPDI(abx)-AflIII and pPDI1(SP)-hPDI(abb'x)-AflIII, a gene sequence encoding EGFP was inserted to prepare expression vectors pPDI1(abx)-EGFP, pPDI1(SP)-hPDI(abx)-EGFP, and pPDI1(SP)-hPDI(abb'x)-EGFP comprising a structural gene encoding a fusion protein of PDI1(abx), PDI1(SP)-hPDI(abx) or PDI1(SP)-hPDI(abb'x) and EGFP, and in the same manner, expression vectors pPDI1(abx)-KR-EGFP, pPDI1(SP)-hPDI(abx)-KR-EGFP, and pPDI1(SP)-hPDI(abb'x)-KR-EGFP comprising a structural gene encoding a fusion protein in which PDI1(abx), PDI1(SP)-hPDI(abx) or PDI1(SP)-hPDI(abb'x) is bound to EGFP via a KR peptide were prepared separately.

Specifically, each of pPDI1(abb'x)-EGFP and pPDI1(abb'x)-KR-EGFP was subjected to double digestion with restriction enzymes AflIII and SalI to collect EGFP fragment and KR-bound EGFP fragment. On the other hand, each of pPDI1(abx)-AflIII, pPDI1(SP)-hPDI(abx)-AflIII and pPDI1(SP)-hPDI(abb'x)-AflIII was subjected to double digestion with restriction enzymes AflIII and SalI, followed by ligating the EGFP fragment or KR-bound EGFP fragment to pPDI1(abx)-AflIII, pPDI1(SP)-hPDI(abx)-AflIII or pPDI1(SP)-hPDI(abb'x)-AflIII for transforming *E. coli* DH5α to obtain plasmids. Thus obtained plasmids were named as pPDI1(abx)-EGFP, pPDI1(SP)-hPDI(abx)-EGFP, pPDI1(SP)-hPDI(abb'x)-EGFP, pPDI1(abx)-KR-EGFP, pPDI1(SP)-hPDI(abx)-KR-EGFP, and pPDI1(SP)-hPDI(abb'x)-KR-EGFP, respectively.

(Preparation of Transformant)

By using the prepared expression vectors and employing A8 strain as a host, transformants were prepared in the same manner as in Test Example 1. The transformant prepared by using pPDI1(abx)-EGFP was named as abx-EGFP strain, the transformant prepared by using pPDI1(SP)-hPDI(abx)-EGFP was named as hPDI(abx)-EGFP strain, the transformant prepared by using pPDI1(SP)-hPDI(abb'x)-EGFP was named as hPDI(abb'x)-EGFP strain, the transformant prepared by using pPDI1(abx)-KR-EGFP was named as abx-KR-EGFP strain, the transformant prepared by using pPDI1(SP)-hPDI(abx)-KR-EGFP was named as hPDI(abx)-KR-EGFP strain, and the transformant prepared by using pPDI1(SP)-hPDI(abb'x)-KR-EGFP was named as hPDI(abb'x)-KR-EGFP strain.

(Secretory Production of Protein)

In the same manner as in Test Example 1, each of the above-prepared transformants, and abb'x-EGFP strain and abb'x-KR-EGFP strain prepared in Test Example 4 was cultivated, and a precipitate was collected by TCA precipitation. To the precipitate, 40 μl of a SDS-PAGE sample buffer was added, and incubated for 5 minutes at 95° C. to prepare a sample. 10 μl of the sample (corresponds to 1 ml of the culture supernatant) was applied on an acrylamide gel. After carrying out SDS-PAGE, in the same manner as in Test Example 3, a CBB staining image was obtained, and then each band was quantified to calculate a relative amount of EGFP secreted from each transformant, where the amount of EGFP secreted from abx-KR-EGFP strain was set as 1.

Figure 25:
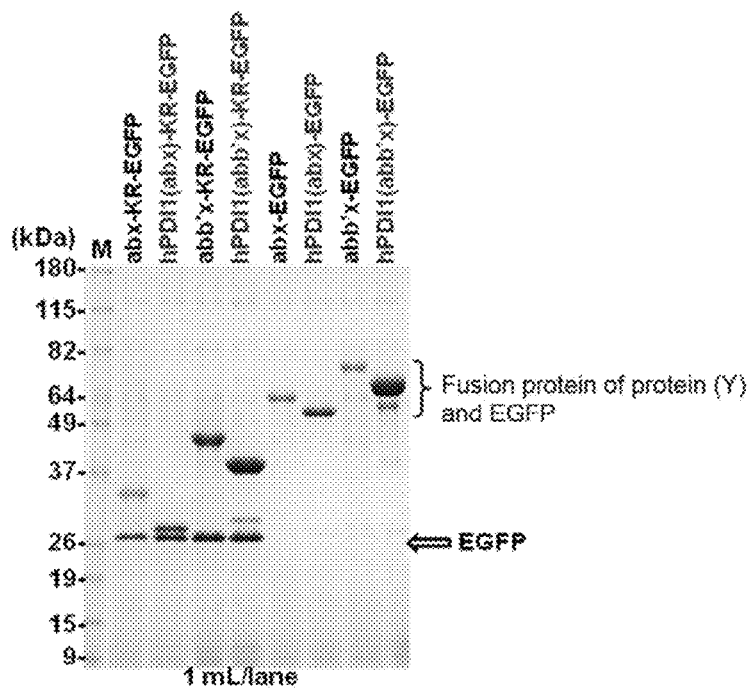
FIG. 25 is a CBB staining image of Test Example 13.
Figure 26:
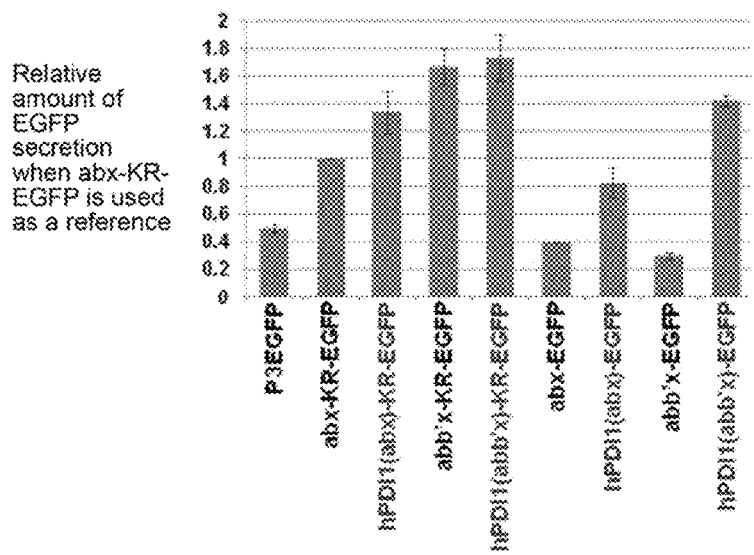
FIG. 26 is a graph showing the relative amount of EGFP secreted from each strain in Test Example 13.

FIG. 25 shows the CBB staining image, and FIG. 26 shows the calculation results of the relative amount of EGFP secreted from each of the strains. "M" in FIG. 25 is the same as that of FIG. 3. As a result, in a case where the KR sequence was provided as the cleavage site (W), either between abx-EGFP strain and hPDI(abx)-KR-EGFP strain, or between abb'x-KR-EGFP strain and hPDI(abb'x)-KR-EGFP strain, almost no difference in the secretion amount of EGFP was observed. On the other hand, when any one of PDI1(abx), PDI1(SP)-hPDI(abx) and PDI1(SP)-hPDI(abb'x) was used as protein (Y), the secretory production efficiency was found to be higher than the case of using P3 secretion signal peptide.

In a case where the cleavage site (W) was not provided, hPDI(abx)-EGFP strain and hPDI(abb'x)-EGFP strain were clearly improved as compared with abx-EGFP strain and abb'x-EGFP strain, respectively, in terms of the secretion amount of a fusion protein of protein (Y) and EGFP, and accordingly, the superiority of protein (Y) in which its *S. pombe*-derived abx or abb'x moiety was replaced with human-derived one was shown.

Test Example 14

With respect to the secretory production amount of GCSF, the case of using PDI1(abx) or PDI1(abb'x) as protein (Y) and the case of using PDI1(SP)-hPDI(abx) or PDI1(SP)-hPDI(abb'x) were compared.

(Construction of Expression Vector)

Into the multiple cloning sites of pPDI1(abx)-AflIII, pPDI1(abb'x)-AflIII, pPDI1(SP)-hPDI(abx)-AflIII and pPDI1(SP)-hPDI(abb'x)-AflIII, a gene sequence encoding GCSF was inserted to prepare expression vectors pPDI1(abx)-GCSF, pPDI(abb'x)-GCSF, pPDI1(SP)-hPDI(abx)-GCSF, and pPDI1(SP)-hPDI(abb'x)-GCSF comprising a structural gene encoding a fusion protein of PDI1(abx), PDI(abb'x), PDI1(SP)-hPDI(abx) or PDI1(SP)-hPDI(abb'x) and GCSF, and in the same manner, expression vectors pPDI1(abx)-KR-GCSF, pPDI1(SP)-hPDI(abx)-KR-GCSF, and pPDI1(SP)-hPDI(abb'x)-KR-GCSF comprising a structural gene encoding a fusion protein in which PDI1(abx), PDI1(SP)-hPDI(abx) or PDI1(SP)-hPDI(abb'x) is bound to GCSF via a KR peptide were prepared separately.

Specifically, PCR was carried out by using a gene encoding GCSF as a template, a forward primer (SEQ ID NO: 46) comprising the restriction enzyme recognition site for AarI at the 5' end, and a reverse primer of SEQ ID NO: 36, thereby to obtain a PCR product (GCSF fragment) having the restriction enzyme recognition site for AarI at the 5' end and the restriction enzyme recognition site for KpnI at the 3' end of the whole ORF of GCSF gene. The GCSF fragment was subjected to double digestion with restriction enzymes AarI and KpnI, and each of pPDI1(abx)-AflIII, pPDI1(abb'x)-AflIII, pPDI1(SP)-hPDI(abx)-AflIII and pPDI1(SP)-hPDI(abb'x)-AflIII was subjected to double digestion with restriction enzymes AflIII and KpnI, followed by ligating the GCSF fragment to pPDI1(abx)-AflIII, pPDI1(abb'x)-AflIII, pPDI1(SP)-hPDI(abx)-AflIII or pPDI1(SP)-hPDI(abb'x)-AflIII for transforming *E. coli* DH5α to obtain plasmids. Thus obtained plasmids were named as pPDI1(abx)-GCSF, pPDI1(abb'x)-GCSF, pPDI1(SP)-hPDI(abx)-GCSF, and pPDI1(SP)-hPDI(abb'x)-GCSF, respectively.

Further, pPDI1(abb'x)-KR-GCSF was subjected to double digestion with restriction enzymes AflIII and SalI to collect KR-bound GCSF fragment. On the other hand, each of pPDI1(abx)-AflIII, pPDI1(SP)-hPDI(abx)-AflIII and pPDI1(SP)-hPDI(abb'x)-AflIII was subjected to double digestion with restriction enzymes AflIII and SalI, followed by ligating the KR-bound GCSF fragment to pPDI1(abx)-AflIII, pPDI1(SP)-hPDI(abx)-AflIII or pPDI1(SP)-hPDI(abb'x)-AflIII for transforming *E. coli* DH5α to obtain plasmids. Thus obtained plasmids were named as pPDI1(abx)-KR-GCSF, pPDI1(SP)-hPDI(abx)-KR-GCSF, and pPDI1(SP)-hPDI(abb'x)-KR-GCSF, respectively.

(Preparation of Transformant)

By using the prepared expression vectors and employing A8 strain as a host, transformants were prepared in the same manner as in Test Example 1. The transformant prepared by using pPDI1(abx)-GCSF was named as abx-GCSF strain, the transformant prepared by using pPDI1(abb'x)-GCSF was named as abb'x-GCSF strain, the transformant prepared by using pPDI1(SP)-hPDI(abx)-GCSF was named as hPDI(abx)-GCSF strain, the transformant prepared by using pPDI1(SP)-hPDI(abb'x)-GCSF was named as hPDI(abb'x)-GCSF strain, the transformant prepared by using pPDI1(abx)-KR-GCSF was named as abx-KR-GCSF strain, the transformant prepared by using pPDI1(SP)-hPDI(abx)-KR-GCSF was named as hPDI(abx)-KR-GCSF strain, and the transformant prepared by using pPDI1(SP)-hPDI(abb'x)-KR-GCSF was named as hPDI(abb'x)-KR-GCSF strain.

(Secretory Production of Protein)

In the same manner as in Test Example 1, each of the above-prepared transformants, and abb'x-KR-GCSF strain prepared in Test Example A was cultivated, and a precipitate was collected by TCA precipitation. To the precipitate, 40 μl of a SDS-PAGE sample buffer was added, and incubated for 5 minutes at 95° C. to prepare a sample. 10 μl of the sample (corresponds to 1 ml of the culture supernatant) was applied on an acrylamide gel. After carrying out SDS-PAGE, in the same manner as in Test Example 3, a CBB staining image was obtained, and then each band was quantified to calculate a relative amount of GCSF secreted from each transformant, where the amount of GCSF secreted from abx-KR-GCSF strain was set as 1.

Figure 27:
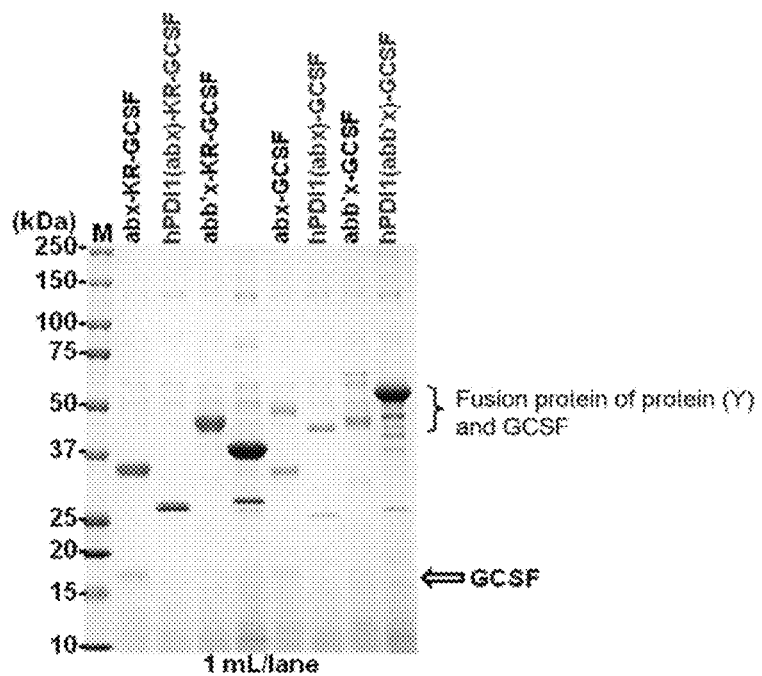
FIG. 27 is a CBB staining image of Test Example 14.
Figure 28:
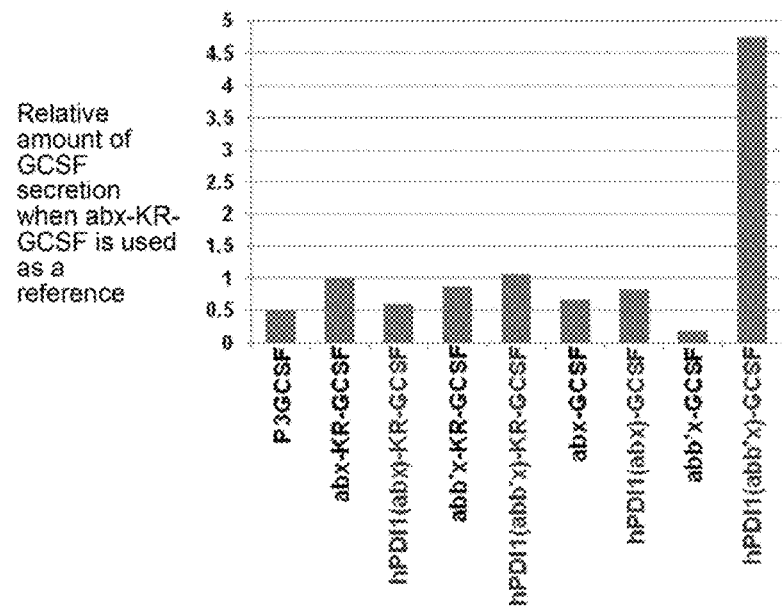
FIG. 28 is a graph showing the relative amount of EGFP secreted from each strain in Test Example 14.

FIG. 27 shows the CBB staining image, and FIG. 28 shows the calculation results of the relative amount of EGFP secreted from each of the strains. "M" in FIG. 27 is the same as that of FIG. 3. As a result, in a case where the KR sequence was provided as the cleavage site (W), among the cases of using PDI1(abx), PDI1(SP)-hPDI(abx) or PDI1(SP)-hPDI(abb'x) as protein (Y), no significant differences in the secretion amounts of GCSF were found. On the other hand, in a case where the cleavage site (W) was not provided, the secretion amount of a fusion protein of protein (Y) and GCSF in hPDI(abb'x)-GCSF strain was found to be clearly larger than that of the other transformants, and the secretion amount of GCSF itself was also found to be increased. From these results, it was found that the secretory production efficiency of GCSF increases by having PDI1(SP)-hPDI(abb'x) at the N-terminal and not providing the cleavage site (W).

INDUSTRIAL APPLICABILITY

According to the expression vector and the method for producing a protein of the present invention, the secretory production of a protein can be carried out efficiently, and therefore, they can be suitably applied for, particularly, a large-scale production of useful proteins.

What is claimed is:

1. An expression vector comprising an expression cassette containing a structural gene sequence (y) encoding a protein (Y), a structural gene sequence (z) located downstream from the structural gene sequence (y) and encoding a protein (Z) that is a protein to be recovered, and a promoter sequence and a terminator sequence for expressing a fusion protein containing the protein (Y) moiety and the protein (Z) moiety,
  wherein the protein (Y) is
    a partial protein of PDI1 comprising an endoplasmic reticulum (ER) targeting signal, a PDI1 a-domain, a PDI1 b-domain, and a PDI1 x-domain,
      wherein said ER targeting signal is followed by a PDI1 a-domain, a PDI1 b-domain, and a PDI1 x-domain and wherein said PDI1 b-domain and said PDI1 x-domain are directly fused to one another in the order of PDI1 b-domain-PDI1 x-domain, or
    a partial protein of PDI1 comprising an endoplasmic reticulum (ER) targeting signal, a PDI1 a-domain, a PDI1 b-domain, a PDI1 b'-domain, and a PDI1 x-domain, and which does not contain either one of a PDI1 a'-domain or a PDI1 c-domain,
      wherein said ER targeting signal is followed by a PDI1 a-domain, a PDI1 b-domain, a PDI1 b'-domain, and a PDI1' x-domain.

2. The expression vector according to claim 1, wherein the protein (Y) has an endoplasmic reticulum targeting signal of PDI1.

3. The expression vector according to claim 1, wherein the PDI1 is PDI1 from yeast, PDI1 from filamentous fungus, or PDI1 from human.

4. The expression vector according to claim 1, further comprising a structural gene sequence (w), in between the structural gene sequence (y) and the structural gene sequence (z), encoding a cleavage site (W) that is comprised of an amino acid or a peptide and functions as a site to be cleaved at the N-terminal side of the protein (Z) moiety either in inside or outside of a cell.

5. The expression vector according to claim 4, wherein the cleavage site (W) is a site to be cleaved at the N-terminal side of the protein (Z) moiety of the fusion protein in inside of a cell.

6. The expression vector according to claim 5, wherein the cleavage site (W) is KR (K: lysine, R: arginine), or a peptide comprised of at least three amino acids and has KR at its C-terminal side that binds to the protein (Z) moiety.

7. The expression vector according to claim 4, wherein the cleavage site (W) is a site recognized by a protease that can cleave the N-terminal side of the protein (Z) moiety of the fusion protein.

8. A method for producing a transformant, characterized in that the expression vector as defined in claim 1 is introduced into a host cell.

9. A transformant comprising the expression vector as defined in claim 1 as an extrachromosomal gene.

10. A transformant comprising the expression cassette of the expression vector as defined in claim 1 in a chromosome.

11. A method for producing a protein, comprising cultivating the transformant as defined in claim 9 and recovering the fusion protein or the protein (Z) from a culture broth obtained by cultivation.

12. A method for producing a protein, comprising cultivating the transformant as defined in claim 10 and recovering the fusion protein or the protein (Z) from a culture broth obtained by cultivation.

13. A method for producing a protein, comprising cultivating a transformant having the expression cassette of the expression vector as defined in claim 7 in a chromosome or having the expression vector as defined in claim 7 as an extrachromosomal gene, recovering the fusion protein from a culture broth obtained by cultivation, and cleaving the N-terminal side of the protein (Z) moiety of the fusion protein by means of a protease to produce the protein (Z).

14. A cloning vector comprising a promoter sequence capable of functioning in a host cell, a structural gene sequence (y) encoding a protein (Y) located downstream from the promoter and regulated by the promoter, a cloning site located downstream from the structural gene sequence (y) for introducing a structural gene, and a terminator sequence capable of functioning in the host cell,
wherein the protein (Y) is
a partial protein of PDI1 comprising an endoplasmic reticulum (ER) targeting signal, a PDI1 a-domain, a PDI1 b-domain, and a PDI1 x-domain,
wherein said ER targeting signal is followed by a PDI1 a-domain, a PDI1 b-domain, and a PDI1 x-domain and wherein said PDI1 b-domain and said PDI1 x-domain are directly fused to one another in the order of PDI1 b-domain-PDI1 x-domain, or
a partial protein of PDI1 comprising an endoplasmic reticulum (ER) targeting signal, a PDI1 a-domain, a PDI1 b-domain, a PDI1 b'-domain, and a PDI1 x-domain, and which does not contain either one of a PDI1 a'-domain or a PDI1 c-domain,
wherein said ER targeting signal is followed by a PDI1 a-domain, a PDI1 b-domain, a PDI1 b'-domain, and a PDI1 x-domain.

15. The expression vector according to claim 1, wherein the protein (Y) is a partial protein of PDI1 comprising an endoplasmic reticulum (ER) targeting signal, a PDI1 a-domain, a PDI1 b-domain, and a PDI1 x-domain,
wherein said ER targeting signal is followed by a PDI1 a-domain, a PDI1 b-domain, and a PDI1 x-domain and wherein said PDI1 b-domain and said PDI1 x-domain are directly fused to one another in the order of PDI1 b-domain-PDI1 x-domain.

16. The expression vector according to claim 1, wherein the protein (Y) is a partial protein of PDI1 comprising an endoplasmic reticulum (ER) targeting signal, a PDI1 a-domain, a PDI1 b-domain, a PDI1 b'-domain, and a PDI1 x-domain, and which does not contain either one of a PDI1 a'-domain or a PDI1 c-domain,
wherein said ER targeting signal is followed by a PDI1 a-domain, a PDI1 b-domain, a PDI1 b'-domain, and a PDI1 x-domain.

* * * * *

SEQUENCE LISTING

```
<160> NUMBER OF SEQ ID NOS: 46

<210> SEQ ID NO 1
<211> LENGTH: 492
<212> TYPE: PRT
<213> ORGANISM: Schizosaccharomyces pombe

<400> SEQUENCE: 1

Met Lys Ile Ser Asn Leu Leu Ala Ala Phe Leu Ala Phe Ser Gly Gly
1               5                   10                  15

Phe Phe Cys Ala Ser Ala Glu Val Pro Lys Val Asn Lys Glu Gly Leu
            20                  25                  30

Asn Glu Leu Ile Thr Ala Asp Lys Val Leu Met Val Lys Phe Tyr Ala
        35                  40                  45

Pro Trp Cys Gly His Cys Lys Ala Leu Ala Pro Glu Tyr Glu Ser Ala
    50                  55                  60

Ala Asp Glu Leu Glu Lys Asp Gly Ile Ser Leu Val Glu Val Asp Cys
65                  70                  75                  80

Thr Glu Glu Gly Asp Leu Cys Ser Glu Tyr Ser Ile Arg Gly Tyr Pro
                85                  90                  95

Thr Leu Asn Val Phe Lys Asn Gly Lys Gln Ile Ser Gln Tyr Ser Gly
            100                 105                 110

Pro Arg Lys His Asp Ala Leu Val Lys Tyr Met Arg Lys Gln Leu Leu
        115                 120                 125

Pro Thr Val Lys Pro Ile Ser Lys Asp Thr Leu Glu Asn Phe Val Glu
    130                 135                 140

Lys Ala Asp Asp Leu Ala Val Val Ala Phe Phe Lys Asp Gln Lys Leu
145                 150                 155                 160

Asn Asp Thr Tyr Thr Glu Val Ala Glu Val Met Lys Asp Asp Phe Val
                165                 170                 175
```

```
Phe Ala Ala Ser Asp Asp Lys Glu Leu Ala Lys Ser Leu Gly Ser Asn
                180                 185                 190

Phe Pro Gly Ile Val Ala Phe Thr Lys Asp Ala Ala Gln Asp Ser Asp
            195                 200                 205

Lys Leu Val Tyr Thr Gly Asp Trp Pro Ala Ser Ile Ala Asp Phe
        210                 215                 220

Ile Gly Val Ser Ser Ile Pro Leu Leu Asp Glu Leu Asn Gln Met Thr
225                 230                 235                 240

Phe Gly Lys Tyr Gln Gln Ser Gly Leu Pro Leu Gly Ile Ile Phe Tyr
                245                 250                 255

Asn Ser Thr Glu Ser Arg Asp Glu Leu Tyr Asp Val Phe Gln Pro Leu
                260                 265                 270

Ala Lys Lys Tyr Gln Asp Thr Leu Arg Phe Ala Phe Leu Asp Ala Val
            275                 280                 285

Arg Tyr Gly Ala Val Ala Lys Gln Met Asn Val Glu Ser Asp Trp Pro
        290                 295                 300

Ala Phe Val Ile Ala Asn Leu Lys Ser Met Leu Lys Tyr Pro Phe Pro
305                 310                 315                 320

Thr Thr Glu Leu Thr Ala Lys Ala Met Thr Lys Phe Val Gly Asp Phe
                325                 330                 335

Val Asp Gly Lys Leu Gln Pro Lys Ile Lys Ser Gln Pro Ile Pro Glu
            340                 345                 350

Ser Gln Glu Asp Leu Val Val Leu Val Ala Asp Asn Phe Asp Asp Ile
        355                 360                 365

Val Met Asp Glu Thr Lys Asp Val Leu Val Glu Phe Tyr Ala Pro Trp
370                 375                 380

Cys Gly His Cys Lys Asn Leu Ala Pro Thr Tyr Glu Lys Leu Ala Glu
385                 390                 395                 400

Glu Tyr Ser Asp Asp Ser Asn Val Val Ala Lys Ile Asp Ala Thr
                405                 410                 415

Glu Asn Asp Ile Ser Val Ser Ile Ser Gly Phe Pro Thr Ile Met Phe
            420                 425                 430

Phe Lys Ala Asn Asp Lys Val Asn Pro Val Arg Tyr Glu Gly Asp Arg
        435                 440                 445

Thr Leu Glu Asp Leu Ser Ala Phe Ile Asp Lys His Ala Ser Phe Glu
450                 455                 460

Pro Ile Lys Lys Glu Lys Ser Val Pro Ala Pro Asp Leu Glu Asp
465                 470                 475                 480

Gln Val Ala Val Glu Asp Glu Met Ala Asp Glu Leu
                485                 490

<210> SEQ ID NO 2
<211> LENGTH: 520
<212> TYPE: PRT
<213> ORGANISM: Kluyveromyces marxianus

<400> SEQUENCE: 2

Met Leu Phe Gly Lys Thr Ile Lys Leu Gly Leu Ala Thr Leu Met Ala
1               5                   10                  15

Val Asn Ala Ala Ala Gln Glu Glu Ala Thr Ala Pro Glu Asp Ser Ala
            20                  25                  30

Val Ile Lys Leu Thr Ser Glu Thr Phe Glu Asp Phe Ile Lys Glu His
        35                  40                  45

Pro Leu Val Leu Ala Glu Phe Tyr Ala Pro Trp Cys Gly His Cys Lys
    50                  55                  60
```

-continued

```
His Leu Ala Pro Glu Tyr Val Lys Ala Asp Glu Leu Glu Asp Lys
 65                  70                  75                  80

Asp Ile Pro Leu Ala Gln Ile Asp Cys Thr Glu Asn Gln Gln Leu Cys
                 85                  90                  95

Gln Glu Gln Gly Ile Pro Gly Tyr Pro Ser Leu Asn Val Phe Arg Asn
            100                 105                 110

Gly Asn Ser Lys Pro Ala Gly Glu Tyr Gln Gly Pro Arg Glu Ala Lys
            115                 120                 125

Ala Ile Val Asn Tyr Met Leu Lys Gln Ser Glu Pro Ala Val Arg Val
        130                 135                 140

Ile Glu Asp Glu Lys Glu Phe Lys Glu Leu Val Val Lys Asn Leu Asp
145                 150                 155                 160

Asn Val Leu Val Val Asp Gly Asn Val Pro Lys Phe Asn Glu Thr Phe
                165                 170                 175

Tyr Gln Ile Ala Asp Asn Leu Arg Asp Asp Tyr Ser Phe Ile Gln His
            180                 185                 190

Gly Ser Asp Gly Lys Leu Arg Val Tyr Leu Pro Lys Glu Thr Glu Pro
        195                 200                 205

Ile Val Tyr Asp Gly Asp Lys Tyr Asp Ala Glu Ala Val Ser Ser Trp
210                 215                 220

Ile Ala Val Glu Ala Phe Pro Tyr Phe Gly Asp Val Asn Gly Glu Thr
225                 230                 235                 240

Tyr Gln Ala Tyr Met Ala Ala Lys Ile Pro Leu Ala Tyr Phe Phe Tyr
                245                 250                 255

Thr Thr Pro Glu Glu Arg Glu Glu Tyr Glu Pro His Phe Val Ala Leu
            260                 265                 270

Ala Lys Lys Tyr Arg Gly Lys Val Asn Phe Ala Gly Leu Asp Ala Ser
        275                 280                 285

Lys Phe Gly Arg His Ala Glu Asn Leu Asn His Met Gln Gln Phe Pro
290                 295                 300

Leu Phe Ala Ile His Asp Thr Val Lys Asp Leu Lys Tyr Gly Leu Pro
305                 310                 315                 320

Gln Leu Ser Asp Glu Asp Phe Ala Ala Leu Glu Lys Pro Leu Lys Leu
                325                 330                 335

Ala Thr Lys Asp Ile Glu Lys Phe Val Lys Asp Phe Leu Asp Glu Ala
            340                 345                 350

Val Asp Pro Ile Val Lys Ser Glu Glu Ile Pro Glu Lys Gln Glu Gln
        355                 360                 365

Tyr Thr Phe Lys Ile Val Gly Lys Asn His Asp Glu Ile Val Arg Asp
370                 375                 380

Pro Lys Lys Asp Val Leu Val Lys Tyr Tyr Ala Pro Trp Cys Gly His
385                 390                 395                 400

Cys Lys Arg Leu Ala Pro Ile Tyr Glu Asn Met Ala Glu Phe Val His
                405                 410                 415

Glu Ala Glu Glu Leu Lys Asp Lys Val Leu Ile Ala Asn Ile Asp Ala
            420                 425                 430

Thr Ala Asn Asp Val Gln Asn Val Glu Ile Pro Gly Phe Pro Ala Ile
        435                 440                 445

Tyr Leu Trp Pro Ala Gly Glu Lys Ser Glu Pro Ile Pro Phe Glu Gly
            450                 455                 460

Pro Arg Thr Ile Glu Ala Phe Leu Thr Phe Ile Lys Glu Asn Gly Thr
465                 470                 475                 480
```

-continued

```
Asn Gly Val Asp Gly Val Ser Leu Tyr Glu Glu Tyr Val Ile Ala Leu
            485                 490                 495

Glu Lys Lys Lys Gln Glu Glu Ala Ala Asp Glu Ala Asp Asp Glu
        500                 505                 510

Asp Glu Leu Asp Gln Asp Glu Leu
        515                 520

<210> SEQ ID NO 3
<211> LENGTH: 522
<212> TYPE: PRT
<213> ORGANISM: Saccharomyces cerevisiae

<400> SEQUENCE: 3

Met Lys Phe Ser Ala Gly Ala Val Leu Ser Trp Ser Ser Leu Leu Leu
1               5                   10                  15

Ala Ser Ser Val Phe Ala Gln Gln Glu Ala Val Ala Pro Glu Asp Ser
            20                  25                  30

Ala Val Val Lys Leu Ala Thr Asp Ser Phe Asn Glu Tyr Ile Gln Ser
        35                  40                  45

His Asp Leu Val Leu Ala Glu Phe Phe Ala Pro Trp Cys Gly His Cys
    50                  55                  60

Lys Asn Met Ala Pro Glu Tyr Val Lys Ala Ala Glu Thr Leu Val Glu
65                  70                  75                  80

Lys Asn Ile Thr Leu Ala Gln Ile Asp Cys Thr Glu Asn Gln Asp Leu
                85                  90                  95

Cys Met Glu His Asn Ile Pro Gly Phe Pro Ser Leu Lys Ile Phe Lys
            100                 105                 110

Asn Ser Asp Val Asn Asn Ser Ile Asp Tyr Glu Gly Pro Arg Thr Ala
        115                 120                 125

Glu Ala Ile Val Gln Phe Met Ile Lys Gln Ser Gln Pro Ala Val Ala
    130                 135                 140

Val Val Ala Asp Leu Pro Ala Tyr Leu Ala Asn Glu Thr Phe Val Thr
145                 150                 155                 160

Pro Val Ile Val Gln Ser Gly Lys Ile Asp Ala Asp Phe Asn Ala Thr
                165                 170                 175

Phe Tyr Ser Met Ala Asn Lys His Phe Asn Asp Tyr Asp Phe Val Ser
            180                 185                 190

Ala Glu Asn Ala Asp Asp Phe Lys Leu Ser Ile Tyr Leu Pro Ser
        195                 200                 205

Ala Met Asp Glu Pro Val Val Tyr Asn Gly Lys Lys Ala Asp Ile Ala
    210                 215                 220

Asp Ala Asp Val Phe Glu Lys Trp Leu Gln Val Glu Ala Leu Pro Tyr
225                 230                 235                 240

Phe Gly Glu Ile Asp Gly Ser Val Phe Ala Gln Tyr Val Glu Ser Gly
                245                 250                 255

Leu Pro Leu Gly Tyr Leu Phe Tyr Asn Asp Glu Glu Glu Leu Glu Glu
            260                 265                 270

Tyr Lys Pro Leu Phe Thr Glu Leu Ala Lys Lys Asn Arg Gly Leu Met
        275                 280                 285

Asn Phe Val Ser Ile Asp Ala Arg Lys Phe Gly Arg His Ala Gly Asn
    290                 295                 300

Leu Asn Met Lys Glu Gln Phe Pro Leu Phe Ala Ile His Asp Met Thr
305                 310                 315                 320

Glu Asp Leu Lys Tyr Gly Leu Pro Gln Leu Ser Glu Glu Ala Phe Asp
                325                 330                 335
```

```
Glu Leu Ser Asp Lys Ile Val Leu Glu Ser Lys Ala Ile Glu Ser Leu
            340                 345                 350

Val Lys Asp Phe Leu Lys Gly Asp Ala Ser Pro Ile Val Lys Ser Gln
            355                 360                 365

Glu Ile Phe Glu Asn Gln Asp Ser Ser Val Phe Gln Leu Val Gly Lys
            370                 375                 380

Asn His Asp Glu Ile Val Asn Asp Pro Lys Lys Asp Val Leu Val Leu
385                 390                 395                 400

Tyr Tyr Ala Pro Trp Cys Gly His Cys Lys Arg Leu Ala Pro Thr Tyr
                405                 410                 415

Gln Glu Leu Ala Asp Thr Tyr Ala Asn Ala Thr Ser Asp Val Leu Ile
            420                 425                 430

Ala Lys Leu Asp His Thr Glu Asn Asp Val Arg Gly Val Val Ile Glu
            435                 440                 445

Gly Tyr Pro Thr Ile Val Leu Tyr Pro Gly Gly Lys Lys Ser Glu Ser
            450                 455                 460

Val Val Tyr Gln Gly Ser Arg Ser Leu Asp Ser Leu Phe Asp Phe Ile
465                 470                 475                 480

Lys Glu Asn Gly His Phe Asp Val Asp Gly Lys Ala Leu Tyr Glu Glu
                485                 490                 495

Ala Gln Glu Lys Ala Ala Glu Ala Asp Ala Asp Ala Glu Leu Ala
            500                 505                 510

Asp Glu Glu Asp Ala Ile His Asp Glu Leu
            515                 520
```

<210> SEQ ID NO 4
<211> LENGTH: 517
<212> TYPE: PRT
<213> ORGANISM: Pichia pastoris

<400> SEQUENCE: 4

```
Met Gln Phe Asn Trp Asn Ile Lys Thr Val Ala Ser Ile Leu Ser Ala
1               5                   10                  15

Leu Thr Leu Ala Gln Ala Ser Asp Gln Glu Ala Ile Ala Pro Glu Asp
            20                  25                  30

Ser His Val Val Lys Leu Thr Glu Ala Thr Phe Glu Ser Phe Ile Thr
            35                  40                  45

Ser Asn Pro His Val Leu Ala Glu Phe Phe Ala Pro Trp Cys Gly His
            50                  55                  60

Cys Lys Lys Leu Gly Pro Glu Leu Val Ser Ala Glu Ile Leu Lys
65                  70                  75                  80

Asp Asn Glu Gln Val Lys Ile Ala Gln Ile Asp Cys Thr Glu Glu Lys
                85                  90                  95

Glu Leu Cys Gln Gly Tyr Glu Ile Lys Gly Tyr Pro Thr Leu Lys Val
            100                 105                 110

Phe His Gly Glu Val Glu Val Pro Ser Asp Tyr Gln Gly Gln Arg Gln
            115                 120                 125

Ser Gln Ser Ile Val Ser Tyr Met Leu Lys Gln Ser Leu Pro Pro Val
            130                 135                 140

Ser Glu Ile Asn Ala Thr Lys Asp Leu Asp Thr Ile Ala Glu Ala
145                 150                 155                 160

Lys Glu Pro Val Ile Val Gln Val Leu Pro Glu Asp Ala Ser Asn Leu
                165                 170                 175

Glu Ser Asn Thr Thr Phe Tyr Gly Val Ala Gly Thr Leu Arg Glu Lys
```

```
                 180                 185                 190
Phe Thr Phe Val Ser Thr Lys Ser Thr Asp Tyr Ala Lys Lys Tyr Thr
            195                 200                 205
Ser Asp Ser Thr Pro Ala Tyr Leu Leu Val Arg Pro Gly Glu Glu Pro
        210                 215                 220
Ser Val Tyr Ser Gly Glu Glu Leu Asp Glu Thr His Leu Val His Trp
225                 230                 235                 240
Ile Asp Ile Glu Ser Lys Pro Leu Phe Gly Asp Ile Asp Gly Ser Thr
                245                 250                 255
Phe Lys Ser Tyr Ala Glu Ala Asn Ile Pro Leu Ala Tyr Tyr Phe Tyr
            260                 265                 270
Glu Asn Glu Glu Gln Arg Ala Ala Ala Asp Ile Ile Lys Pro Phe
        275                 280                 285
Ala Lys Glu Gln Arg Gly Lys Ile Asn Phe Val Gly Leu Asp Ala Val
        290                 295                 300
Lys Phe Gly Lys His Ala Lys Asn Leu Asn Met Asp Glu Glu Lys Leu
305                 310                 315                 320
Pro Leu Phe Val Ile His Asp Leu Val Ser Asn Lys Lys Phe Gly Val
                325                 330                 335
Pro Gln Asp Gln Glu Leu Thr Asn Lys Asp Val Thr Glu Leu Ile Glu
            340                 345                 350
Lys Phe Ile Ala Gly Glu Ala Glu Pro Ile Val Lys Ser Glu Pro Ile
        355                 360                 365
Pro Glu Ile Gln Glu Glu Lys Val Phe Lys Leu Val Gly Lys Ala His
    370                 375                 380
Asp Glu Val Val Phe Asp Glu Ser Lys Asp Val Leu Val Lys Tyr Tyr
385                 390                 395                 400
Ala Pro Trp Cys Gly His Cys Lys Arg Met Ala Pro Ala Tyr Glu Glu
                405                 410                 415
Leu Ala Thr Leu Tyr Ala Asn Asp Glu Asp Ala Ser Ser Lys Val Val
            420                 425                 430
Ile Ala Lys Leu Asp His Thr Leu Asn Asp Val Asp Asn Val Asp Ile
        435                 440                 445
Gln Gly Tyr Pro Thr Leu Ile Leu Tyr Pro Ala Gly Asp Lys Ser Asn
    450                 455                 460
Pro Gln Leu Tyr Asp Gly Ser Arg Asp Leu Glu Ser Leu Ala Glu Phe
465                 470                 475                 480
Val Lys Glu Arg Gly Thr His Lys Val Asp Ala Leu Ala Leu Arg Pro
                485                 490                 495
Val Glu Glu Glu Lys Glu Ala Glu Glu Ala Glu Ser Glu Ala Asp
            500                 505                 510
Ala His Asp Glu Leu
            515

<210> SEQ ID NO 5
<211> LENGTH: 511
<212> TYPE: PRT
<213> ORGANISM: Candida albicans

<400> SEQUENCE: 5

Met Lys Phe Trp Thr Tyr Ser Thr Lys Val Leu Ala Thr Leu Leu Ala
1               5                   10                  15
Val Val Ser Ile Thr His Ala Ser Gly Pro Thr Asp Gly Asp Ala Val
            20                  25                  30
```

```
Ala Asp Pro Asn Ser Ala Val Val Lys Leu Thr Ser Glu Asn Phe Ala
             35                  40                  45
Ser Phe Ile Glu Glu Asn Pro Leu Ile Leu Ala Glu Phe Phe Ala Pro
 50                  55                  60
Trp Cys Gly Tyr Cys Lys Met Leu Gly Pro Glu Tyr Ser Lys Ala Ala
 65                  70                  75                  80
Asp Ser Leu Asn Glu Ser His Pro Lys Ile Lys Leu Ala Gln Ile Asp
                 85                  90                  95
Cys Thr Glu Asp Glu Ala Leu Cys Met Glu His Gly Ile Arg Gly Tyr
            100                 105                 110
Pro Thr Leu Lys Ile Ile Arg Asp Gly Asp Ser Lys Thr Ala Glu Asp
            115                 120                 125
Tyr Gln Gly Pro Arg Glu Ala Ala Gly Ile Ala Asp Tyr Met Ile Lys
            130                 135                 140
Gln Ser Leu Pro Ala Val Gln Phe Pro Glu Thr Phe Glu Glu Leu Asp
145                 150                 155                 160
Thr Leu Ile Asp Ala Gln Thr Lys Pro Phe Val Leu Gln Ile Asn Pro
                165                 170                 175
Thr Glu Asp Gly Asn Ala Thr Phe Asn Lys Val Ala Asn Gln Lys Arg
            180                 185                 190
Lys Asp Tyr Val Phe Ile Asn Val Glu Asp Lys Gln Ile Ile Lys Asp
            195                 200                 205
Leu Asn Lys Lys Phe Lys Asn Val Asp Ile Thr Gly Lys Lys Pro Ser
            210                 215                 220
Tyr Leu Val Val Gln Pro Lys Gln Phe Asp Glu Val Ala Lys Phe Asp
225                 230                 235                 240
Gly Lys Lys Ile Asp Ala Glu Ser Leu Thr Glu Phe Ile Gly Val Glu
                245                 250                 255
Ala Val Pro Tyr Phe Gly Glu Ile Asn Gln Asp Thr Tyr Met Thr Tyr
            260                 265                 270
Met Thr Ser Pro Leu Pro Ile Ala Tyr Tyr Phe Tyr Asn Asn Ala Glu
            275                 280                 285
Gln Arg Glu Ala Ile Ala Asp Asp Leu Thr Lys Leu Gly Lys Lys Tyr
            290                 295                 300
Arg Gly Lys Leu Asn Ile Val Gly Leu Asp Ala Ser Leu Phe Gly Arg
305                 310                 315                 320
His Ala Glu Val Ile Asn Met Asp Pro Glu Val Val Pro Leu Phe Ala
                325                 330                 335
Ile His His Ile Ser Asp Asn Lys Lys Phe Gly Val Asn Gln Thr Asp
            340                 345                 350
Tyr Pro Glu Gly Pro Ser Phe Lys Val Ile Glu Lys Phe Val Ala Asp
            355                 360                 365
Tyr Phe Ala Asp Lys Leu Thr Pro Ile Ile Lys Ser Glu Pro Leu Pro
            370                 375                 380
Thr Glu Glu Glu Lys Ser Ala Asn Pro Val Val Lys Leu Val Ala His
385                 390                 395                 400
Asn Tyr Lys Asp Val Leu Glu Gln Thr Asp Lys Asp Val Phe Val Lys
                405                 410                 415
Tyr Tyr Ala Pro Trp Cys Gly His Cys Lys Lys Leu Ala Pro Thr Trp
            420                 425                 430
Glu Glu Leu Ala Glu Ile Phe Gly Ser Asn Lys Asp Asp Ala Lys Val
            435                 440                 445
Val Val Ala Asp Ile Asp His Thr Asn Asn Asp Val Asp Val Pro Tyr
```

```
                450           455           460
Asn Ile Glu Gly Tyr Pro Thr Leu Leu Met Phe Pro Ala Asn Gly Lys
465                 470                 475                 480

Val Asp Glu Lys Thr Gly Ile Arg Glu Pro Ile Val Phe Glu Gly Pro
                485                 490                 495

Arg Glu Leu Asp Thr Leu Ile Glu Phe Ile Lys Glu Lys Gly His
                500                 505                 510
```

<210> SEQ ID NO 6
<211> LENGTH: 502
<212> TYPE: PRT
<213> ORGANISM: Trichoderma reesei

<400> SEQUENCE: 6

```
Met Gln Gln Lys Arg Leu Thr Ala Ala Leu Val Ala Ala Leu Ala Ala
1               5                   10                  15

Val Val Ser Ala Glu Ser Asp Val Lys Ser Leu Thr Lys Asp Thr Phe
                20                  25                  30

Asn Asp Phe Ile Asn Ser Asn Asp Leu Val Leu Ala Glu Ser Phe Ala
                35                  40                  45

Pro Trp Cys Gly His Cys Lys Ala Leu Ala Pro Glu Tyr Glu Glu Ala
            50                  55                  60

Ala Thr Thr Leu Lys Asp Lys Ser Ile Lys Leu Ala Lys Val Asp Cys
65                  70                  75                  80

Val Glu Glu Ala Asp Leu Cys Lys Glu His Gly Val Glu Gly Tyr Pro
                85                  90                  95

Thr Leu Lys Val Phe Arg Gly Leu Asp Lys Val Ala Pro Tyr Thr Gly
                100                 105                 110

Pro Arg Lys Ala Asp Gly Ile Thr Ser Tyr Met Val Lys Gln Ser Leu
            115                 120                 125

Pro Ala Val Ser Ala Leu Thr Lys Asp Thr Leu Glu Asp Phe Lys Thr
            130                 135                 140

Ala Asp Lys Val Val Leu Val Ala Tyr Ile Ala Ala Asp Lys Ala
145                 150                 155                 160

Ser Asn Glu Thr Phe Thr Ala Leu Ala Asn Glu Leu Arg Asp Thr Tyr
                165                 170                 175

Leu Phe Gly Gly Val Asn Asp Ala Ala Val Ala Glu Ala Gly Val
            180                 185                 190

Lys Phe Pro Ser Ile Val Leu Tyr Lys Ser Phe Asp Glu Gly Lys Asn
            195                 200                 205

Val Phe Ser Glu Lys Phe Asp Ala Glu Ala Ile Arg Asn Phe Ala Gln
            210                 215                 220

Val Ala Ala Thr Pro Leu Val Gly Glu Val Gly Pro Glu Thr Tyr Ala
225                 230                 235                 240

Gly Tyr Met Ser Ala Gly Ile Pro Leu Ala Tyr Ile Phe Ala Glu Thr
                245                 250                 255

Ala Glu Glu Arg Glu Asn Leu Ala Lys Thr Leu Lys Pro Val Ala Glu
                260                 265                 270

Lys Tyr Lys Gly Lys Ile Asn Phe Ala Thr Ile Asp Ala Lys Asn Phe
            275                 280                 285

Gly Ser His Ala Gly Asn Ile Asn Leu Lys Thr Asp Lys Phe Pro Ala
            290                 295                 300

Phe Ala Ile His Asp Ile Glu Lys Asn Leu Lys Phe Pro Phe Asp Gln
305                 310                 315                 320
```

```
Ser Lys Glu Ile Thr Glu Lys Asp Ile Ala Ala Phe Val Asp Gly Phe
            325                 330                 335

Ser Ser Gly Lys Ile Glu Ala Ser Ile Lys Ser Glu Pro Ile Pro Glu
        340                 345                 350

Thr Gln Glu Gly Pro Val Thr Val Val Ala His Ser Tyr Lys Asp
        355                 360                 365

Ile Val Leu Asp Asp Lys Lys Asp Val Leu Ile Glu Phe Tyr Thr Pro
        370                 375                 380

Trp Cys Gly His Cys Lys Ala Leu Ala Pro Lys Tyr Asp Glu Leu Ala
385                 390                 395                 400

Ser Leu Tyr Ala Lys Ser Asp Phe Lys Asp Lys Val Val Ile Ala Lys
                405                 410                 415

Val Asp Ala Thr Ala Asn Asp Val Pro Asp Glu Ile Gln Gly Phe Pro
            420                 425                 430

Thr Ile Lys Leu Tyr Pro Ala Gly Asp Lys Lys Asn Pro Val Thr Tyr
            435                 440                 445

Ser Gly Ala Arg Thr Val Glu Asp Phe Ile Glu Phe Ile Lys Glu Asn
        450                 455                 460

Gly Lys Tyr Lys Ala Gly Val Glu Ile Pro Ala Glu Pro Thr Glu Glu
465                 470                 475                 480

Ala Glu Ala Ser Glu Ser Lys Ala Ser Glu Glu Ala Lys Ala Ser Glu
                485                 490                 495

Glu Thr His Asp Glu Leu
            500

<210> SEQ ID NO 7
<211> LENGTH: 515
<212> TYPE: PRT
<213> ORGANISM: Aspergillus oryzae

<400> SEQUENCE: 7

Met Arg Thr Phe Ala Pro Trp Ile Leu Ser Leu Leu Gly Ala Ser Ala
1               5                   10                  15

Val Ala Ser Ala Ala Asp Ala Thr Ala Glu Ala Pro Ser Asp Val Val
            20                  25                  30

Ser Leu Thr Gly Asp Thr Phe Glu Thr Phe Val Lys Glu His Asp Leu
        35                  40                  45

Val Leu Ala Glu Phe Phe Ala Pro Trp Cys Gly His Cys Lys Ala Leu
    50                  55                  60

Ala Pro Lys Tyr Glu Gln Ala Ala Thr Glu Leu Lys Glu Lys Asn Ile
65                  70                  75                  80

Pro Leu Val Lys Val Asp Cys Thr Glu Glu Ala Leu Cys Arg Asp
                85                  90                  95

Gln Gly Val Glu Gly Tyr Pro Thr Leu Lys Ile Phe Arg Gly Leu Asp
            100                 105                 110

Ala Val Lys Pro Tyr Gln Gly Ala Arg Gln Thr Glu Ala Ile Val Ser
        115                 120                 125

Tyr Met Val Lys Gln Ser Leu Pro Ala Val Ser Pro Val Thr Pro Glu
    130                 135                 140

Asn Leu Glu Glu Ile Lys Thr Met Asp Lys Ile Val Val Ile Gly Tyr
145                 150                 155                 160

Ile Ala Ser Asp Asp Gln Thr Ala Asn Asp Ile Phe Thr Thr Phe Ala
                165                 170                 175

Glu Ser Gln Arg Asp Asn Tyr Leu Phe Ala Ala Thr Ser Asp Ala Ser
            180                 185                 190
```

Ile Ala Lys Ala Glu Gly Val Lys Gln Pro Ser Ile Val Leu Tyr Lys
        195                 200                 205

Asp Phe Asp Glu Lys Lys Ala Thr Tyr Asp Gly Glu Ile Glu Gln Asp
    210                 215                 220

Ala Leu Leu Ser Trp Val Lys Thr Ala Ser Thr Pro Leu Val Gly Glu
225                 230                 235                 240

Leu Gly Pro Glu Thr Tyr Ser Gly Tyr Ile Thr Ala Gly Ile Pro Leu
                245                 250                 255

Ala Tyr Ile Phe Ala Glu Thr Lys Glu Glu Arg Glu Gln Phe Thr Glu
            260                 265                 270

Glu Phe Lys Phe Ile Ala Glu Lys His Lys Gly Ser Ile Asn Ile Val
        275                 280                 285

Thr Ile Asp Ala Lys Leu Tyr Gly Ala His Ala Gly Asn Leu Asn Leu
    290                 295                 300

Asp Pro Ser Lys Phe Pro Ala Phe Ala Ile Gln Asp Pro Glu Lys Asn
305                 310                 315                 320

Ala Lys Tyr Pro Tyr Asp Gln Ser Lys Glu Val Lys Ala Lys Asp Ile
                325                 330                 335

Gly Lys Phe Ile Gln Asp Val Leu Asp Asp Lys Val Glu Pro Ser Ile
            340                 345                 350

Lys Ser Glu Ala Ile Pro Glu Thr Gln Glu Gly Pro Val Thr Val Val
        355                 360                 365

Val Ala His Ser Tyr Lys Asp Leu Val Leu Asp Asn Glu Lys Asp Val
    370                 375                 380

Leu Leu Glu Phe Tyr Ala Pro Trp Cys Gly His Cys Lys Ala Leu Ala
385                 390                 395                 400

Pro Lys Tyr Glu Glu Leu Ala Ser Leu Tyr Lys Asp Ile Pro Glu Val
                405                 410                 415

Thr Ile Ala Lys Ile Asp Ala Thr Ala Asn Asp Val Pro Asp Ser Ile
            420                 425                 430

Thr Gly Phe Pro Thr Ile Lys Leu Phe Ala Ala Gly Ala Lys Asp Ser
        435                 440                 445

Pro Val Glu Tyr Glu Gly Ser Arg Thr Val Glu Asp Leu Ala Asn Phe
    450                 455                 460

Val Lys Glu Asn Gly Lys His Lys Val Asp Ala Leu Glu Val Asp Pro
465                 470                 475                 480

Lys Lys Glu Gln Glu Ser Gly Asp Ala Thr Glu Thr Arg Ala Ala Ser
                485                 490                 495

Asp Glu Thr Glu Thr Pro Ala Ala Thr Ser Asp Asp Lys Ser Glu His
            500                 505                 510

Asp Glu Leu
        515

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: P3
      secretory signal peptide

<400> SEQUENCE: 8

Met Lys Ile Thr Ala Val Ile Ala Leu Leu Phe Ser Leu Ala Ala Ala
1               5                   10                  15

Ser Pro Ile Pro Val Ala Asp Pro Gly Val Val Ser Val Ser Leu Lys

Lys Arg

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: synthetic primer

<400> SEQUENCE: 9
gaacgtctct catgaagatt agtaatttgt t                           31

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: synthetic primer

<400> SEQUENCE: 10
cttgtcgact taaagctcat cggccattt                             29

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: synthetic primer

<400> SEQUENCE: 11
cggggtaccc ttcttaagct catcggccat ttcgtc                     36

<210> SEQ ID NO 12
<211> LENGTH: 2040
<212> TYPE: DNA
<213> ORGANISM: Artificial Sequence
<220> FEATURE:
<223> OTHER INFORMATION: Description of Artificial Sequence: Artificial DNA coding hTF

<400> SEQUENCE: 12
gtccccgaca agaccgtccg ttggtgcgct gtctccgagc acgaggccac caagtgccaa      60
tccttccgtg accacatgaa gtccgtcatc ccttccgacg tccctccgt cgcctgcgtc     120 aagaaggctt cctaccttga ctgcatccgt gctatcgccg ccaacgaggc cgacgccgtc     180
acccttgacg ccggtcttgt ctacgacgcc taccttgccc ccaacaactt gaagcccgtc     240
gtcgccgagt tctacggttc caaggaggac ccccaaaacct tctactacgc cgtcgccgtc     300
gttaagaagg actccggttt ccaaatgaac caacttcgtg gtaagaagtc ctgccacacc     360
ggtcttggtc gttccgccgg ttggaacatc cccatcggtc ttttgtactg cgaccttccc     420
gagccccgta agcccttga gaaggccgtc gccaacttct ctccggttc ctgcgcccc      480 tgcgccgacg gtactgactt cccccaactt tgccaattgt gccccggttg cggttgctcc     540
acccttaacc aatacttcgg ttactccggt gccttcaagt gcttgaagga cggtgccggt     600
gacgtcgctt tcgtcaagca ctccaccatc ttcgagaacc ttgccaacaa ggccgaccgt     660
gaccaatacg agcttctttg ccttgacaac acccgtaagc cgttgacga gtacaaggac     720 tgccacctt cccaagtccc ttcccacacc gtcgtcgccc gttctatggg tggtaaggag     780

```
gaccttatct gggagcttct taaccaagcc caagagcact tcggtaagga caagtccaag    840
gagttccaac ttttctcctc cccccacggt aaggaccttt tgttcaagga ctccgcccac    900
ggtttcttga aggtcccccc tcgtatggac gccaagatgt accttggtta cgagtacgtc    960
accgccatcc gtaaccttcg tgagggtact tgccctgagg ccctactga cgagtgcaag   1020 cccgtcaagt ggtgcgccct ttcccaccac gagcgtttga agtgcgacga gtggtccgtc   1080
aactccgtcg gtaagatcga gtgcgttttcc gccgagacta ccgaggactg cattgccaag   1140
attatgaacg gtgaggccga cgctatgtcc cttgacggtg gtttcgtcta cattgccggt   1200
aagtgcggtc ttgtccccgt ccttgccgag aactacaaca aggctgacaa ctgcgaggac   1260 accccgagg ccggttactt cgctgtcgct gtcgtcaaga agtccgcctc cgaccttacc   1320
tgggacaact tgaagggtaa gaagtcttgc cacactgccg tcggtcgtac tgctggttgg   1380
aacattccta tgggttgct ttacaacaag atcaaccact gccgtttcga cgagttcttc   1440
tccgagggtt gcgcccctgg ttccaagaag gactcttccc tttgcaagtt gtgcatgggt   1500
tccggtctta acctttgcga gcccaacaac aaggagggtt actacggtta cactggtgct   1560
ttccgttgcc ttgtcgagaa gggtgacgtt gccttcgtta agcaccaaac cgtcccccaa   1620
aacaccggtg gtaagaaccc cgaccctggg gccaagaacc ttaacgagaa ggactacgag   1680
cttttgtgct tggacggtac tcgtaagcct gttgaggagt acgccaactg ccacttggcc   1740
cgtgccccca accacgccgt cgtcacccgt aaggacaagg aggcttgcgt ccacaagatc   1800
cttcgtcaac aacaacacct tttcggttcc aacgtcgccg actgctccgg taacttctgc   1860
cttttccgtt ccgagactaa ggaccttctt ttccgtgacg acaccgtctg ccttgccaag   1920
ttgcacgacc gtaacaccta cgagaagtac cttggtgagg agtacgttaa ggccgtcggt   1980
aaccttcgta agtgctccac ctcctcccctt ttggaggctt gcaccttccg tcgtccctaa   2040
```

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: synthetic
    primer

<400> SEQUENCE: 13
atgcttaagg tccccgacaa gaccgtccg                                       29

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: synthetic
    primer

<400> SEQUENCE: 14
gctctagatt agggacgacg gaaggtgc                                        28

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: synthetic
    primer

<400> SEQUENCE: 15
atgcttaaga agcgtgtccc cgacaagacc gtccg    35

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: synthetic
      primer

<400> SEQUENCE: 16
cggggtacct tacaagggaa tactagatac acc    33

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: synthetic
      primer

<400> SEQUENCE: 17
cggggtacct tatccatcaa caaaatcacc aacaaattta g    41

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: synthetic
      primer

<400> SEQUENCE: 18
cggggtacct tattgagatt caggaatggg ttgac    35

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: synthetic
      primer

<400> SEQUENCE: 19
cggggtacct taagaggcat gtttatctat aaaggc    36

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: synthetic
      primer

<400> SEQUENCE: 20
cggggtacct tacatttcgt cttccactgc gac    33

<210> SEQ ID NO 21
<211> LENGTH: 78
<212> TYPE: DNA
<213> ORGANISM: Artificial Sequence
<220> FEATURE:
<223> OTHER INFORMATION: Description of Artificial Sequence: synthetic
      primer

<400> SEQUENCE: 21
cggggtacct tattgagatt caggaatggg ttgacttta atctttggct gtagcttcaa    60
gggaatacta gatacacc                                                 78

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: synthetic
      primer

<400> SEQUENCE: 22
ctactaacac cactaaatct tctccatcaa caaaatcacc aac                      43

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: synthetic
      primer

<400> SEQUENCE: 23
gttggtgatt ttgttgatgg agaagattta gtggtgttag tag                      43

<210> SEQ ID NO 24
<211> LENGTH: 47
<212> TYPE: DNA
<213> ORGANISM: Artificial Sequence
<220> FEATURE:
<223> OTHER INFORMATION: Description of Artificial Sequence: synthetic
      primer

<400> SEQUENCE: 24
cggggtacca ggcctcttct taagttgaga ttcaggaatg ggttgac                  47

<210> SEQ ID NO 25
<211> LENGTH: 720
<212> TYPE: DNA
<213> ORGANISM: Artificial Sequence
<220> FEATURE:
<223> OTHER INFORMATION: Description of Artificial Sequence: Artificial
      DNA coding EGFP

<400> SEQUENCE: 25
atggtttcta agggtgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctacccga ccacatgaag    240 cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct ttacaagtaa   720

```
<210> SEQ ID NO 26
<211> LENGTH: 32
<212> TYPE: DNA
<213> ORGANISM: Artificial Sequence
<220> FEATURE:
<223> OTHER INFORMATION: Description of Artificial Sequence: synthetic
      primer

<400> SEQUENCE: 26
gggcttaaga tggtttctaa gggtgaggag ct                              32

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: synthetic
      primer

<400> SEQUENCE: 27
cccggtacct tacttgtaaa gctcgtcca                                  29

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: synthetic
      primer

<400> SEQUENCE: 28
gggcttaaga agcgtatggt ttctaagggt gaggagct                        38

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: synthetic
      primer

<400> SEQUENCE: 29
gccttagaat gaccagacca agg                                        23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: synthetic
      primer

<400> SEQUENCE: 30
ccttggtctg gtcattctaa ggc                                        23

<210> SEQ ID NO 31
<211> LENGTH: 577
<212> TYPE: DNA
<213> ORGANISM: Artificial Sequence
<220> FEATURE:
<223> OTHER INFORMATION: Description of Artificial Sequence: Artificial
      DNA coding hGH

<400> SEQUENCE: 31
ttccccacca attccccttt ccgtcttttt cgacaacgct atgcttcgtg cccaccgttt    60
gcaccaactt gccttcgaca cctaccaaga gttcgaggag gcttacatcc ctaaggagca   120
```

| | |
|---|---|
| aaagtactcc ttccttcaaa accccaaac ctccttgtgc ttctccgagt ctattcctac | 180 |
| cccctccaac cgtgaggaga cccaacaaaa gtccaacctt gagcttcttc gtatctccct | 240 |
| tcttcttatc caatcctggc ttgagccgt tcaattcctt cgttccgttt cgccaactc | 300 |
| ccttgtttac ggtgcctctg actctaacgt ctacgacctt ttgaaggacc ttgaggaggg | 360 |
| tatccaaacc cttatgggtc gtcttgagga cggttctccc cgtaccggtc aaatcttcaa | 420 |
| gcaaacctac tccaagttcg acaccaactc tcacaacgac gacgcccttt tgaagaacta | 480 |
| cggtcttttg tactgcttcc gtaaggacat ggacaaggtc gagaccttcc ttcgtatcgt | 540 |
| ccaatgccgt tctgttgagg gttcttgcgg tttctga | 577 |

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: synthetic primer

<400> SEQUENCE: 32

| | |
|---|---|
| atgcttaaga agcgtttccc caccattccc ctttc | 35 |

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: synthetic primer

<400> SEQUENCE: 33

| | |
|---|---|
| cggggtacct cagaaaccgc aagaaccctc | 30 |

<210> SEQ ID NO 34
<211> LENGTH: 528
<212> TYPE: DNA
<213> ORGANISM: Artificial Sequence
<220> FEATURE:
<223> OTHER INFORMATION: Description of Artificial Sequence: Artificial DNA coding hGCSF

<400> SEQUENCE: 34

| | |
|---|---|
| gccacccccc tgggccctgc cagctccctg ccccagagct cctgctcaa gtgcttagag | 60 |
| caagtgagga agatccaggg cgatggcgca gcgctccagg agaagctgtg tgccacctac | 120 |
| aagctgtgcc accccgagga gctggtgctg ctcggacact ctctgggcat cccctgggct | 180 |
| cccctgagca gctgccccag ccaggccctg cagctggcag gctgcttgag ccaactccat | 240 |
| agcggccttt tcctctacca ggggctcctg caggccctgg aagggatctc cccgagttg | 300 |
| ggtcccacct tggacacact gcagctggac gtcgccgact tgccaccac catctggcag | 360 |
| cagatggaag aactgggaat ggcccctgcc ctgcagccca cccagggtgc catgccggcc | 420 |
| ttcgcctctg ctttccagcg ccgggcagga ggggtcctgg ttgcctccca tctgcagagc | 480 |
| ttcctggagg tgtcgtaccg cgttctacgc caccttgccc agccctga | 528 |

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: synthetic primer

<400> SEQUENCE: 35
atgcttaaga agcgtgccac ccccctgggc cctg    34

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: synthetic
      primer

<400> SEQUENCE: 36
cggggtacct cagggctggg caaggtggc    29

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: synthetic
      primer

<400> SEQUENCE: 37
cggggtaccc ttcagctgag gcacaaaaga atcc    34

<210> SEQ ID NO 38
<211> LENGTH: 1527
<212> TYPE: DNA
<213> ORGANISM: Artificial Sequence
<220> FEATURE:
<223> OTHER INFORMATION: Description of Artificial Sequence: Artificial
      DNA coding hPDI

<400> SEQUENCE: 38
atgctgcgcc gcgctctgct gtgcctggcc gtggccgccc tggtgcgcgc cgacgccccc    60
gaggaggagg accacgtcct ggtgctgcgg aaaagcaact cgcggaggc gctggcggcc    120 cacaagtacc tgctggtgga gttctatgcc ccttggtgtg gccactgcaa ggctctggcc    180
cctgagtatg ccaaagccgc tgggaagctg aaggcagaag gttccgagat caggttggcc    240
aaggtggacg ccacggagga gtctgacctg gcccagcagt acggcgtgcg cggctatccc    300
accatcaagt tcttcaggaa tggagacacg gcttccccca ggaatatac agctggcaga    360 gaggctgatg acatcgtgaa ctggctgaag aagcgcacgg gcccggctgc caccaccctg    420
cctgacggcg cagctgcaga gtccttggtg gagtccagcg aggtggctgt catcggcttc    480
ttcaaggacg tggagtcgga ctctgccaag cagttttgc aggcagcaga ggccatcgat    540
gacataccat ttgggatcac ttccaacagt gacgtgttct ccaaatacca gctcgacaaa    600
gatggggttg tcctctttaa gaagtttgat gaaggccgga caactttga aggggaggtc    660 accaaggaga acctgctgga ctttatcaaa cacaaccagc tgccccttgt catcgagttc    720
accgagcaga cagccccgaa gatttttgga ggtgaaatca gactcacat cctgctgttc    780 ttgcccaaga gtgtgtctga ctatgacggc aaactgagca acttcaaaac agcagccgag    840
agcttcaagg gcaagatcct gttcatcttc atcgacagcg accacaccga caaccagcgc    900
atcctcgagt tctttggcct gaagaaggaa gagtgcccgg ccgtgcgcct catcaccctg    960
gaggaggaga tgaccaagta caagcccgaa tcggaggagc tgacggcaga ggagatcaca   1020
gagttctgcc accgcttcct ggagggcaaa atcaagcccc acctgatgag ccaggagctg   1080
ccggaggact gggacaagca gcctgtcaag gtgcttgttg ggaagaactt tgaagacgtg   1140

```
gcttttgatg agaaaaaaaa cgtctttgtg gagttctatg ccccatggtg tggtcactgc      1200
aaacagttgg ctcccatttg ggataaactg ggagagacgt acaaggacca tgagaacatc      1260
gtcatcgcca agatggactc gactgccaac gaggtggagg ccgtcaaagt gcacagcttc      1320
cccacactca agttctttcc tgccagtgcc gacaggacgg tcattgatta acacgggaa       1380 cgcacgctgg atggttttaa gaaattcctg gagagcggtg gccaggatgg ggcaggggat      1440
gatgacgatc tcgaggacct ggaagaagca gaggagccag acatggagga agacgatgat      1500
cagaaagctg tgaaagatga actgtaa                                          1527

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: synthetic
      primer

<400> SEQUENCE: 39
ctgacgcccc cgaggaggag ga                                                22

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: synthetic
      primer

<400> SEQUENCE: 40
cggggtacct taaaggggca gctggttgtg tttg                                   34

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: synthetic
      primer

<400> SEQUENCE: 41
cggggtacct tagccctcca ggaagcggtg gc                                     32

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: synthetic
      primer

<400> SEQUENCE: 42
cggggtacct taccagtcct ccggcagctc ctg                                    33

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: synthetic
      primer

<400> SEQUENCE: 43
cggggtacct tacagttcat ctttcacagc tttctg                                 36
```

<210> SEQ ID NO 44
<211> LENGTH: 67
<212> TYPE: DNA
<213> ORGANISM: Artificial Sequence
<220> FEATURE:
<223> OTHER INFORMATION: Description of Artificial Sequence: synthetic primer

<400> SEQUENCE: 44
ccagtcctcc ggcagctcct ggctcatcag gtggggcttg attttaaggg gcagctggtt    60
gtgtttg    67

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: synthetic primer

<400> SEQUENCE: 45
cggggtacca ggcctcttct taagccagtc ctccggcagc tcctg    45

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: synthetic primer

<400> SEQUENCE: 46
cagtcacctg ccaacttaac gccacccccc tgggccctg    39